United States Patent
Bachand et al.

(10) Patent No.: US 7,741,347 B2
(45) Date of Patent: Jun. 22, 2010

(54) HEPATITIS C VIRUS INHIBITORS

(75) Inventors: Carol Bachand, Candiac (CA);
Makonen Belema, North Haven, CT (US); Daniel H. Deon, Brossard (CA); Andrew C. Good, Wallingford, CT (US); Jason Goodrich, Meriden, CT (US); Lawrence G. Hamann, North Grafton, MA (US); Clint A. James, Longueuil (CA); David R. Langley, Meriden, CT (US); Rico Lavoie, Candiac (CA); Omar D. Lopez, Wallingford, CT (US); Alain Martel, Delson (CA); Nicholas A. Meanwell, East Hampton, CT (US); Van N. Nguyen, Meriden, CT (US); Jeffrey Lee Romine, Meriden, CT (US); Edward H. Ruediger, Greenfield Park (CA); Lawrence B. Snyder, Killingworth, CT (US); Denis R. St. Laurent, Newington, CT (US); Gan Wang, Wallingford, CT (US); Fukang Yang, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/120,494

(22) Filed: May 14, 2008

(65) Prior Publication Data

US 2008/0311075 A1    Dec. 18, 2008

Related U.S. Application Data

(60) Provisional application No. 60/938,534, filed on May 17, 2007.

(51) Int. Cl.
*A61K 31/4196* (2006.01)
*A61K 31/4245* (2006.01)
*A61K 31/4164* (2006.01)
*C07D 271/10* (2006.01)
*C07D 249/08* (2006.01)

(52) U.S. Cl. .................. 514/364; 514/383; 514/400; 548/143; 548/269.4; 548/314.7

(58) Field of Classification Search ............... 514/364, 514/383, 400; 548/143, 269.4, 314.7
See application file for complete search history.

(56) References Cited

U.S. PATENT DOCUMENTS 5,654,451 A    8/1997    Kari

FOREIGN PATENT DOCUMENTS

| WO | WO94/15909 | 7/1994 |
|---|---|---|
| WO | WO2006093867 | 9/2006 |
| WO | WO2006/133326 | 12/2006 |
| WO | WO2007/031791 | 3/2007 |
| WO | WO2007/058384 | 5/2007 |
| WO | WO2007/077186 | 7/2007 |
| WO | WO2007/138242 | 12/2007 |
| WO | WO2008/021927 | 2/2008 |
| WO | WO2008/021936 | 2/2008 |
| WO | WO2008021928 | 2/2008 |

OTHER PUBLICATIONS

U.S. Appl. No. 12/030,232, filed Feb. 13, 2008, Bachand, et al.
U.S. Appl. No. 12/029,680, filed Feb. 12, 2008, Bachand, et al.

*Primary Examiner*—Kamal A Saeed
*Assistant Examiner*—Samantha L Shterengarts
(74) *Attorney, Agent, or Firm*—Pamela A. Mingo

(57) ABSTRACT

The present disclosure relates to compounds, compositions and methods for the treatment of Hepatitis C virus (HCV) infection. Also disclosed are pharmaceutical compositions containing such compounds and methods for using these compounds in the treatment of HCV infection.

13 Claims, No Drawings

HEPATITIS C VIRUS INHIBITORS

CROSS-REFERENCE TO RELATED APPLICATIONS

This application claims the benefit of U.S. Provisional Application Ser. No. 60/938,534 filed May 17, 2007.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1-12; and in Park, K.-J.; Choi, S.-H, *J. Biological Chemistry* 2003.

In a first aspect the present disclosure provides a compound of formula (I)

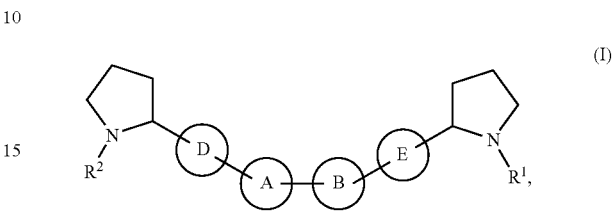

or a pharmaceutically acceptable salt thereof, wherein
A and B are each phenyl;
D and E are each five-membered aromatic rings containing one, two, or three heteroatoms independently selected from nitrogen, oxygen, and sulfur; provided that at least one of D and E is other than imidazole;
$R^1$ and $R^2$ are independently selected from hydrogen and $R^3$—C(O)—; and
each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^aR^d)$alkyl, and $(NR^aR^d)$carbonyl.

In a first embodiment of the first aspect the present disclosure provides a compound of Formula (I), or a pharmaceutically acceptable salt thereof, wherein one of D and E is imidazole.

In a second embodiment of the first aspect the present disclosure provides a compound of Formula (I), or a pharmaceutically acceptable salt thereof, wherein at least one of D and E is selected from pyrazole, triazole, and oxadiazole.

In a third embodiment of the first aspect the present disclosure provides a compound of Formula (I), or a pharmaceutically acceptable salt thereof, wherein $R^3$ is selected from alkoxy and arylalkyl.

In a second aspect the present disclosure provides a compound of Formula (II)

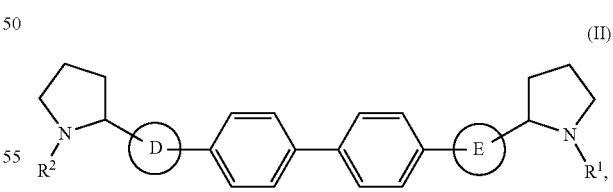

or a pharmaceutically acceptable salt thereof, wherein
D and E are each five-membered aromatic rings containing one, two, or three heteroatoms independently selected from nitrogen, oxygen, and sulfur; provided that at least one of D and E is other than imidazole;
$R^1$ and $R^2$ are independently selected from hydrogen and $R^3$—C(O)—; and
each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (R$^c$R$^d$)alkyl, and (NR$^a$R$^d$)carbonyl.

In a third aspect the present disclosure provides a compound of Formula (III)

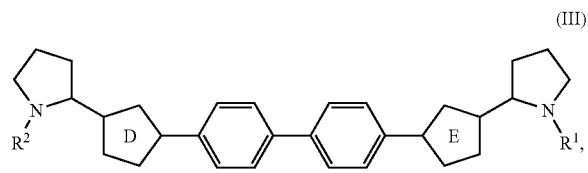

or a pharmaceutically acceptable salt thereof, wherein

D and E are each five-membered aromatic rings containing one, two, or three heteroatoms independently selected from nitrogen, oxygen, and sulfur; provided that at least one of D and E is other than imidazole; and provided that both D and E are each substituted through carbon atoms;

$R^1$ and $R^2$ are independently selected from hydrogen and $R^3$—C(O)—; and each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, R$^c$R$^d$)alkenyl, (R$^c$R$^d$)alkyl, and (NR$^a$R$^d$)carbonyl.

In a first embodiment of the third aspect the present disclosure provides a compound of Formula (III), or a pharmaceutically acceptable salt thereof, wherein D and E are independently selected from imidazole, pyrazole, triazole, and oxadiazole; provided at least one of D and E is other than imidazole; and provided that both D and E are each substituted through carbon atoms; and $R^3$ is selected from alkoxy and arylalkyl.

In a fourth aspect the present disclosure provides a composition comprising a compound of Formula (I), or a pharmaceutically acceptable salt thereof, and a pharmaceutically acceptable carrier. In a first embodiment of the fourth aspect the composition further comprises one or two additional compounds having anti-HCV activity. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastoid interferon tau.

In a fourth embodiment of the fourth aspect the disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the fourth aspect the disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fifth aspect the present disclosure provides a method of treating an HCV infection in a patient, comprising administering to the patient a therapeutically effective amount of a compound of Formula (I), or a pharmaceutically acceptable salt thereof. In a first embodiment of the fifth aspect the method further comprises administering one or two additional compounds having anti-HCV activity prior to, after, or simultaneously with the compound of Formula (I) or the pharmaceutically acceptable salt thereof. In a second embodiment of the fifth aspect at least one of the additional compounds is an interferon or a ribavirin. In a third embodiment of the fifth aspect the interferon is selected from interferon alpha 2B, pegylated interferon alpha, consensus interferon, interferon alpha 2A, and lymphoblastoid interferon tau.

In a sixth aspect the present disclosure provides a method of treating an HCV infection in a patient, comprising administering to the patient a therapeutically effective amount of a compound of Formula (I), or a pharmaceutically acceptable salt thereof, and administering one or two additional compounds having anti-HCV activity prior to, after, or simultaneously with the compound of Formula (I) or the pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a seventh aspect the present disclosure provides a method of treating an HCV infection in a patient, comprising administering to the patient a therapeutically effective amount of a compound of Formula (I), or a pharmaceutically acceptable salt thereof, and administering one or two additional compounds having anti-HCV activity prior to, after, or simultaneously with the compound of Formula (I) or the pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when u is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The terms "Cap" and "cap", as used herein, refer to the group which is placed on the nitrogen atom of the pyrrolidine ring in the compounds of formula (I). It should be understood that "Cap" or "cap" can also refer to the reagent which is a precursor to the final "cap" in compounds of formula (I) and is used as one of the starting materials in the reaction to append a group on the pyrrolidine nitrogen that results in the final product, a compound which contains the functionalized pyrrolidine that will be present in the compound of formula (I).

The term "carbonyl," as used herein, refers to —C(O)—.

The term "carboxy," as used herein, refers to —CO$_2$H.

The term "cyano," as used herein, refers to —CN.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^xR^y$, ($NR^xR^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —$NR^cR^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^xR^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^xR^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to an alkenyl group substituted with one, two, or three —NR$^c$R$^d$ groups.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and (NR$^e$R$^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "(NR$^c$R$^d$)carbonyl," as used herein, refers to an —NR$^c$R$^d$ group attached to the parent molecular moiety through a carbonyl group.

The term "—NR$^e$R$^f$," as used herein, refers to two groups, R$^e$ and R$^f$ which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl) alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "oxo," as used herein, refers to =O.

The term "sulfonyl," as used herein, refers to —SO$_2$—.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabutlin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |

TABLE 1-continued

| Brand Name | Physiological Class | Type of Inhibitor or Target | Source Company |
|---|---|---|---|
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |

TABLE 1-continued

| Brand Name | Physiological Class | Type of Inhibitor or Target | Source Company |
|---|---|---|---|
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: TEA and NEt$_3$ for triethylamine; DMF for N,N-dimethylformamide; THF for tetrahydrofuran; HATU for O-(7-azabenzotriazol-1-yl)-N,N,N',N'-tetramethyluronium hexafluorophosphate; Et for ethyl; Boc or BOC for tert-butoxycarbonyl; Me for methyl; EtOH for ethanol; DMSO for dimethylsulfoxide; MeOH for methanol; MeLi for methyllithium; tBuLi or tert-BuLi for tert-butyllithium; TFA for trifluoroacetic acid; Et$_2$O for diethyl ether; Ph for phenyl; OAc for acetate; DME for 1,2-dimethoxyethane; DEPBT for 3-(diethoxyphosphoryloxy)-1,2,3-benzotriazin-4(3H)-one; iPr$_2$EtN or DIPEA for diisopropylethylamine; EDCI for 1-(3-dimethylaminopropyl)-3-ethylcarbodiimide hydrochloride; DMAP for 4-dimethylaminopyridine; DBU for 1,8-diazabicyclo[5.4.0]undec-7-ene; t-Bu for tert-butyl; and HMDS for hexamethyldisilazide.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

EXAMPLES

Preparation of Intermediate 4: (S)-tert-butyl 2-(5-(4-bromophenyl)-1H-pyrazol-3-yl)pyrrolidine-1-carboxylate

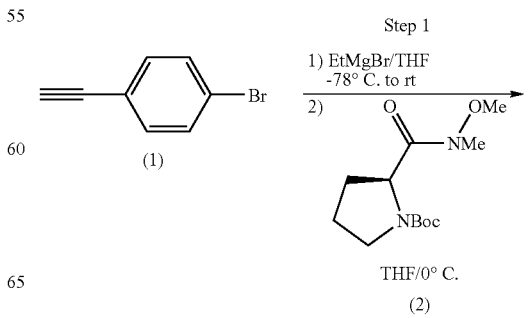

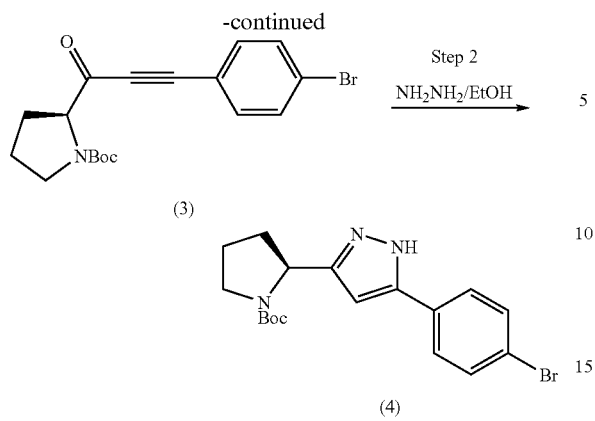

Step 1: To a solution of 4-bromophenylacetylene (1) (0.917 g, 5.06 mmol) in THF (20 mL) at 0° C. was added dropwise a solution of ethyl magnesium bromide (3M in THF, 1.8 mL, 5.4 mmol). After 10 minutes the cooling bath was removed and the mixture allowed to stir at room temperature for 1 hour. The reaction mixture was then recooled to 0° C. and added to a solution of N-(tert-butoxycarbonyl)-L-proline-N'-methoxy-N'-methylamide (2) (0.970 g, 3.76 mmol) in THF (10 mL). The reaction mixture was warmed to room temperature, allowed to stir for 2 hours and then quenched with saturated $NH_4Cl$. The mixture was diluted with ethyl acetate/$H_2O$ and the layers separated. The aqueous phase was back-extracted with ethyl acetate (2×) and the combined organic layers were washed ($H_2O$, brine), dried ($Na_2SO_4$), and filtered. The solvent was removed in vacuo and the residue purified by flash chromatography (hexane:ethyl acetate, 4:1) to give intermediate (3) as a cream colored solid (1.26 g, 89%). $^1$H NMR (400 MHz, DMSO-$d_6$) δ 7.71-7.73 (m, 2H), 4.26-4.32 (m, 1H), 3.39-3.49 (m, 2H), 2.20-2.32 (m, 1H), 1.81-2.00 (m, 3H), 1.36, 1.31 (s, 9H, rotamers in 2:3 ratio); LCMS: Anal. Calcd. for $C_{18}H_{20}BrNO_3$: 377. found: 278 (M+H-Boc)$^+$.

Step 2: A mixture of (S)-tert-butyl 2-(3-(4-bromophenyl)propioloyl)pyrrolidine-1-carboxylate (3) (0.759 g, 2.01 mmol) and hydrazine hydrate (55% w/w aqueous solution, 0.19 mL, 2.15 mmol) in ethanol (10 mL) was heated at 80° C. for 16 hours. The solvent was then removed and the residue was partitioned with ethyl acetate/$H_2O$. The aqueous phase was re-extracted with ethyl acetate (2×) and the combined organic layers were washed ($H_2O$, brine), dried ($Na_2SO_4$), and filtered. The solvent was removed in vacuo to provide intermediate (4) as a colorless foam (0.812 g, quant.; $^1$H NMR indicated the presence of residual ethyl acetate.); $^1$H NMR (400 MHz, DMSO-$d_6$) δ 13.0 (s, 0.4H), 12.8 (s, 0.6H), 7.54-7.73 (m, 4H), 6.50 (s, 1H), 4.8 (m, 1H), 3.50 (s, br, 1H), 2.17 (s, br, 1H), 1.84-1.88 (m, 3H), 1.38, 1.18 (s, 9H, rotamers in 2:3 ratio); LCMS: Anal. Calcd. for $C_{18}H_{22}BrN_3O_2$: 391. found: 392 (M+H)$^+$.

Preparation of Intermediate 8: (S)-tert-Butyl 2-(5-(4-iodophenyl)-1H-pyrazol-3-yl)pyrrolidine-1-carboxylate

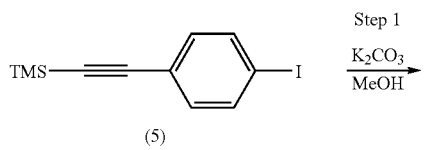

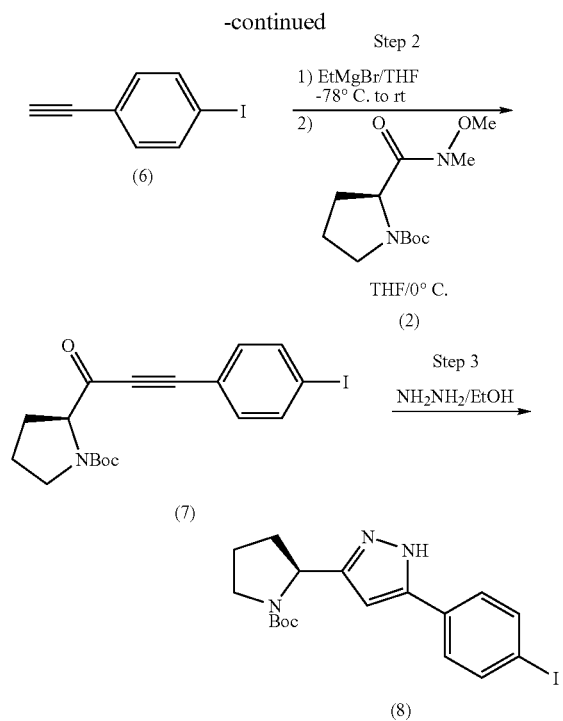

Step 1: To a solution of ((4-iodophenyl)ethynyl)trimethylsilane (5) (2.07 g, 6.23 mmol) in methanol (40 mL) was added $K_2CO_3$ (8.0 g, 57.9 mmol) and the reaction was allowed to stir for 48 hours. The volatiles were then removed in vacuo and the residue partitioned between ethyl acetate and $H_2O$. The layers were separated and the aqueous phase re-extracted with ethyl acetate (2×). The combined organic layers were washed ($H_2O$, brine), dried ($Na_2SO_4$), and filtered. The solvent was removed in vacuo and the residue was crystallized from hexane at −20° C. (in 2 crops) to give 1-ethynyl-4-iodobenzene (6) as a colorless solid (0.92 g, 64%). $^1$H NMR (400 MHz, DMSO-$d_6$) δ 7.66 (app d, J=8.6 Hz, 2H), 7.20 (app d, J=8.5 Hz, 2H), 1.54 (s, 1H).

Step 2: To a solution of 1-ethynyl-4-iodobenzene 6 (0.908 g, 3.98 mmol) in THF (20 mL) at −78° C. was added ethylmagnesium bromide (3M in ether, 1.39 mL, 4.18 mmol). After 10 minutes the cooling bath was removed and the solution was allowed to stir at room temperature for 1 hour. The reaction mixture was then re-cooled to 0° C. and added to a solution of N-(tert-butoxycarbonyl)-L-proline N'-methoxy-N'-methylamide 2 (0.970 g, 3.76 mmol) in THF (10 mL). The reaction mixture was warmed to room temperature and stirring was continued for 12 hours before the mixture was quenched with saturated $NH_4Cl$. The mixture was diluted with ethyl acetate/$H_2O$, the layers separated and the aqueous phase was re-extracted with ethyl acetate (2×). The combined organic layers were washed ($H_2O$, brine), dried ($Na_2SO_4$), and filtered, and the solvent was removed in vacuo. The resulting residue was purified by flash chromatography (hexane:ethyl acetate, 4:1) to give (S)-tert-butyl 2-(3-(4-iodophenyl)propioloyl)pyrrolidine-1-carboxylate 7 (0.908 g, 71%) as a yellow oil which solidified on standing. $^1$H NMR (400 MHz, CDCl$_3$) δ 7.72-7.76 (m, 2H), 7.26-7.30 (m, 2H), 4.49 (dd, J=8.8, 4.3 Hz, 0.3H), 4.29 (dd, J=8.5, 5.5 Hz, 0.7H), 3.59 (app t, J=6.7 Hz, 2H), 2.20-2.33 (m, 1H), 1.85-2.10 (m, 3H), 1.45, 1.40 (s, 9H, rotamers in 2:3 ratio). LCMS: Anal. Calcd. for $C_{18}H_{20}INO_3$: 425. found: 326 (M+H-Boc)$^+$.

Step 3: A solution of (S)-tert-butyl 2-(3-(4-iodophenyl) propioloyl)pyrrolidine-1-carboxylate 7 (0.905 g, 2.13 mmol) and hydrazine (55% w/w aqueous solution, 0.21 mL, 2.25 mmol) in ethanol (20 mL) was heated at 85° C. for 3 hours. The solvent was then removed in vacuo and the residue was partitioned with H$_2$O/ethyl acetate. The layers were separated and the aqueous phase was re-extracted with ethyl acetate (2×) and the combined organic layers were washed (H$_2$O, brine), dried (Na$_2$SO$_4$), and filtered. The solvent was removed in vacuo to give the title compound 8 (0.966 g, quant.) as a colorless foam. $^1$H NMR (400 MHz, CDCl$_3$) δ 7.70 (app d, J=8.2 Hz, 2H), 7.51 (app d, J=8.2 Hz, 2H), 6.36 (s, 1H), 4.94-5.02 (m, 1H), 3.38-3.55 (m, 2H), 2.25-2.29 (m, 2H), 1.89-2.05 (m, 2H). LCMS: Anal. Calcd. for C$_{18}$H$_{22}$IN$_3$O$_2$: 439. found: 340 (M+H-Boc)$^+$.

Preparation of Intermediate 9a: 4,4'-bis(3-((S)-pyrrolidin-2-yl)-1H-pyrazol-5-yl)biphenyl

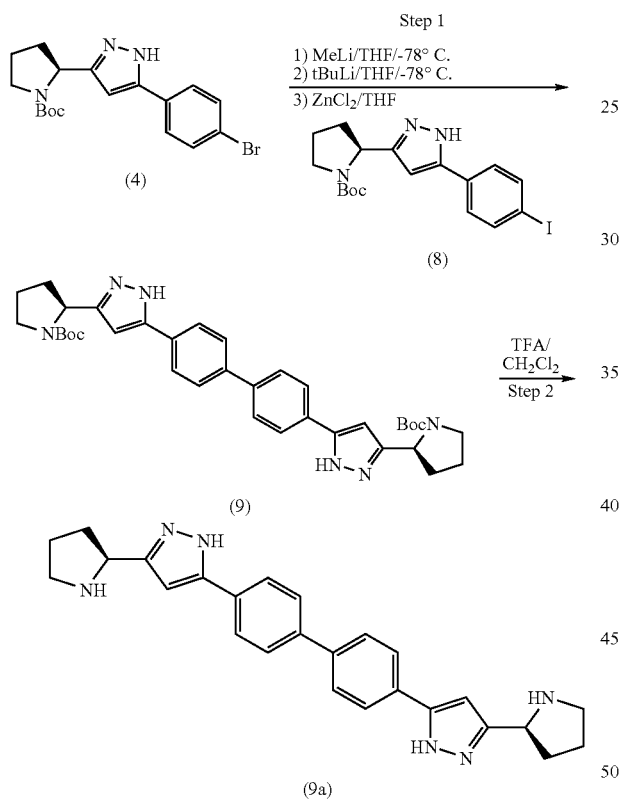

Step 1: To a solution of (S)-tert-butyl 2-(5-(4-bromophenyl)-1H-pyrazol-3-yl)pyrrolidine-1-carboxylate (4) (0.187 g, 0.476 mmol) in THF (5 mL) at −78° C. was added MeLi (1.6M in Et$_2$O, 0.31 mL, 0.496 mmol), followed by tert-BuLi (1.7M in pentane, 0.64 mL, 1.09 mmol). After 10 min, a solution of freshly fused ZnCl$_2$ (0.091 g, 0.668 mmol) in THF (2 mL) was added via cannula. The solution was allowed to stir for 30 minutes and then the cooling bath was removed and the solution allowed to warm to room temperature. To this mixture was added (S)-tert-butyl 2-(5-(4-iodophenyl)-1H-pyrazol-3-yl)pyrrolidine-1-carboxylate (8) (0.305 g, 0.694 mmol) and Pd(PPh$_3$)$_4$ (0.032 g, 0.0277 mmol) and the mixture was heated at 70° C. under Ar for 12 hours. After cooling to room temperature, saturated NH$_4$Cl was added and the mixture was partitioned with ethyl acetate/H$_2$O. The aqueous phase was separated and re-extracted with ethyl acetate (2×), and the combined organic layers were washed (H$_2$O, brine), dried (Na$_2$SO$_4$), and filtered. The solvent was removed in vacuo and the residue was purified by flash chromatography (0-100% ethyl acetate-hexane) and then repurified using preparative HPLC (CH$_3$CN:H$_2$O:NH$_4$OAc) to give an oil which was a mixture of the desired product (9) and the starting aryliodide (8) (ca. 1:1 by LCMS). $^1$H NMR (400 MHz, CD$_3$OD) δ 7.80 (s, br, 2H), 7.73 (s, br, 2H), 7.61-7.66 (m, 2H), 7.52-7.57 (m, 2H), 6.50 (s, 2H), 4.8 (m, 2H, partially obscured by solvent), 3.61-3.63 (m, 2H), 3.47-3.51 (m, 2H), 2.30-2.35 (m, 2H), 1.93-2.03 (m, 6H), 1.47 (s, 6H), 1.28 (s, 12H). LCMS: Anal. Calcd. for C$_{36}$H$_{44}$N$_6$O$_4$: 624. found: 625 (M+H)$^+$.

Intermediate (9) was dissolved in CH$_2$Cl$_2$ (2 mL) and TFA (2 mL) and allowed to stir at room temperature for 1 hour. The solvents were removed in vacuo and the crude residue was purified by preparative HPLC (CH$_3$CN:H$_2$O:TFA) to give the TFA salt of 4,4'-bis(3-((S)-pyrrolidin-2-yl)-1H-pyrazol-5-yl) biphenyl 9a (0.08 g, 26%) as a white solid. $^1$H NMR (400 MHz, CD$_3$OD) δ 7.81 (A of app AB q, J=8.5 Hz, 4H), 7.78 (B of app AB q, J=8.5 Hz, 4H), 6.80 (s, 2H), 4.78 (dd, (app t) J=7.3, 8.1 Hz, 2H), 3.40-3.51 (m, 4H), 2.47-2.55 (m, 2H), 2.14 (m, 6H). LCMS: Anal. Calcd. for C$_{28}$H$_{28}$N$_6$: 424. found: 425 (M+H)$^+$.

Preparation of Intermediate 16: (S)-tert-butyl 2-(5-(4-(4,4,5,5-tetramethyl-1,3,2-dioxaborolan-2-yl)phenyl)-4H-1,2,4-triazol-3-yl)pyrrolidine-1-carboxylate

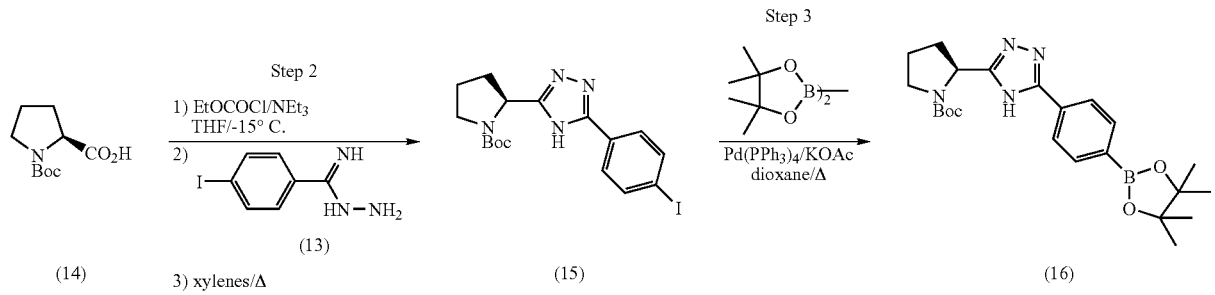

-continued

Step 1  1) HCl/MeOH
        2) NH₂NH₂/MeOH

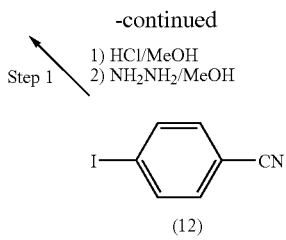

(12)

Step 1: Anhydrous HCl gas was bubbled through a solution of 4-iodobenzonitrile 12 (2.22 g, 9.74 mmol) in dry methanol (80 mL) at 0° C. for 40 minutes and the mixture was then allowed to stir for 48 hours. The solvent was removed in vacuo (the vessel was back-filled with Ar to avoid introduction of moisture) and the residue was dissolved in dry methanol (40 mL). This solution was then added to a solution of hydrazine hydrate (55% w/w aqueous solution, 3.0 mL, 33.9 mmol) at room temperature and the mixture was stirred for 1 hour before the solvent was removed in vacuo. The residue was triturated with dry THF and the mixture was filtered to remove insoluble salts. The resulting THF solution of 4-iodobenzimidohydrazide (13) was used directly in the next step.

Step 2: To a solution of (S)-1-(tert-butoxycarbonyl)pyrrolidine-2-carboxylic acid (14) (1.81 g, 8.39 mmol) in THF (30 mL) cooled to −10° C. under Ar was added NEt₃ (1.2 mL, 8.6 mmol) and then isobutylchloroformate (1.1 mL, 8.5 mmol). The mixture was allowed to stir for 20 minutes at −10° C. and then filtered under Ar while cold. To the resultant solution was added dropwise the THF solution of 4-iodobenzimidohydrazide prepared in the previous step. The reaction mixture was allowed to stir for 2 hours and then the solvent was removed in vacuo. Approximately half of the crude material (ca. 4.19 mmol) was taken up in xylene (40 mL) and the mixture was placed in an oil-bath pre-heated to 185° C. After 30 minutes the reaction mixture was cooled, the solvent was removed in vacuo and the residue was purified by column chromatography (hexane:ethyl acetate, 2:1) and then crystallized (hexane-ethyl acetate) to give (S)-tert-butyl 2-(5-(4-iodophenyl)-4H-1,2,4-triazol-3-yl)pyrrolidine-1-carboxylate as a colorless solid (15) (0.438 g, 24%). ¹H NMR (400 MHz, DMSO-d₆) δ 13.91 (s, 1H), 7.74-7.88 (m, 4H), 4.84-4.93 (m, 1H), 3.51-3.55 (m, 1H), 3.33-3.37 (m, 1H, partially obscured by H₂O peak), 2.21-2.32 (m, 1H), 1.87-1.91 (m, 3H), 1.38 (s, 4H), 1.13 (s, 5H). LCMS: Anal. Calcd. for $C_{17}H_{21}N_4O_2$: 440. found: 441 (M+H)⁺.

Step 3: A mixture of (S)-tert-butyl 2-(5-(4-iodophenyl)-4H-1,2,4-triazol-3-yl)pyrrolidine-1-carboxylate (15) (0.210 g, 0.476 mmol), bis(pinacolato)diboron (0.261 g, 1.03 mmol), KOAc (0.136 g, 1.39 mmol) and Pd(PPh₃)₄ (0.025 g, 0.0217 mmol) in dioxane (5 mL) was degassed with a stream of Ar for 15 minutes. The mixture was then heated at 85° C. for 12 hours, at which time it was charged with a further 0.130 g (0.5 mmol) of bis(pinacolato)diboron and 0.012 g (0.011 mmol) of Pd(PPh₃)₄ and heated for another 36 hours. The cooled mixture was poured into ethyl acetate/H₂O and the layers were separated. The aqueous phase was re-extracted with ethyl acetate (2×) and the combined organic layers were washed (H₂O, brine) and dried (Na₂SO₄) and filtered. The solvent was removed in vacuo and the residue purified by flash chromatography (hexane:ethyl acetate, 1:1) to afford (S)-tert-butyl 2-(5-(4-(4,4,5,5-tetramethyl-1,3,2-dioxaborolan-2-yl)phenyl)-4H-1,2,4-triazol-3-yl)pyrrolidine-1-carboxylate (16) (0.161 g, 77%). as a colorless solid. ¹H NMR suggested that the material was contaminated with ca. 5-10% of bis(pinacolato)diboron, but it was used as such in subsequent steps. ¹H NMR (400 MHz, DMSO-d₆) δ 14.23 (s, 0.3H), 13.92 (s, 0.7H), 7.99 (A of app AB quartet, d, J=7.4 Hz, 2H), 7.73 (B of app AB quartet, d, J=7.4 Hz, 4H), 4.81-4.93 (m, 1H), 3.53 (s, br, 1H), 3.35-3.39 (m, 1H), 1.38 (s, 3H), 1.30 (s, 12H), 1.13 (s, 6H). LCMS: Anal. Calcd. for $C_{23}H_{33}BN_4O_4$: 440. found: 441 (M+H)⁺.

Preparation of Intermediate 19: (S)-tert-butyl 2-(5-(4'-(2-((S)-1-(tert-butoxycarbonyl)pyrrolidin-2-yl)-1H-imidazol-5-yl)biphenyl-4-yl)-1H-pyrazol-3-yl)pyrrolidine-1-carboxylate

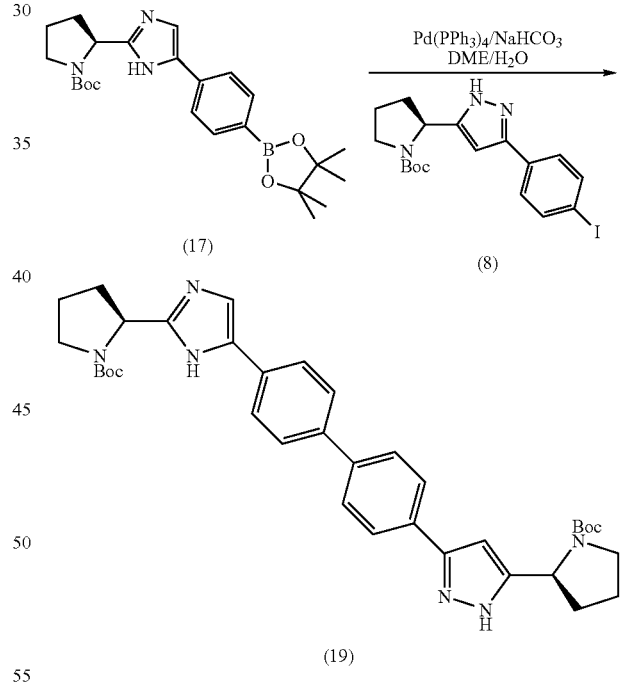

General Method A: A mixture of (S)-tert-butyl 2-(5-(4-(4,4,5,5-tetramethyl-1,3,2-dioxaborolan-2-yl)phenyl)-1H-imidazol-2-yl)pyrrolidine-1-carboxylate (17) (Scheme 9; 0.138 g, 0.314 mmol), (S)-tert-butyl 2-(5-(4-iodophenyl)-1H-pyrazol-3-yl)pyrrolidine-1-carboxylate 8 (0.141 g, 0.321 mmol), NaHCO₃ (0.110 g, 1.31 mmol) and Pd(PPh₃)₄ (0.024 g, 0.0208 mmol) in a mixture of DME (3 mL) and H₂O (1 mL) was heated at 80° C. under Ar for 12 hours. The cooled mixture was diluted with ethyl acetate/H₂O, the layers separated and the aqueous phase was re-extracted with ethyl acetate (2×). The combined organic layers were washed ($H_2O$, brine) and dried ($Na_2SO_4$) and filtered and the solvent was removed in vacuo. The resulting residue was purified by flash chromatography (hexane:ethyl acetate, 2:1 and then ethyl acetate:methanol, 9:1) to give (S)-tert-butyl 2-(5-(4'-(2-((S)-1-(tert-butoxycarbonyl)pyrrolidin-2-yl)-1H-imidazol-5-yl)biphenyl-4-yl)-1H-pyrazol-3-yl)pyrrolidine-1-carboxylate (19) (0.084 g, 43%) as a yellow solid. $^1$H NMR (400 MHz, DMSO-$d_6$) δ 13.01, 12.69, 12.20, 11.91, 11.85 (s, 1H), 7.63-7.85 (m, 8H), 7.50-7.56 (m, 1H), 6.52 (s, 1H), 4.75-4.94 (m, 2H), 3.42-3.58 (m, 2H), 3.30-3.39 (m, 2H, partially obscured by $H_2O$ signal), 2.10-2.28 (m, 2H), 1.81-2.01 (m, 6H), 1.40 (s, 7H), 1.20-1.23 (m, 6H), 1.13-1.15 (m, 5H). LCMS: Anal. Calcd. for $C_{36}H_{44}N_6O_4$: 624. found: 625 $(M+H)^+$.

The following intermediates were also prepared using General Method A above:

| Intermediate | Structure | LCMS |
|---|---|---|
| 20 | 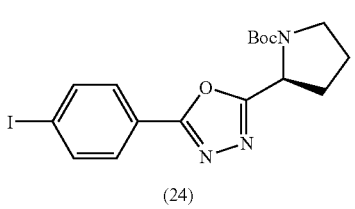 from (15) and (16) | Colorless solid (0.046 g, 16%) LCMS: Anal. Calcd. for $C_{34}H_{42}N_8O_4$: 626; found: 627 $(M + H)^+$. |
| 21 | 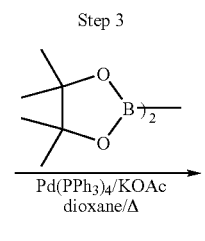 from (16) and (28) | Colorless solid (0.038 g, 4%) LCMS: Anal. Calcd. for $C_{35}H_{43}N_7O_4$: 625; found: 626 $(M + H)^+$. |

Preparation of Intermediate 26: (S)-4-(5-(1-(tert-butoxycarbonyl)pyrrolidin-2-yl)-1,3,4-oxadiazol-2-yl)phenylboronic acid

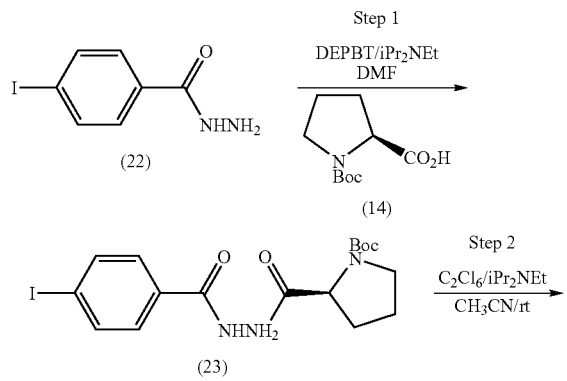

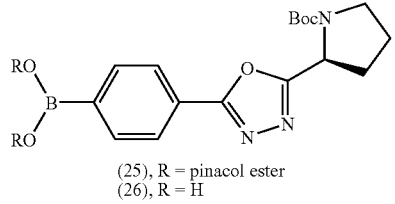

(25), R = pinacol ester
(26), R = H

Step 1: To a solution of 4-iodobenzoylhydrazide (22) (1.20 g, 4.58 mmol), (S)-1-(tert-butoxycarbonyl)pyrrolidine-2-carboxylic acid (14) (1.03 g, 4.79 mmol) and i-$Pr_2$NEt (2.0 mL, 11.2 mmol) in DMF (75 mL) was added 3-(diethoxyphosphoryloxy)-1,2,3-benzotriazin-4(3H)-one (DEPBT) (2.00 g, 6.68 mol) portionwise. The reaction mixture was stirred at room temperature for 2 hours and then it was poured into $H_2O$/ethyl acetate. The layers were separated. The aqueous phase was extracted with ethyl acetate (2×) and the combined organic layers were washed (H$_2$O, brine) and dried (Na$_2$SO$_4$) and filtered. The solvent was removed in vacuo and the residue purified by flash chromatography (hexane:ethyl acetate, 1:1) to afford the diacylhydrazide (23) as a colorless foam (1.99 g, 99%). $^1$H NMR (400 MHz, DMSO-d$_6$) δ 10.52 (s, 0.5H), 10.39 (s, 0.5H), 9.94 (d, J=7.9 Hz, 1H), 7.88 (app dd, J=8.5, 5.2 Hz, 2H), 7.64 (app d, J=8.5 Hz, 2H), 4.18 (unresolved ddd, 1H), 3.37-3.43 (m, 1H), 3.24-3.29 (m, 1H), 2.10-2.17 (m, 1H), 1.75-1.96 (m, 3H), 1.38 (s, 4.5H), 1.37 (s, 4.5H). LCMS: Anal. Calcd. for C$_{17}$H$_{22}$IN$_3$O$_4$: 459. found: 460 (M+H)$^+$.

Step 2: To a suspension of the diacylhydrazide (23) prepared in the previous step, PPh$_3$ (1.71 g, 6.54 mmol) and i-Pr$_2$NEt (2.30 mL, 12.97 mmol) in CH$_3$CN (50 mL) at room temperature was added hexachloroethane (1.41 g, 5.97 mmol). The reaction was stirred at room temperature for 1.5 hours and then the solvent was removed in vacuo and the residue was partitioned with ethyl acetate/H$_2$O. The layers were separated, the aqueous phase was re-extracted with ethyl acetate (2×) and the combined organic layers were washed (H$_2$O, brine) and dried (Na$_2$SO$_4$). The solvent was removed in vacuo and the residue was purified by column chromatography (hexane:ethyl acetate, 3:1) to give (S)-tert-butyl 2-(5-(4-iodophenyl)-1,3,4-oxadiazol-2-yl)pyrrolidine-1-carboxylate 24 (1.89 g, 99%) as a colorless oil. $^1$H NMR (400 MHz, DMSO-d$_6$) δ 7.98 (A of app AB quartet, d, J=8.4 Hz, 2H), 7.74 (A of app AB quartet, d, J=8.4 Hz, 2H), 5.02-5.06 (m, 1H), 3.47-3.53 (m, 1H), 3.36-3.41 (m, 1H), 2.26-2.32 (m, 1H), 1.91-2.09 (m, 3H), 1.37 (s, 4H), 1.17 (s, 5H). LCMS: Anal. Calcd. for C$_{17}$H$_{20}$IN$_3$O$_3$: 441. found: 442 (M+H)$^+$.

Step 3: A mixture of (S)-tert-butyl 2-(5-(4-iodophenyl)-1,3,4-oxadiazol-2-yl)pyrrolidine-1-carboxylate (24) (0.574 g, 1.30 mmol), bis(pinacolato)diboron (0.665 g, 2.62 mmol), KOAc (0.641 g, 6.53 mmol) and Pd(PPh$_3$)$_4$ (0.076 g, 0.0658 mmol) in dioxane (5 mL) was degassed with a stream of Ar for 15 minutes. The mixture was then heated at 100° C. for 12 hours, cooled to room temperature and poured into ethyl acetate/H$_2$O. The layers were separated, the aqueous phase was re-extracted with ethyl acetate (2×) and the combined organic layers were washed (H$_2$O, brine) and dried (Na$_2$SO$_4$) and filtered. The solvent was removed in vacuo and the residue purified by flash chromatography (hexane:ethyl acetate, 1:1) to give a mixture of the title boronate ester (25) and boronic acid (26). This mixture was repurified by prep HPLC (CH$_3$CN:H$_2$O:TFA) to afford (S)-4-(5-(1-(tert-butoxycarbonyl)pyrrolidin-2-yl)-1,3,4-oxadiazol-2-yl)phenylboronic acid 26 as a colorless solid (0.101 g, 22%). $^1$HNMR (400 MHz, DMSO-d$_6$) δ 8.31 (s, br, 2H), 7.94-8.00 (m, 4H), 5.03-5.10 (m, 1H), 3.37-3.42 (m, 2H), 2.31-2.40 (m, 1H), 1.92-2.04 (m, 3H). 1.38 (s, 3H), 1.18 (s, 6H); LCMS: Anal. Calcd. for C$_{17}$H$_{22}$BN$_3$O$_5$: 359. found: 360 (M+H)$^+$.

Preparation of Intermediate 29: (S)-tert-Butyl 2-(5-(4'-(5-((S)-1-(tert-butoxycarbonyl)pyrrolidin-2-yl)-1,3,4-oxadiazol-2-yl)biphenyl-4-yl)-1H-imidazol-2-yl)pyrrolidine-1-carboxylate

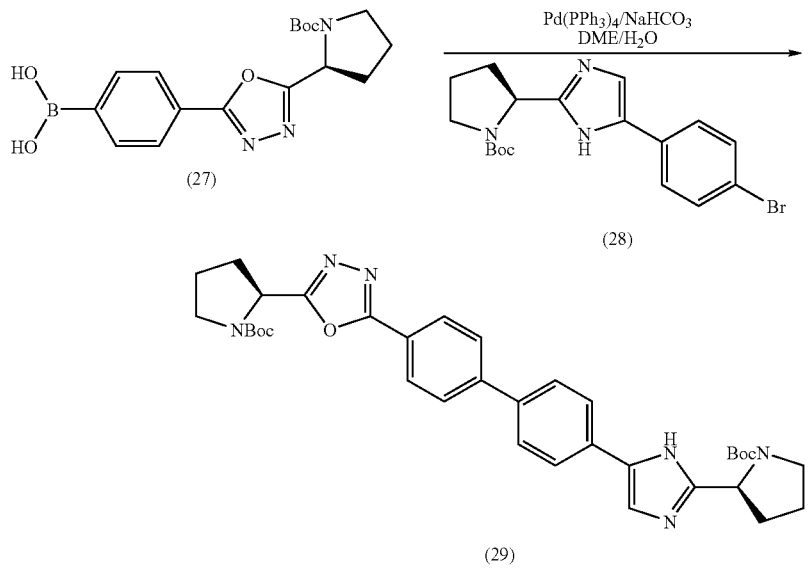

A mixture (S)-4-(5-(1-(tert-butoxycarbonyl)pyrrolidin-2-yl)-1,3,4-oxadiazol-2-yl)phenylboronic acid (27) (0.090 g, 0.251 mmol), (S)-tert-butyl 2-(5-(4-bromophenyl)-1H-imidazol-2-yl)pyrrolidine-1-carboxylate (28) (Scheme 9; 0.098 g, 0.250 mmol), NaHCO$_3$ (0.076 g, 0.906 mmol) and Pd(PPh$_3$)$_4$ (0.019 g, 0.016 mmol) in a mixture of DME (3 mL) and H$_2$O (1 mL) was degassed with a stream of Ar for 15 minutes and the mixture was then heated at 80° C. for 12 hours. The cooled mixture was diluted with ethyl acetate/H$_2$O, the layers were separated and the aqueous phase was re-extracted with ethyl acetate (2×). The combined organic layers were washed (H$_2$O, brine) and dried (Na$_2$SO$_4$) and filtered, and the solvent was removed in vacuo. Purification of the residue by prep HPLC (CH$_3$CN:H$_2$O:NH$_4$OAc) gave the title compound 29 (0.045 g, 29%) as a light yellow glass. LCMS: Anal. Calcd. for C$_{35}$H$_{42}$N$_6$O$_5$: 626. found: 627 (M+H)$^+$.

Preparation of Example 30: Dimethyl-(1R,1'R)-2,2'-((2S,2'S)-2,2'-(5,5'-(biphenyl-4,4'-diyl)bis(1H-pyrazole-5,3-diyl))bis(pyrrolidine-2,1-diyl))bis(2-oxo-1-phenylethane-2,1-diyl)dicarbamate

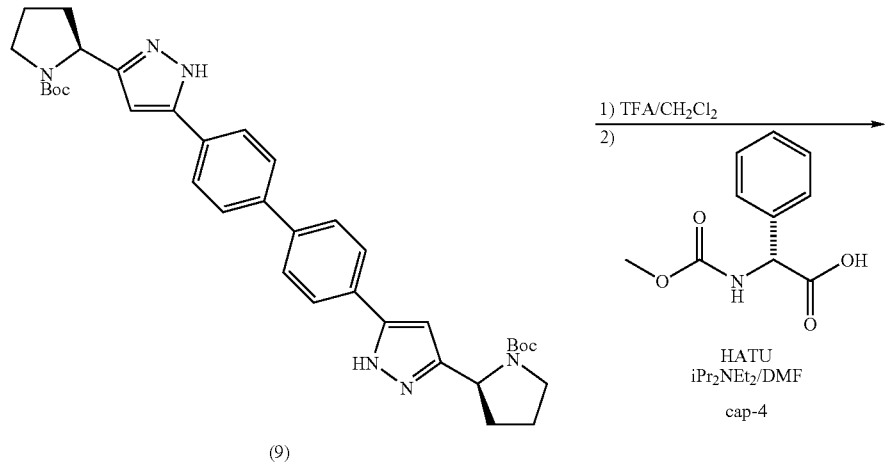

(9)

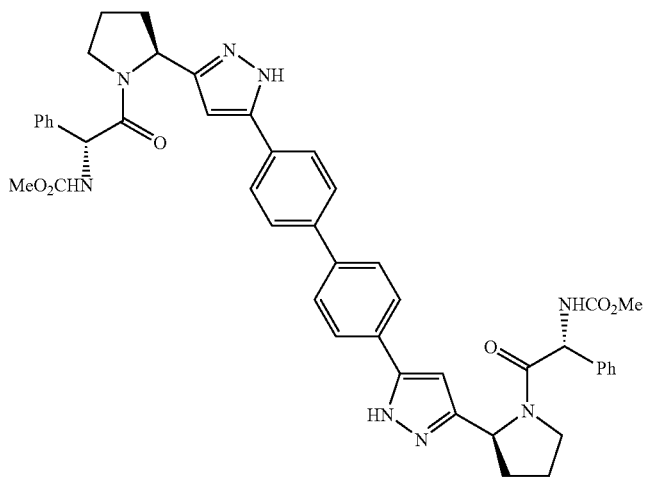

(30)

General Method B: A solution of (2S,2'S)-tert-butyl 2,2'-(5,5'-(biphenyl-4,4'-diyl)bis(1H-pyrazole-5,3-diyl))dipyrrolidine-1-carboxylate (9) (0.080 g, 0.12 mmol) in CH$_2$Cl$_2$ (2.5 mL) was treated with TFA (2.5 mL). The mixture was stirred at room temperature for 1 hour and then the solvents were removed in vacuo. The residue was purified by prep HPLC (CH$_3$CN:H$_2$O:TFA) to afford the TFA salt of 4,4'-bis(3-((S)-pyrrolidin-2-yl)-1H-pyrazol-5-yl)biphenyl (9a) as a colorless solid (0.080 g, 19%).

$^1$H NMR (400 MHz, CD$_3$OD) δ 7.81 (A of app AB quartet, d, J=8.6 Hz, 4H) 7.78 (B of app AB quartet, d, J=8.6 Hz, 4H), 6.80 (s, 2H), 4.78 (app t, J=7.3, 8.1 Hz, 2H), 3.41-3.50 (m, 4H), 2.48-2.55 (m, 2H), 2.14-2.37 (m, 6H). LCMS: Anal. Calcd. for C$_{26}$H$_{28}$N$_6$: 424. found: 425 (M+H)$^+$.

To a solution of the TFA salt of 4,4'-bis(3-((S)-pyrrolidin-2-yl)-1H-pyrazol-5-yl)biphenyl (9a) (0.040 g, 0.0613 mmol), (R)-2-(methoxycarbonylamino)-2-phenylacetic acid cap-4 (0.033 g, 0.158 mmol) and HATU (0.061 g, 0.160 mmol) in DMF (2 mL) at room temperature was added i-Pr$_2$NEt (0.21 mL, 1.23 mmol). The mixture was allowed to stir at room temperature for 4 hours and then the crude reaction mixture was directly purified by preparative HPLC (CH$_3$CN:H$_2$O: TFA) and then repurified by preparative HPLC (CH$_3$CN: H$_2$O:NH$_4$OAc) to give the title compound (30) (0.014 g, 29%) as a white fluffy solid. $^1$H NMR (400 MHz, DMSO-d$_6$) δ 13.05-13.30 (m, 1H), 12.63-12.85 (m, 1H), 7.73-7.81 (m, 9H), 7.30-7.43 (m, 8H), 7.03 (s, br, 1H), 6.93 (m, 0.7H), 6.76 (s, 0.3H), 6.62 (s, 0.7H), 6.43 (s, 0.3H), 5.87 (s, 0.5H), 5.44-5.49 (m, 2H), 5.31 (s, br, 0.5H), 5.05-5.18 (m, 1.7H), 4.71-4.73 (m, 0.3H), 3.91 (s, 1H), 3.71-3.75 (m, 1H), 3.55 (s, 3H), 3.53 (s, 3H), 3.53 (m, obscured, 1H), 3.18 (s, 1H), 1.88-2.01 (m, 8H).

LCMS: Anal. Calcd. for C$_{46}$H$_{46}$N$_8$O$_6$: 809. found: 810 (M+H)$^+$.

The following examples were also prepared using General Method B and the appropriate carboxylic acid:

| Example | Structure | LCMS |
|---|---|---|
| (31) | 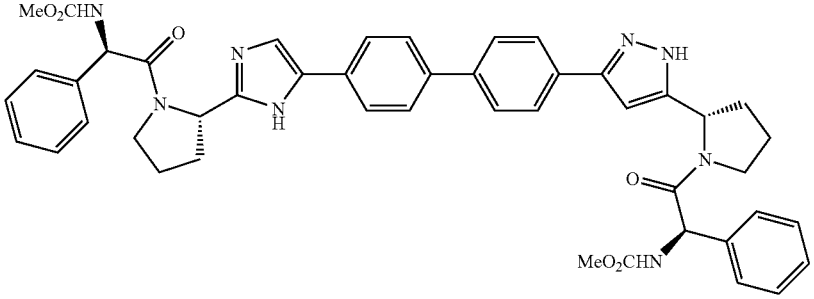<br>from (19) and cap-4 | TFA salt, colorless powder, (0.018 g, 27%) LCMS: Anal. Calcd. for $C_{46}H_{46}N_8O_6$: 806; found: 807 $(M + H)^+$. |
| (32) | 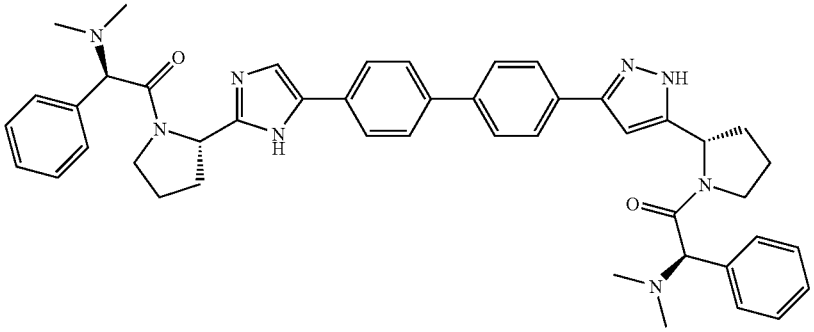<br>from (19) and cap-1 | TFA salt, colorless powder (0.011 g, 14%) LCMS: Anal. Calcd. for $C_{46}H_{50}N_8O_2$: 746; found: 747 $(M + H)^+$. |
| (33) | 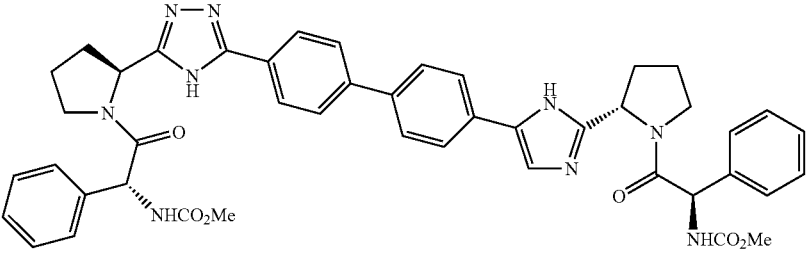<br>from (21) and cap-4 | Colorless powder (0.015 g, 32%) LCMS: Anal. Calcd. for $C_{45}H_{45}N_9O_6$: 807; found: 808 $(M + H)^+$. |
| (34) | 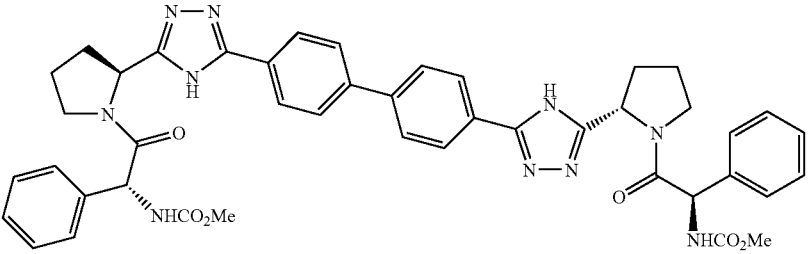<br>from (20) and cap-4 | TFA salt, colorless solid, (0.069 g, 27%) LCMS: Anal. Calcd. for $C_{44}H_{44}N_{10}O_8$: 808; found: 809 $(M + H)^+$. |

US 7,741,347 B2

| Example | Structure | LCMS |
|---|---|---|
| (35) | from (20) and cap-1 | TFA salt, colorless solid, (0.055 g, 33%) LCMS: Anal. Calcd. for $C_{44}H_{48}N_{10}O_2$: 748; found: 749 $(M + H)^+$. |
| (36) | from (29) and cap-4 | LCMS: Anal. Calcd. for $C_{45}H_{44}N_8O_7$: 808; found: 809 $(M + H)^+$. |

Preparation of Intermediate 17: (S)-tert-butyl 2-(5-(4-(4,4,5,5-tetramethyl-1,3,2-dioxaborolan-2-yl)phenyl)-1H-imidazol-2-yl)pyrrolidine-1-carboxylate

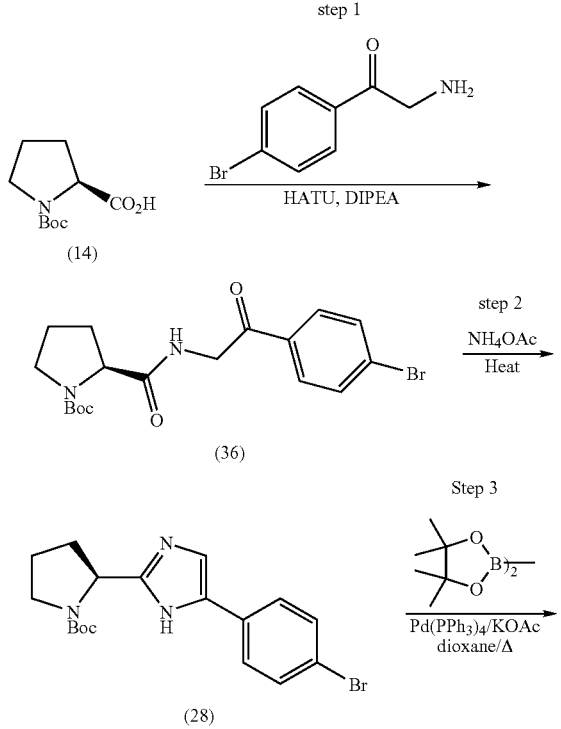

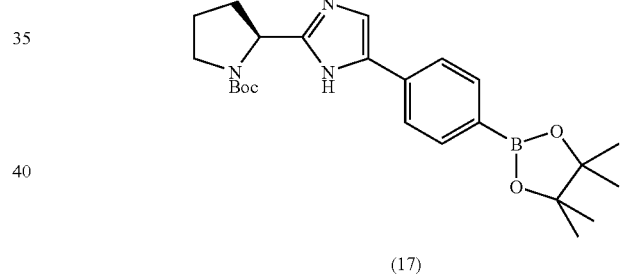

Step 1: N,N-Diisopropylethylamine (18 mL, 103.3 mmol) was added dropwise, over 15 minutes, to a heterogeneous mixture of N-Boc-L-proline 14 (7.139 g, 33.17 mmol), HATU (13.324 g, 35.04 mmol), the HCl salt of 2-amino-1-(4-bromophenyl)ethanone (8.127 g, 32.44 mmol), and DMF (105 mL), and stirred at ambient condition for 55 minutes. Most of the volatile component was removed in vacuo, and the resulting residue was partitioned between ethyl acetate (300 mL) and water (200 mL). The organic layer was washed with water (200 mL) and brine, dried (MgSO$_4$), filtered, and concentrated in vacuo. A silica gel mesh was prepared from the residue and submitted to flash chromatography (silica gel; 50-60% ethyl acetate/hexanes) to provide ketoamide (36) as a white solid (12.8 g). $^1$H NMR (DMSO-d$_6$, δ=2.5 ppm, 400 MHz): δ 8.25-8.14 (m, 1H), 7.92 (br d, J=8.0, 2H), 7.75 (br d, J=8.6, 2H), 4.61 (dd, J=18.3, 5.7, 1H), 4.53 (dd, J=18.1, 5.6, 1H), 4.22-4.12 (m, 1H), 3.43-3.35 (m, 1H), 3.30-3.23 (m, 1H), 2.18-2.20 (m, 1H), 1.90-1.70 (m, 3H), 1.40/1.34 (two app br s, 9H). LC/MS: Anal. Calcd. for $[M+Na]^+$ $C_{18}H_{23}BrN_2NaO_4$: 433.07. found 433.09.

Step 2: A mixture of ketoamide (36) (12.8 g, 31.12 mmol) and NH$_4$OAc (12.0 g, 155.7 mmol) in xylenes (155 mL) was heated in a sealed tube at 140° C. for 2 hours. The volatile component was removed in vacuo, and the residue was partitioned carefully between ethyl acetate and water, whereby enough saturated NaHCO$_3$ solution was added so as to make the pH of the aqueous phase slightly basic after the shaking of the biphasic system. The layers were separated, and the aqueous layer was extracted with an additional ethyl acetate. The combined organic phase was washed with brine, dried (MgSO$_4$), filtered, and concentrated in vacuo. The resulting material was recrystallized from ethyl acetate/hexanes to provide two crops of imidazole (28) as a light-yellow dense solid, weighing 5.85 g. The mother liquor was concentrated in vacuo and submitted to a flash chromatography (silica gel; 30% ethyl acetate/hexanes) to provide an additional 2.23 g of imidazole (28). $^1$H NMR (DMSO-d$_6$, δ=2.5 ppm, 400 MHz): δ 12.17/11.92/11.86 (m, 1H), 7.72-7.46/7.28 (m, 5H), 4.86-4.70 (m, 1H), 3.52 (app br s, 1H), 3.36 (m, 1H), 2.30-1.75 (m, 4H), 1.40/1.15 (app br s, 9H). LC/MS: Anal. Calcd. for [M+H]$^+$ C$_{18}$H$_{23}$BrN$_3$O$_2$: 392.10. found 391.96; HRMS: Anal. Calcd. for [M+H]$^+$ C$_{18}$H$_{23}$BrN$_3$O$_2$: 392.0974. found 392.0959.

The optical purity of the two samples of (28) were assessed using the chiral HPLC conditions noted below (ee>99% for the combined crops; ee=96.7% for the sample from flash chromatography):

Column: Chiralpak AD, 10 um, 4.6×50 mm

Solvent: 2% ethanol/heptane (isocratic)

Flow rate: 1 mL/min

Wavelength: either 220 or 254 nm

Relative retention time: 2.83 minutes (R), 5.34 minutes (S)

Step 3: Pd(Ph$_3$P)$_4$ (469 mg, 0.406 mmol) was added to a pressure tube containing a mixture of bromide (28) (4.008 g, 10.22 mmol), bis(pinacolato)diboron (5.422 g, 21.35 mmol), potassium acetate (2.573 g, 26.21 mmol) and 1,4-dioxane (80 mL). The reaction flask was purged with nitrogen, capped and heated with an oil bath at 80° C. for 16.5 hours. The reaction mixture was filtered and the filtrate was concentrated in vacuo. The crude material was partitioned carefully between CH$_2$Cl$_2$ (150 mL) and an aqueous medium (50 mL water+10 mL saturated NaHCO$_3$ solution). The aqueous layer was extracted with CH$_2$Cl$_2$, and the combined organic phase was dried (MgSO$_4$), filtered, and concentrated in vacuo. The resulting material was purified with flash chromatography (sample was loaded with eluting solvent; 20-35% ethyl acetate/CH$_2$Cl$_2$) to provide boronate (17), contaminated with pinacol, as an off-white dense solid; the relative mole ratio of (17) to pinacol was about 10:1 ($^1$H NMR). The sample weighed 3.925 g after ~2.5 days exposure to high vacuum. $^1$H NMR (DMSO-d$_6$, δ=2.5 ppm, 400 MHz): 12.22/11.94/11.87 (m, 1H), 7.79-7.50/7.34-7.27 (m, 5H), 4.86-4.70 (m, 1H), 3.52 (app br s, 1H), 3.36 (m, 1H), 2.27-1.77 (m, 4H), 1.45-1.10 (m, 21H). LC/MS: Anal. Calcd. for [M+H]$^+$ C$_{24}$H$_{35}$BN$_3$O$_4$: 440.27. found 440.23.

Preparation of Example 37

Step 1: Preparation of(S)-tert-butyl 2-(2-(4-bromophenyl)-2-oxoethylcarbamoyl)pyrrolidine-1-carboxylate

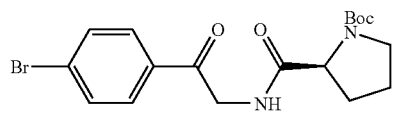

To a solution of 2-amino-1-(4-bromophenyl)ethanone hydrochloride salt (1.10 g, 4.39 mmol), (S)-1-(tert-butoxycarbonyl)pyrrolidine-2-carboxylic acid (1.02 g, 4.73 mmol), and diisopropylethylamine (3.10 mL, 17.4 mmol) in DMF (20 mL) was added 3-(diethoxyphosphoryloxy)-(1,2,3)-benzotriazin-4(3H)-one (DEPBT, 2.0 g, 6.68 mmol) and the solution was allowed to stir for 2 hours. The mixture was poured into H$_2$O-ethyl acetate and the layers were separated. The aqueous phase was extracted twice with ethyl acetate and the combined organic layers were washed (H$_2$O×2, brine), dried (Na$_2$SO$_4$), and filtered. The solvent was removed in vacuo and the residue purified by flash column chromatography (1:1 hexanes:ethyl acetate) to provide (S)-tert-butyl 2-(2-(4-bromophenyl)-2-oxoethylcarbamoyl)pyrrolidine-1-carboxylate (1.02 g, 56%) as a colorless foam. $^1$HNMR (400 MHz, DMSO-d$_6$) δ 8.16-8.21 (m, 1H), 7.90-7.92 (m, 2H), 7.73-7.75 (m, 2H), 4.59 (dd, J=5.7, 18.4 Hz, 1H), 4.51 (dd, J=5.7, 18.4 Hz, 1H), 4.13-4.19 (m, 1H), 3.24-3.27 (m, 2H, partially obscured by H$_2$O), 2.05-2.12 (m, 1H), 1.74-1.81 (m, 3H), 1.39 (s, 3H), 1.33 (3, 6H); LCMS: Anal. Calcd. for C$_{18}$H$_{23}$BrN$_2$O$_4$: 410. found: 411 (M+H)$^+$.

Step 2: Preparation of (S)-tert-butyl 2-(5-(4-bromophenyl)oxazol-2-yl)pyrrolidine-1-carboxylate

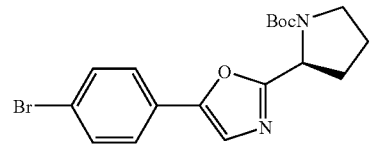

To a solution of the product of Step 1 (1.00 g, 2.43 mmol), PPh$_3$ (1.00 g, 3.71 mmol) and diisopropylethylamine (1.3 mL, 7.28 mmol) in CH$_3$CN (30 mL) was added hexachloroethane (0.812 g, 3.43 mmol) as a solid, portion-wise. The mixture was allowed to stir for 12 hours. TLC (3:1 hexanes:ethyl acetate) indicated the presence of starting material. Therefore, additional PPh$_3$ (0.65 g, 2.43 mmol) and hexachloroethane (0.575 g, 2.43 mmol) were added and stirring continued for 4 hours. The solvent was removed in vacuo, the residue diluted with ethyl acetate-H$_2$O and the layers separated. The aqueous phase was extracted twice with ethyl acetate and the combined organic layers were washed (H$_2$O, brine), dried (Na$_2$SO$_4$), and filtered. The solvent was removed in vacuo and the residue purified by flash column chromatography (3:1 hexanes:ethyl acetate) to provide (S)-tert-butyl 2-(5-(4-bromophenyl)oxazol-2-yl)pyrrolidine-1-carboxylate (0.605 g, 63%). $^1$HNMR (400 MHz, DMSO-d$_6$) δ 7.60-7.68 (m, 5H), 4.80-4.91 (m, 1H), 3.46-3.51 (m, 1H), 3.33-3.39 (m, 1H), 2.18-2.31 (m, 1H), 1.84-1.99 (m, 3H), 1.36 (s, 4H), 1.15 (s, 5H). LCMS: Anal. Calcd. for C$_{18}$H$_{21}$BrN$_2$O$_3$: 392. found: 393 (M+H)$^+$.

Step 3: Preparation of (S)-tert-butyl 2-(5-(4-(4,4,5,5-tetramethyl-1,3,2-dioxaborolan-2-yl)phenyl)oxazol-2-yl)pyrrolidine-1-carboxylate

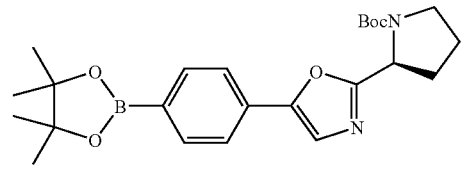

A mixture of the product of Step 2 (0.60 g, 1.53 mmol), bis(pinacolato)diboron (0.98 g, 3.84 mmol), KOAc (0.54 g, 5.48 mmol) and Pd(PPh$_3$)$_4$ (0.10 g, 0.087 mmol) in dioxane (20 ml) was heated at 100° C. for 12 hours. The mixture was poured into H$_2$O-ethyl acetate and the layers separated. The aqueous phase was extracted twice with ethyl acetate and the combined organic layers were washed (H$_2$O, brine), dried ($Na_2SO_4$), and filtered. The solvent was removed in vacuo and the residue purified by flash column chromatography (2:1 hexanes:ethyl acetate) to afford (S)-tert-butyl 2-(5-(4-(4,4,5,5-tetramethyl-1,3,2-dioxaborolan-2-yl)phenyl)oxazol-2-yl)pyrrolidine-1-carboxylate as a light orange oil (742 mg, >100%) which $^1H$ NMR showed to be contaminated with approximately 5-10% triphenylphosphine oxide. The material was used as is in subsequent steps. LCMS: Anal. Calcd. for $C_{24}H_{33}BN_2O_5$: 440. found: 441 $(M+H)^+$.

Step 4: Preparation of (S)-tert-butyl 2-(5-(4'-(5-((S)-1-(tert-butoxycarbonyl)pyrrolidin-2-yl)-1H-imidazol-2-yl)biphenyl-4-yl)oxazol-2-yl)pyrrolidine-1-carboxylate

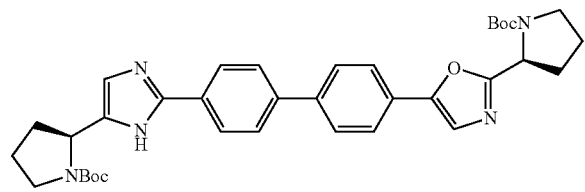

A mixture of the product of Step 3 (0.72 g, 1.63 mmol), the product of Step 2 (0.64 g, 1.63 mmol), $Pd(PPh_3)_4$ (0.094 g, 0.08 mmol), and $NaHCO_3$ (0.41 g, 4.89 mmol) in $DME:H_2O$ (3:1, 20 mL) was heated at 90° C. for 12 hours. The mixture was poured into $H_2O$-ethyl acetate and the layers separated. The aqueous phase was extracted twice with ethyl acetate and the combined organic layers were washed ($H_2O$, brine), dried ($Na_2SO_4$), and filtered. The solvent was removed in vacuo and the residue purified by flash column chromatography (4:1 hexanes:ethyl acetate then ethyl acetate) to provide (S)-tert-butyl 2-(5-(4'-(5-((S)-1-(tert-butoxycarbonyl)pyrrolidin-2-yl)-1H-imidazol-2-yl)biphenyl-4-yl)oxazol-2-yl)pyrrolidine-1-carboxylate as a light yellow glass (431 mg, 42%). $^1$HNMR (400 MHz, DMSO-$d_6$) δ 11.85-12.21 (m, 1H), 7.66-7.84 (m, 9H), 7.01-7.84 (m, 1H), 4.74-5.05 (m, 2H), 3.48-3.54 (m, 2H), 3.35-3.40 (m, 2H), 2.13-2.34 (m, 2H), 1.82-2.02 (m, 6H), 1.39 (s, 6H), 1.18 (s, 6H), 1.16 (s, 3H), 1.14 (s, 3H) LCMS: Anal. Calcd. for $C_{36}H_{43}N_5O_5$: 625. found: 626 $(M+H)^+$.

Step 5: Preparation of 2-((S)-pyrrolidin-2-yl)-5-(4'-(5-((S)-pyrrolidin-2-yl)-1H-imidazol-2-yl)biphenyl-4-yl)oxazole

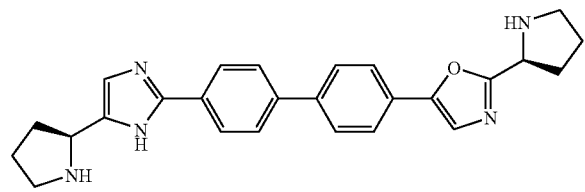

To (S)-tert-butyl 2-(5-(4'-(2-((S)-1-(tert-butoxycarbonyl) pyrrolidin-2-yl)-1H-imidazol-5-yl)biphenyl-4-yl)oxazol-2-yl)pyrrolidine-1-carboxylate (313 mg, 0.500 mmol) in 5 mL methanol was added HCl/dioxane (5 ml, 20.00 mmol) at ambient temperature. After 30 minutes the solution became yellow and heterogenous. After 2 hours, analysis by LC/MS indicated the reaction was complete. The reaction mixture was diluted with 20 mL diethyl ether and filtered providing a light orange solid which was dried under high vacuum to afford 240 mg of the desired product as the tris-HCl salt. $^1$H NMR (500 MHz, DMSO-$d_6$) δ ppm 1.93-2.23 (m, 5H) 2.26-2.47 (m, 6H) 2.63 (s, 1H) 4.81-4.92 (m, 1H) 4.97 (t, J=6.56 Hz, 1H) 7.77-8.01 (m, 10H) LCMS: Anal. Calcd. for $C_{36}H_{43}N_5O_5$: 426. found: 427 $(M+H)^+$.

Step 6: Preparation of Example 37

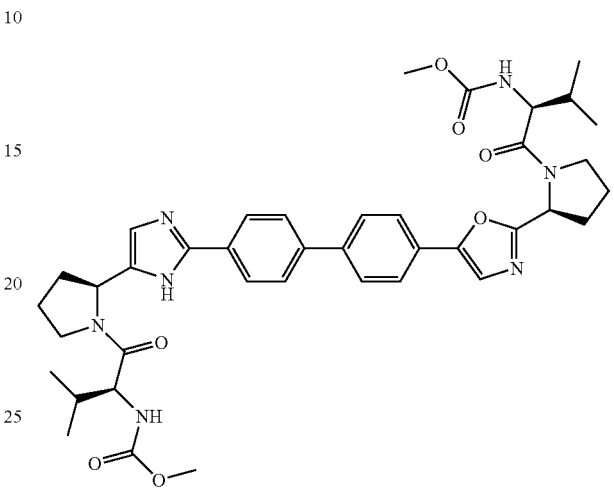

To a solution of the product of Step 5 (50 mg, 0.93 mmol) and Cap-51 (36.0 mg, 0.21 mmol) in DMF (1.5 mL) was added diisopropylethylamine (98 µl, 0.56 mmol) followed by HATU (78 mg, 0.206 mmol). After 16 hours, the reaction mixture was concentrated and purified via preparative HPLC. The fraction containing the desired peak as assayed by LC/MS was passed through an Oasis MCX cartridge (preconditioned with methanol), washed with methanol, and eluted with $NH_3$/methanol. Concentration in vacuo afforded 75 mg of Example 37 as a colorless foam. $^1$H NMR (500 MHz, DMSO-$d_6$) δ ppm 0.75-1.01 (m, 12H) 1.76-2.32 (m, 10H) 3.54 (s, 6H) 3.73-3.93 (m, 4H) 4.00-4.14 (m, J=9.16 Hz, 2H) 5.00-5.21 (m, 2H) 7.22-7.42 (m, J=43.03 Hz, 2H) 7.46-7.96 (m, 10H). LC/MS: Anal. Calcd. For $C_{40}H_{49}N_7O_7$: 740. found: 741 $(M+H)^+$.

Example 38 was prepared in similar fashion starting with 2-((S)-pyrrolidin-2-yl)-5-(4'-(5-((S)-pyrrolidin-2-yl)-1H-imidazol-2-yl)biphenyl-4-yl)oxazole and Cap 52.

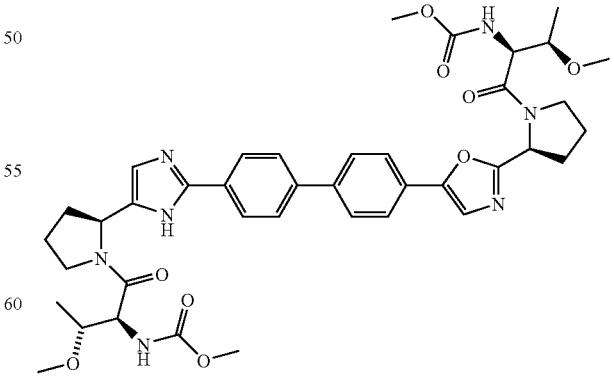

$^1$H NMR (500 MHz, DMSO-$d_6$) δ ppm 1.03-1.16 (m, 6H) 1.90-2.32 (m, 8H) 3.16-3.21 (m, 3H) 3.23 (s, 3H) 3.38-3.52 (m, 3H) 3.79-3.93 (m, 4H) 4.24-4.37 (m, 2H) 5.07 (dd, J=7.17, 3.51 Hz, 1H) 5.15 (dd, J=8.09, 3.51 Hz, 1H) 7.24-

7.30 (m, 1H) 7.36 (d, J=7.63 Hz, 1H) 7.54 (d, J=1.53 Hz, 1H) 7.60-7.64 (m, 1H) 7.67-7.76 (m, 4H) 7.75-7.87 (m, 4H). LC/MS: Anal. Calcd. For $C_{40}H_{49}N_7O_9$: 772. found: 773 $(M+H)^+$.

LC Conditions (Unless Otherwise Noted)

Condition I

Column=Phenomenex-Luna 3.0×50 mm S10

Start % B=0

Final % B=100

Gradient time=2 min

Stop time=3 min

Flow Rate=4 mL/min

Wavelength=220 nm

Solvent A=0.1% TFA in 10% methanol/90% $H_2O$

Solvent B=0.1% TFA in 90% methanol/10% $H_2O$

Condition II

Column=Phenomenex-Luna 4.6×50 mm S10

Start % B=0

Final % B=100

Gradient time=2 min

Stop time=3 min

Flow Rate=5 mL/min

Wavelength=220 nm

Solvent A=0.1% TFA in 10% methanol/90% $H_2O$

Solvent B=0.1% TFA in 90% methanol/10% $H_2O$

Condition III

Column =HPLC XTERRA C18 3.0×50 mm S7

Start % B=0

Final % B=100

Gradient time=3 min

Stop time=4 min

Flow Rate=4 mL/min

Wavelength=220 nm

Solvent A=0.1% TFA in 10% methanol/90% $H_2O$

Solvent B=0.1% TFA in 90% methanol/10% $H_2O$

Synthesis of Common Pyrrolidine Caps

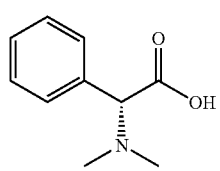

Cap-1

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to $H_2$ (60 psi) for 3 hours. The reaction mixture was filtered through diatomaceous earth (Celite™), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in $H_2O$; λ=589 nm]. $^1H$ NMR (DMSO-$d_6$, δ=2.5 ppm, 500 MHz): δ 7.43-7.34 (m, 5H), 4.14 (s, 1H), 2.43 (s, 6H); LC (Cond. J): RT=0.25; LC/MS: Anal. Calcd. for $[M+H]^+$ $C_{10}H_{14}NO_2$ 180.10. found 180.17; HRMS: Anal. Calcd. for $[M+H]^+$ $C_{10}H_{14}NO_2$ 180.1025. found 180.1017.

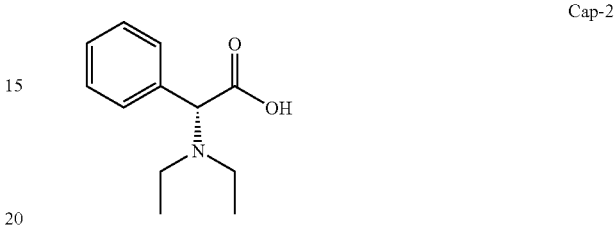

Cap-2

NaBH$_3$CN (6.22 g, 94 mmol) was added in portions over a few minutes to a cooled (ice/water) mixture of (R)-2-Phenylglycine (6.02 g, 39.8 mmol) and methanol (100 mL), and stirred for 5 minutes. Acetaldehyde (10 mL) was added dropwise over 10 minutes and stirring was continued at the same cooled temperature for 45 minutes and at ambient temperature for ~6.5 hours. The reaction mixture was cooled back with ice-water bath, treated with water (3 mL) and then quenched with a dropwise addition of concentrated HCl over ~45 minutes until the pH of the mixture was ~1.5-2.0. The cooling bath was removed and the stirring was continued while adding concentrated HCl in order to maintain the pH of the mixture around 1.5-2.0. The reaction mixture was stirred overnight, filtered to remove the white suspension, and the filtrate was concentrated in vacuo. The crude material was recrystallized from ethanol to afford the HCl salt of Cap-2 as a shining white solid in two crops (crop-1: 4.16 g; crop-2:2.19 g). $^1H$ NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[α]^{25}$-102.21° (c=0.357, $H_2O$); crop-2: $[α]^{25}$-99.7° (c=0.357, $H_2O$). LC (Cond. J): RT=0.43 min; LC/MS: Anal. Calcd. for $[M+H]^+$ $C_{12}H_{18}NO_2$: 208.13. found 208.26

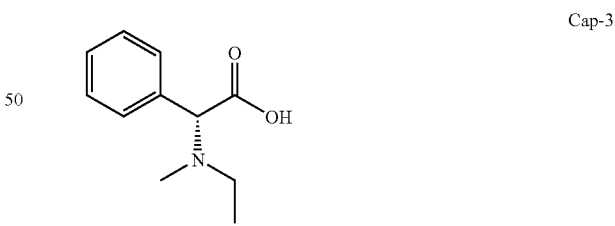

Cap-3

Acetaldehyde (5.0 mL, 89.1 mmol) and a suspension of 10% Pd/C (720 mg) in methanol/$H_2O$ (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (Celite™), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. J): RT=0.39 min; >95% homogeneity index; LC/MS: Anal. Calcd. for [M+H]$^+$ C$_{10}$H$_{14}$NO$_2$: 180.10. found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaceous earth (Celite™) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. J): RT=0.39 min; >95% homogeneity index; LC/MS: Anal. Calcd. for [M+H]$^+$ C$_{11}$H$_{16}$NO$_2$: 194.12. found 194.18; HRMS: Anal. Calcd. for [M+H]$^+$ C$_{11}$H$_{16}$NO$_2$: 194.1180. found 194.1181.

Cap-4

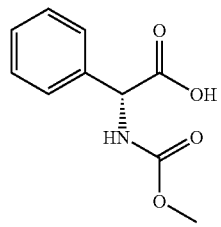

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d$_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. J): RT=1.53 min; ~90% homogeneity index; LC/MS: Anal. Calcd. for [M+Na]$^+$ C$_{14}$H$_{19}$NNaO$_4$: 288.12. found 288.15.

TFA (16 mL) was added dropwise to a cooled (ice/water) CH$_2$Cl$_2$ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H$_2$O; λ=589 nm]. $^1$H NMR (DMSO-d$_6$, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. J): RT=1.01 min; >95% homogeneity index; LC/MS: Anal. Calcd. for [M+H]$^+$ C$_{10}$H$_{12}$NO$_4$ 210.08. found 210.17; HRMS: Anal. Calcd. for [M+H]$^+$ C$_{10}$H$_{12}$NO$_4$ 210.0766. found 210.0756.

Cap-5

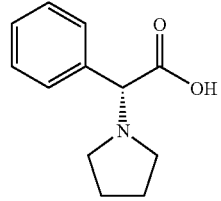

A mixture of (R)-2-phenylglycine (1.0 g, 6.62 mmol), 1,4-dibromobutane (1.57 g, 7.27 mmol) and Na$_2$CO$_3$ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d$_6$, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 minutes (Cond. I); >98% homogeneity index; LC/MS: Anal. Calcd. for [M+H]$^+$ C$_{12}$H$_{16}$NO$_2$: 206.12. found 206.25.

Cap-6

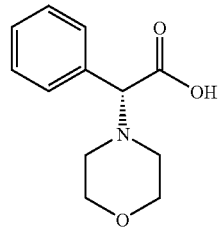

The TFA salt of Cap-6 was synthesized from (R)-2-phenylglycine and 1-bromo-2-(2-bromoethoxy)ethane by using the method of preparation of Cap-5. $^1$H NMR (DMSO-d$_6$, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 minutes (Cond. I); >98%; LC/MS: Anal. Calcd. for [M+H]$^+$ C$_{12}$H$_{16}$NO$_3$: 222.11. found 222.20; HRMS: Anal. Calcd. for [M+H]$^+$ C$_{12}$H$_{16}$NO$_3$: 222.1130. found 222.1121.

Cap-7

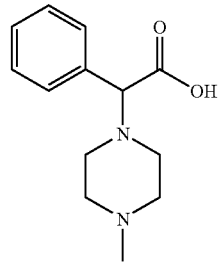

Cap-7a: enantiomer-1
Cap-7b: enantiomer-2

A CH$_2$Cl$_2$ (200 mL) solution of p-toluenesulfonyl chloride (8.65 g, 45.4 mmol) was added dropwise to a cooled (−5° C.)

CH$_2$Cl$_2$ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO$_4$), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d$_6$, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. III); >90% homogeneity index; LC/MS: Anal. Calcd. for [M+H]$^+$ C$_{22}$H$_{20}$NaO$_5$S: 419.09. found 419.04.

A THF (75 mL) solution of benzyl 2-phenyl-2-(tosyloxy)acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO$_4$), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Enantiomer-1 (1.474 g) and enantiomer-2 (2.2149 g) were retrieved as viscous oil. $^1$H NMR (CDCl$_3$, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. III); >98% homogeneity index; LC/MS: Anal. Calcd. for [M+H]$^+$ C$_{20}$H$_{25}$N$_2$O$_2$: 325.19. found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 minutes. Immediately after the completion of the reaction, the catalyst was filtered through diatomaceous earth (Celite™) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. bs, 2H), 2.48-2.32 (m, 6H), 2.19 (s, 3H); RT=0.31 (Cond. II); >90% homogeneity index; LC/MS: Anal. Calcd. for [M+H]$^+$ C$_{13}$H$_{19}$N$_2$O$_2$: 235.14. found 235.15; HRMS: Anal. Calcd. for [M+H]$^+$ C$_{13}$H$_{19}$N$_2$O$_2$: 235.1447. found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

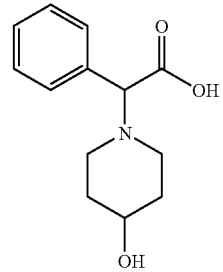

Cap-8

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolyzed according to the preparation of Cap-7 to provide Cap-8: $^1$H NMR (DMSO-d$_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. II); >98% homogeneity index; LC/MS: Anal. Calcd. for [M+H]$^+$ C$_{13}$H$_{18}$NO$_3$: 236.13. found 236.07; HRMS: Calcd. for [M+H]$^+$ C$_{13}$H$_{18}$NO$_3$: 236.1287. found 236.1283.

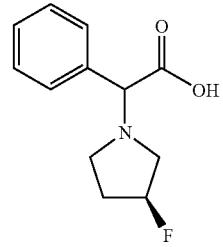

Cap-9

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolyzed according to the preparation of Cap-7 to prepare Caps 9a and 9b. Cap-9a (diastereomer-1; the sample is a TFA salt as a result of purification on a reverse phase HPLC using H$_2$O/methanol/TFA solvent): $^1$H NMR (DMSO-d$_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. I); >95% homogeneity index; LC/MS: Anal. Calcd. for [M+H]+ C12H15FNO2: 224.11. found 224.14; Cap-9b (diastereomer-2): 1H NMR (DMSO-d6, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. I); LC/MS: Anal. Calcd. for [M+H]+ C12H15FNO2: 224.11. found 224.14.

Cap-10

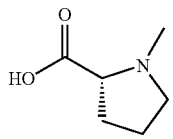

To a solution of D-proline (2.0 g, 17 mmol) and formaldehyde (2.0 mL of 37% wt. in H2O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite™) and concentrated in vacuo to provide Cap-10 as an off-white solid (2.15 g). 1H NMR (DMSO-d6, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. II); >98% homogeneity index; LC/MS: Anal. Calcd. for [M+H]+ C6H12NO2: 130.09. found 129.96.

Cap-11

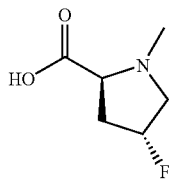

A mixture of (2S,4R)-4-fluoropyrrolidine-2-carboxylic acid (0.50 g, 3.8 mmol), formaldehyde (0.5 mL of 37% wt. in H2O), 12 N HCl (0.25 mL) and 10% Pd/C (50 mg) in methanol (20 mL) was stirred under a balloon of hydrogen for 19 hours. The reaction mixture was filtered through diatomaceous earth (Celite™) and the filtrate was concentrated in vacuo. The residue was recrystallized from isopropanol to provide the HCl salt of Cap-11 as a white solid (337.7 mg). 1H NMR (DMSO-d6, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. II); >98% homogeneity index; LC/MS: Anal. Calcd. for [M+H]+ C6H11FNO2: 148.08. found 148.06.

Cap-12 (same as cap 52)

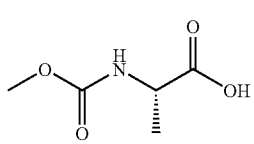

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH~2-3. The resulting solutions was extracted with ethyl acetate (3×100 mL), and the combined organic phase was dried (Na2SO4), filtered, and concentrated in vacuo to provide a colorless oil (2.58 g). 500 mg of this material was purified by a reverse phase HPLC (H2O/methanol/TFA) to provide 150 mg of Cap-12 as a colorless oil. 1HNMR (DMSO-d6, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

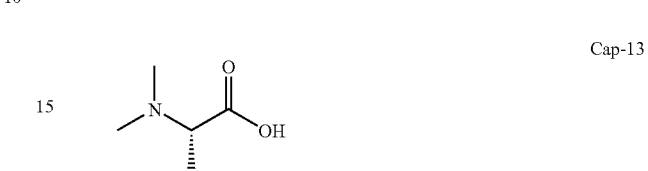

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite™) and the filtrate was concentrated in vacuo to provide the HCl salt of Cap-13 as an oil which solidified upon standing under vacuum (4.4 g; the mass is above theoretical yield). The product was used without further purification. 1H NMR (DMSO-d6, δ=2.5, 500 MHz) δ 12.1 (br s, 1H), 4.06 (q, J=7.4, 1H), 2.76 (s, 6H), 1.46 (d, J=7.3, 3H).

Cap-14

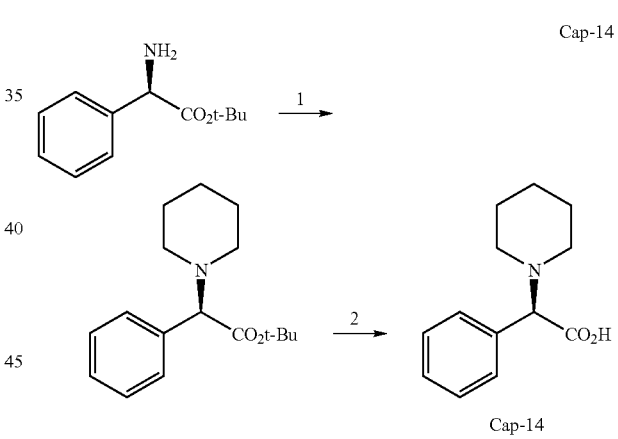

Step 1: A mixture of (R)-(−)-D-phenylglycine tert-butyl ester (3.00 g, 12.3 mmol), NaBH3CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO4), filtered and concentrated to dryness to provide a clear oil. This material was purified by reverse-phase preparative HPLC (Primesphere C-18, 30×100 mm; CH3CN—H2O-0.1% TFA) to give the intermediate ester (2.70 g, 56%) as a clear oil. 1H NMR (400 MHz, CDCl3) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for $C_{17}H_{25}NO_2$: 275. found: 276 $(M+H)^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; $CH_3CN—H_2O$-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$H NMR (DMSO-$d_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for $C_{13}H_{17}NO_2$: 219. found: 220 $(M+H)^+$.

resulting solution was stirred at room temperature under Ar for 18 hours and then it was diluted with ethyl acetate, washed ($H_2O$×2, brine), dried ($Na_2SO_4$), filtered, and concentrated to give a pale yellow oil. Flash chromatography ($SiO_2$/hexane-ethyl acetate, 4:1) of this oil provided the title compound (11.64 g, 73%) as a white solid. $^1$H NMR (400 MHz, $CDCl_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2: (S)-1-Phenylethyl(R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed ($H_2O$×2, brine), dried ($MgSO_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$H NMR ($CD_3OD$) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for $C_{22}H_{27}NO_3$: 353. found: 354 $(M+H)^+$. (S,S)-isomer: $^1$H NMR ($CD_3OD$) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for $C_{22}H_{27}NO_3$: 353. found: 354 $(M+H)^+$.

Step 3: (R)-2-(4-Hydroxy-4-methylpiperidin-1-yl)-2-phenylacetic acid: To a solution of (S)-1-phenylethyl(R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN—H_2O$-0.1% TFA) to give the title compound (as TFA salt) as a pale bluish solid (0.128 g, 98%). LCMS: Anal. Calcd. for $C_{14}H_{19}NO_3$: 249. found: 250 $(M+H)^+$.

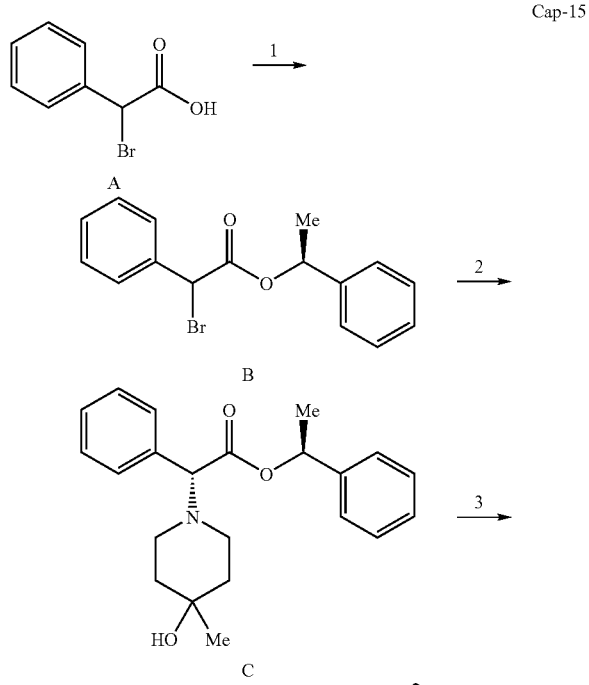

Cap-15

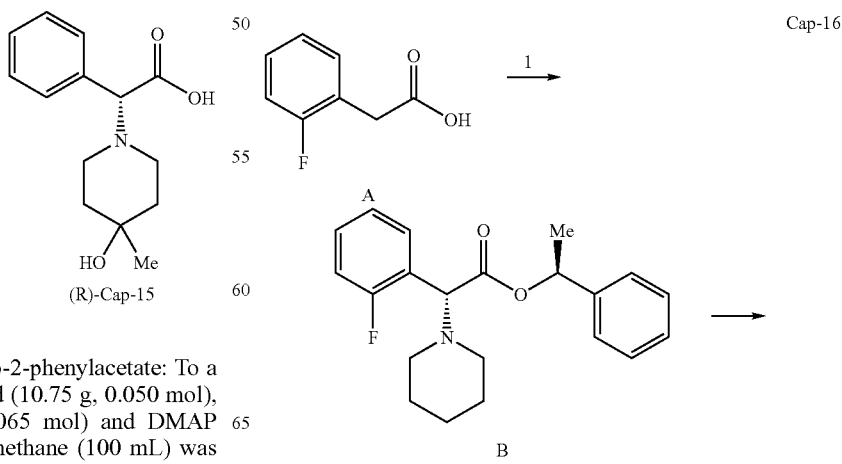

Cap-16

Step 1: (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The

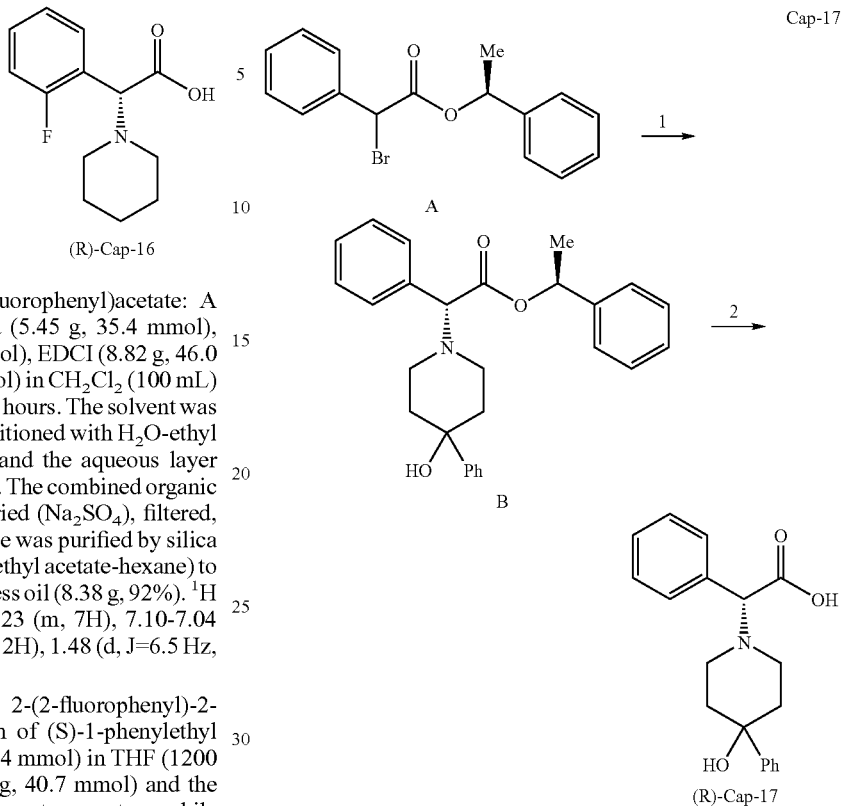

(R)-Cap-16

Step 1: (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in $CH_2Cl_2$ (100 mL) was stirred at room temperature for 12 hours. The solvent was then concentrated and the residue partitioned with $H_2O$-ethyl acetate. The phases were separated and the aqueous layer back-extracted with ethyl acetate (2×). The combined organic phases were washed ($H_2O$, brine), dried ($Na_2SO_4$), filtered, and concentrated in vacuo. The residue was purified by silica gel chromatography (Biotage/0-20% ethyl acetate-hexane) to provide the title compound as a colorless oil (8.38 g, 92%). $^1$H NMR (400 MHz, $CD_3OD$) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2: (R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of $CBr_4$ (13.5 g, 40.7 mmol) in THF (100 mL) was added and the mixture was allowed to warm to −10° C. and stirred at this temperature for 2 hours. The reaction mixture was quenched with saturated aq. $NH_4Cl$ and the layers were separated. The aqueous layer was back-extracted with ethyl acetate (2×) and the combined organic phases were washed ($H_2O$, brine), dried ($Na_2SO_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by $^1$H NMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). $^1$H NMR (400 MHz, $CD_3OD$) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for $C_{21}H_{24}FNO_2$: 341. found: 342 $(M+H)^+$.

Step 3: (R)-2-(2-fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% $Pd(OH)_2/C$ (0.070 g) in ethanol (30 mL) was hydrogenated at room temperature and atmospheric pressure ($H_2$ balloon) for 2 hours. The solution was then purged with Ar, filtered through diatomaceous earth (Celite™), and concentrated in vacuo. This provided the title compound as a colorless solid (0.503 g, 98%). $^1$H NMR (400 MHz, $CD_3OD$) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for $C_{13}H_{16}FNO_2$: 237. found: 238 $(M+H)^+$.

Step 1: (S)-1-Phenylethyl(R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O$×2, brine), dried ($MgSO_4$), filtered and concentrated. The residue was purified on a silica gel column (0-60% ethyl acetate-hexane) to provide an approximately 2:1 mixture of diastereomers, as judged by $^1$H NMR. Separation of these isomers was performed using supercritical fluid chromatography (Chiralcel OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$H NMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415. found: 416 $(M+H)^+$; (S,S)-isomer: $H^1$NMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415. found: 416 $(M+H)^+$.

The following esters were prepared in similar fashion:

| | | |
|---|---|---|
| Intermediate-17a | 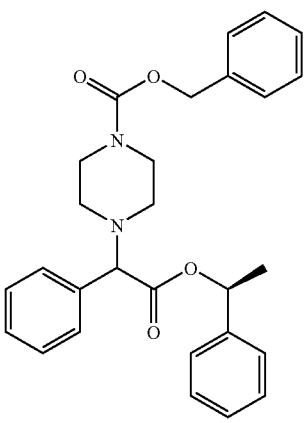 | Diastereomer 1: ¹H NMR (500 MHz, DMSO-d₆) δ ppm 1.36 (d, J = 6.41 Hz, 3H) 2.23-2.51 (m, 4H) 3.35 (s, 4H) 4.25 (s, 1H) 5.05 (s, 2H) 5.82 (d, J = 6.71 Hz, 1H) 7.15-7.52 (m, 15H). LCMS: Anal. Calcd. for: $C_{28}H_{30}N_2O_4$ 458.22; Found: 459.44 (M + H)⁺.<br>Diastereomer 2: ¹H NMR (500 MHz, DMSO-d₆) δ ppm 1.45 (d, J = 6.71 Hz, 3H) 2.27-2.44 (m, 4H) 3.39 (s, 4H) 4.23 (s, 1H) 5.06 (s, 2H) 5.83 (d, J = 6.71 Hz, 1H) 7.12 (dd, J = 6.41, 3.05 Hz, 2H) 7.19-7.27 (m, 3H) 7.27-7.44 (m, 10H). LCMS: Anal. Calcd. for: $C_{28}H_{30}N_2O_4$ 458.22; Found: 459.44 (M + H)⁺. |
| Intermediate-17b | 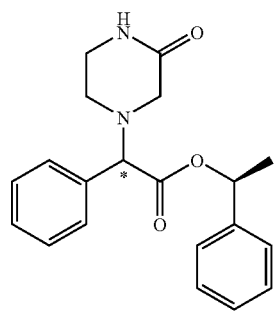 | Diasteromer 1: RT = 11.76 minutes (Cond'n II); LCMS: Anal. Calcd. for: $C_{20}H_{22}N_2O_3$ 338.16 Found: 339.39 (M + H)⁺;<br>Diastereomer 2: RT = 10.05 minutes (Cond'n II); LCMS: Anal. Calcd. for: $C_{20}H_{22}N_2O_3$ 338.16; Found: 339.39 (M + H)⁺. |
| Intermediate-17c | 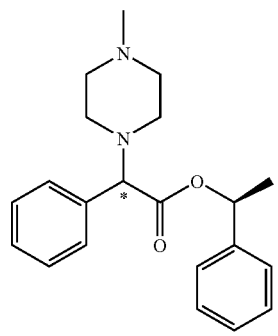 | Diastereomer 1: $T_R$ = 4.55 minutes (Cond'n I); LCMS: Anal. Calcd. for: $C_{21}H_{26}N_2O_2$ 338.20 Found: 339.45 (M + H)⁺;<br>Diastereomer 2: $T_R$ = 6.00 minutes (Cond'n I); LCMS: Anal. Calcd. for: $C_{21}H_{26}N_2O_2$ 338.20 Found: 339.45 (M + H)⁺. |
| Intermediate-17d | 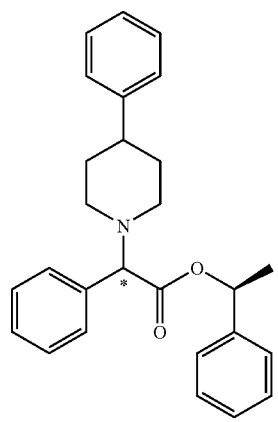 | Diastereomer 1: RT = 7.19 minutes (Cond'n I); LCMS: Anal. Calcd. for: $C_{27}H_{29}NO_2$ 399.22 Found: 400.48 (M + H)⁺;<br>Diastereomer 2: RT = 9.76 minutes (Cond'n I); LCMS: Anal. Calcd. for: $C_{27}H_{29}NO_2$ 399.22 Found: 400.48 (M + H)⁺. |

Chiral SFC Conditions for Determining Retention Time

Condition I

Column: Chiralpak AD-H Column, 4.62×50 mm, 5 μm

Solvents: 90% CO2-10% methanol with 0.1% DEA

Temp: 35° C.

Pressure: 150 bar

Flow rate: 2.0 mL/min.

UV monitored (220 nm

Injection: 1.0 mg/3 mL methanol

Condition II

Column: Chiralcel OD-H Column, 4.62×50 mm, 5 μm

Solvents: 90% CO2-10% methanol with 0.1% DEA

Temp: 35° C.

Pressure: 150 bar

Flow rate: 2.0 mL/min.

UV monitored @220 nm

Injection: 1.0 mg/mL methanol

Cap 17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311.15. found: 312 $(M+H)^+$.

The following carboxylic acids were prepared in optically pure form in a similar fashion:

| | | |
|---|---|---|
| Cap-17a | 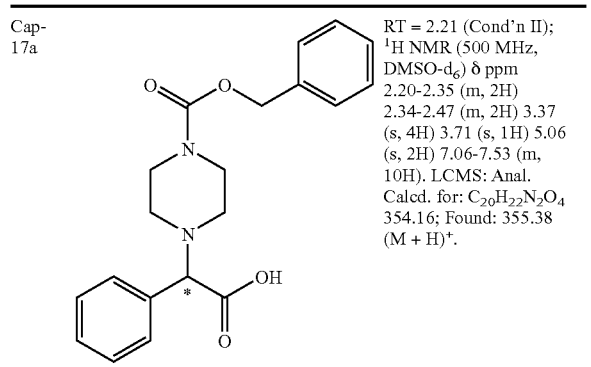 | RT = 2.21 (Cond'n II); $^1$H NMR (500 MHz, DMSO-d$_6$) δ ppm 2.20-2.35 (m, 2H) 2.34-2.47 (m, 2H) 3.37 (s, 4H) 3.71 (s, 1H) 5.06 (s, 2H) 7.06-7.53 (m, 10H). LCMS: Anal. Calcd. for: $C_{20}H_{22}N_2O_4$ 354.16; Found: 355.38 $(M + H)^+$. |
| Cap-17b | 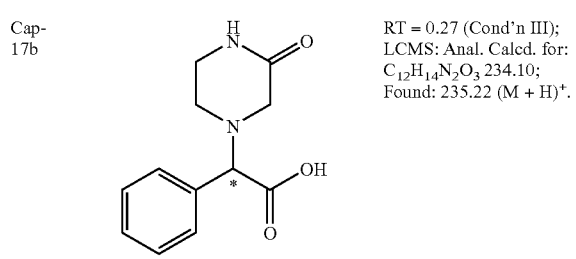 | RT = 0.27 (Cond'n III); LCMS: Anal. Calcd. for: $C_{12}H_{14}N_2O_3$ 234.10; Found: 235.22 $(M + H)^+$. |
| Cap-17c | 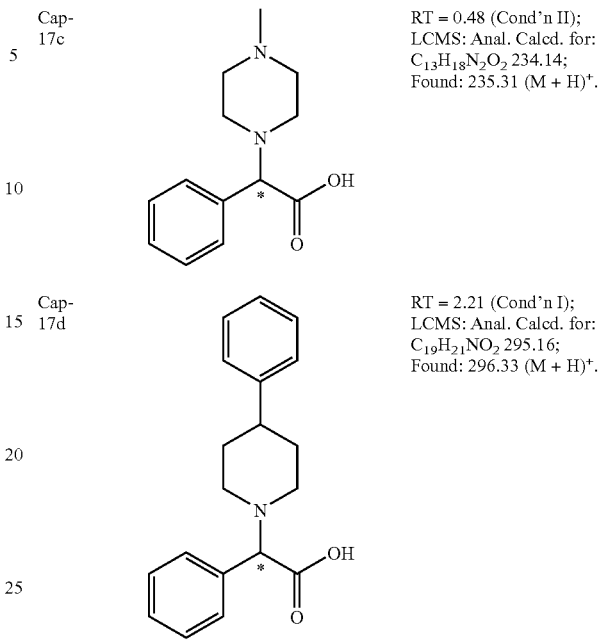 | RT = 0.48 (Cond'n II); LCMS: Anal. Calcd. for: $C_{13}H_{18}N_2O_2$ 234.14; Found: 235.31 $(M + H)^+$. |
| Cap-17d | | RT = 2.21 (Cond'n I); LCMS: Anal. Calcd. for: $C_{19}H_{21}NO_2$ 295.16; Found: 296.33 $(M + H)^+$. |

LCMS Conditions for Determining Retention Time

Condition I

Column: Phenomenex-Luna 4.6×50 mm S10

Start % B=0

Final % B=100

Gradient Time=4 min

Flow Rate=4 mL/min

Wavelength=220

Solvent A=10% methanol-90% $H_2O$-0.1% TFA

Solvent B=90% methanol-10% $H_2O$-0.1% TFA

Condition II

Column: Waters-Sunfire 4.6×50 mm S5

Start % B=0

Final % B=100

Gradient Time=2 min

Flow Rate=4 mL/min

Wavelength=220

Solvent A=10% methanol-90% $H_2O$-0.1% TFA

Solvent B=90% methanol-10% $H_2O$-0.1% TFA

Condition III

Column: Phenomenex 10μ 3.0×50 mm

Start % B=0

Final % B=100

Gradient Time=2 min

Flow Rate=4 mL/min

Wavelength=220

Solvent A=10% methanol-90% H₂O-0.1% TFA
Solvent B=90% methanol-10% H₂O-0.1% TFA

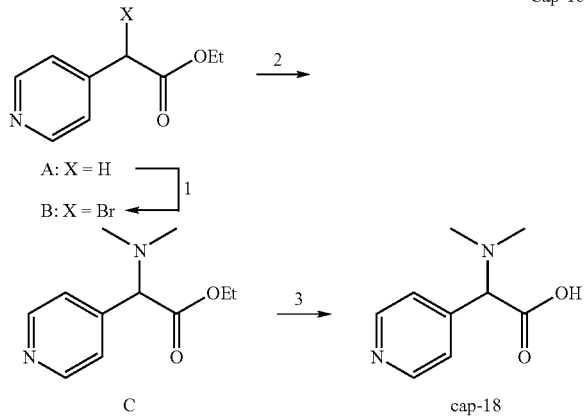

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added CBr₄ (2.21 g, 6.66 mmol) and stirring was continued at −78° C. for 2 hours. The reaction mixture was then quenched with sat. aq. NH₄Cl and the phases were separated. The organic phase was washed (brine), dried (Na₂SO₄), filtered, and concentrated in vacuo. The resulting yellow oil was immediately purified by flash chromatography (SiO₂/hexane-ethyl acetate, 1:1) to provide the title compound (1.40 g, 95%) as a somewhat unstable yellow oil. ¹H NMR (400 MHz, CDCl₃) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for C₉H₁₀BrNO₂: 242, 244. found: 243, 245 (M+H)⁺.

Step 2; (R,S)-Ethyl 2-(4-pyridyl)-2-(N,N-dimethylamino)acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by thin layer chromatography) the volatiles were removed in vacuo and the residue was purified by flash chromatography (Biotage, 40+M SiO₂ column; 50%-100% ethyl acetate-hexane) to provide the title compound (0.539 g, 31%) as a light yellow oil. ¹H NMR (400 MHz, CDCl₃) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for C₁₁H₁₆N₂O₂: 208. found: 209 (M+H)⁺.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H₂O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. ¹H NMR (400 MHz, DMSO-d₆) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above;

| | | |
|---|---|---|
| Cap-19 | 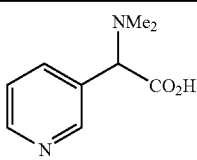 | LCMS: Anal. Calcd. for C₉H₁₂N₂O₂: 180; found: 181 (M + H)⁺. |
| Cap-20 | 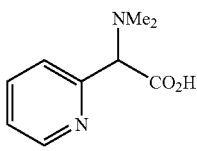 | LCMS: no ionization. ¹H NMR (400 MHz, CD₃OD) δ 8.55 (d, J = 4.3 Hz, 1H), 7.84 (app t, J = 5.3 Hz, 1H), 7.61 (d, J = 7.8 Hz, 1H), 7.37 (app t, J = 5.3 Hz, 1H), 4.35 (s, 1H), 2.60 (s, 6H). |
| Cap-21 | 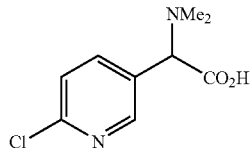 | LCMS: Anal. Calcd. for C₉H₁₁ClN₂O₂: 214, 216; found: 215, 217 (M + H)⁺. |
| Cap-22 | 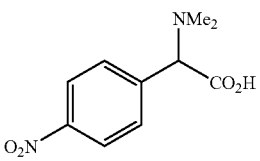 | LCMS: Anal. Calcd. for C₁₀H₁₂N₂O₄: 224; found: 225 (M + H)⁺. |

| | | |
|---|---|---|
| Cap-23 | 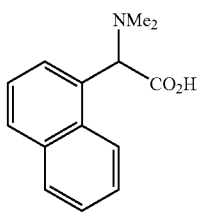 | LCMS: Anal. Calcd. for $C_{14}H_{15}NO_2$: 229; found: 230 $(M + H)^+$. |
| Cap-24 | 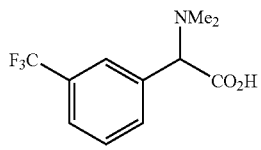 | LCMS: Anal. Calcd. for $C_{11}H_{12}F_3NO_2$: 247; found: 248 $(M + H)^+$. |
| Cap-25 | 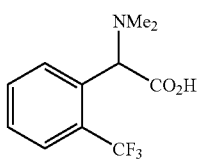 | LCMS: Anal. Calcd. for $C_{11}H_{12}F_3NO_2$: 247; found: 248 $(M + H)^+$. |
| Cap-26 | 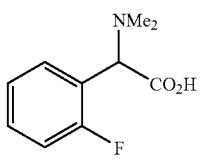 | LCMS: Anal. Calcd. for $C_{10}H_{12}FNO_2$: 197; found: 198 $(M + H)^+$. |
| Cap-27 | 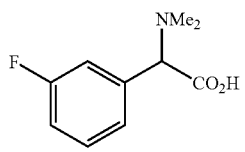 | LCMS: Anal. Calcd. for $C_{10}H_{12}FNO_2$: 247; found: 248 $(M + H)^+$. |
| Cap-28 | 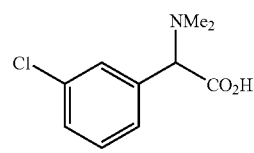 | LCMS: Anal. Calcd. for $C_{10}H_{12}ClNO_2$: 213; found: 214 $(M + H)^+$. |
| Cap-29 | 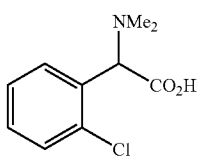 | LCMS: Anal. Calcd. for $C_{10}H_{12}ClNO_2$: 213; found: 214 $(M + H)^+$. |
| Cap-30 | 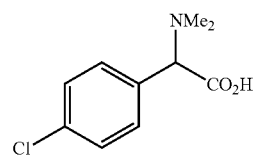 | LCMS: Anal. Calcd. for $C_{10}H_{12}ClNO_2$: 213; found: 214 $(M + H)^+$. |

-continued

| Cap-31 | [structure: 2-methylthiazol-4-yl CH(NMe₂)CO₂H] | LCMS: Anal. Calcd. for C₈H₁₂N₂O₂S: 200; found: 201 (M + H)⁺. |
|---|---|---|
| Cap-32 | [structure: thiophen-2-yl CH(NMe₂)CO₂H] | LCMS: Anal. Calcd. for C₈H₁₁NO₂S: 185; found: 186 (M + H)⁺. |
| Cap-33 | [structure: thiophen-3-yl CH(NMe₂)CO₂H] | LCMS: Anal. Calcd. for C₈H₁₁NO₂S: 185; found: 186 (M + H)⁺. |
| Cap-34 | [structure: benzo[d]isoxazol-3-yl CH(NMe₂)CO₂H] | LCMS: Anal. Calcd. for C₁₁H₁₂N₂O₃: 220; found: 221 (M + H)⁺. |
| Cap-35 | [structure: benzo[b]thiophen-3-yl CH(NMe₂)CO₂H] | LCMS: Anal. Calcd. for C₁₂H₁₃NO₂S: 235; found: 236 (M + H)⁺. |
| Cap-36 | [structure: 2-methylbenzothiazol-5-yl CH(NMe₂)CO₂H] | LCMS: Anal. Calcd. for C₁₂H₁₄N₂O₂S: 250; found: 251 (M + H)⁺. |

Cap-37

[Scheme: Me₂N-CH₂-C(O)-OEt (A) →1→ Me₂N-CH(quinolin-3-yl)-C(O)-OEt (B) →2→ Me₂N-CH(quinolin-3-yl)-C(O)-OH·HCl (cap-37)]

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), K₃PO₄ (1.90 g, 8.95 mmol), Pd(t-Bu₃P)₂ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into H₂O. The mixture was extracted with ethyl acetate (2×) and the combined organic phases were washed (H₂O, brine), dried (Na₂SO₄), filtered, and concentrated in vacuo. The residue was purified first by reverse-phase preparative HPLC (Primesphere C-18, 30×100 mm; CH₃CN—H₂O-5 mM NH₄OAc) and then by flash chromatography (SiO₂/hexane-ethyl acetate, 1:1) to provide the title compound (0.128 g, 17%) as an orange oil. ¹H NMR (400 MHz, CDCl₃) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for C₁₅H₁₈N₂O₂: 258. found: 259 (M+H)⁺.

Step 2; (R,S) 2-(Quinolin-3-yl)-2-(N,N-dimethylamino) acetic acid: A mixture of (R,S)-ethyl 2-(quinolin-3-yl)-2-(N, N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230. found: 231 (M+H)$^+$.

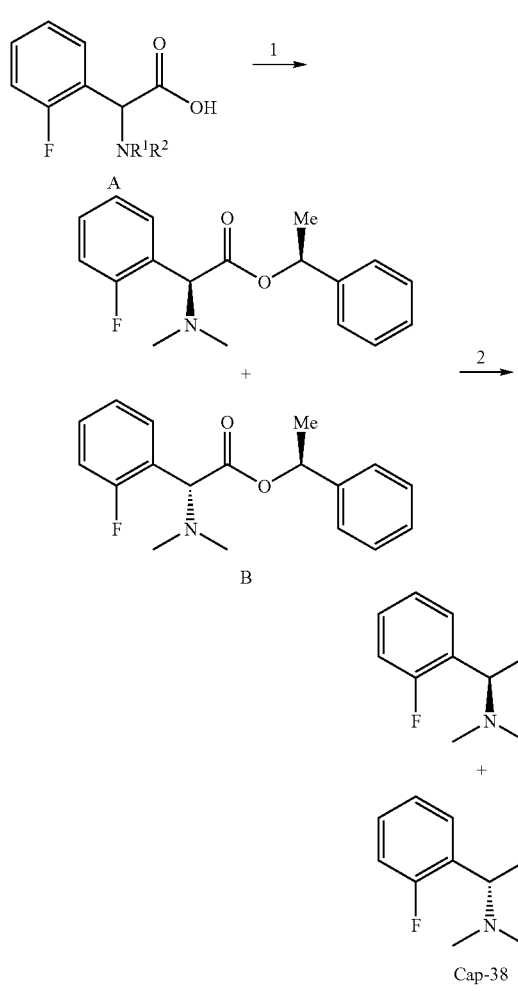

Cap-38

Step 1; (R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2×) and the combined organic phases were washed ($H_2O$, brine), dried ($Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; $CH_3CN$—$H_2O$-0.1% TFA) to give first (S)-1-phenethyl(R)-2-(dimethylamino)-2-(2-fluorophenyl)acetate (0.501 g, 13%) and then (S)-1-phenethyl(S)-2-(dimethylamino)-2-(2-fluorophenyl)-acetate (0.727 g. 18%), both as their TFA salts. (S,R)-isomer: $^1$H NMR (400 MHz, $CD_3OD$) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for $C_{18}H_{20}FNO_2$: 301. found: 302 (M+H)$^+$; (S,S)-isomer: $^1$H NMR (400 MHz, $CD_3OD$) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301. found: 302 (M+H)$^+$.

Step 2; (R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure ($H_2$ balloon) for 4 hours. The solution was then purged with Ar, filtered through diatomaceous earth (Celite™), and concentrated in vacuo. This gave the title compound as a colorless solid (0.503 g, 98%). $^1$H NMR (400 MHz, $CD_3OD$) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197. found: 198 (M+H)$^+$.

The S-isomer could be obtained from (S)—((S)-1-phenylethyl) 2-(dimethylamino)-2-(2-fluorophenyl)acetate TFA salt in similar fashion.

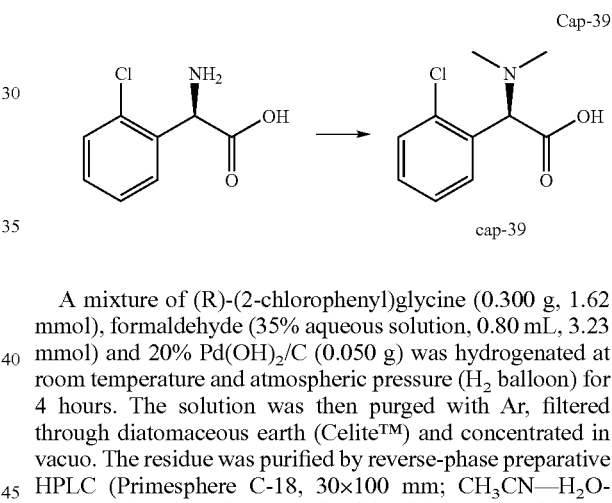

Cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure ($H_2$ balloon) for 4 hours. The solution was then purged with Ar, filtered through diatomaceous earth (Celite™) and concentrated in vacuo. The residue was purified by reverse-phase preparative HPLC (Primesphere C-18, 30×100 mm; $CH_3CN$—$H_2O$-0.1% TFA) to give the TFA salt of the title compound (R)-2-(dimethylamino)-2-(2-chlorophenyl)acetic acid as a colorless oil (0.290 g, 55%). $^1$H NMR (400 MHz, $CD_3OD$) δ 7.59-7.65 (m, 2H), 7.45-7.53 (m, 2H), 5.40 (s, 1H), 2.87 (s, 6H). LCMS: Anal. Calcd. for $C_{10}H_{12}ClNO_2$: 213. found: 214 (M+H)$^+$.

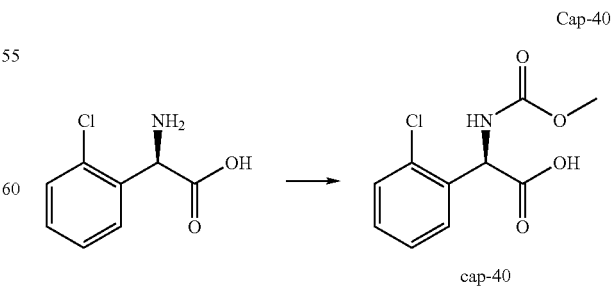

Cap-40

To an ice-cold solution of (R)-(2-chlorophenyl)glycine (1.00 g, 5.38 mmol) and NaOH (0.862 g, 21.6 mmol) in $H_2O$ (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H₂O, brine), dried (Na₂SO₄), filtered, and concentrated in vacuo to give the title compound (R)-2-(methoxycarbonylamino)-2-(2-chlorophenyl)acetic acid as a yellow-orange foam (1.31 g, 96%). ¹H NMR (400 MHz, CD₃OD) δ 7.39-7.43 (m, 2H), 7.29-7.31 (m, 2H), 5.69 (s, 1H), 3.65 (s, 3H). LCMS: Anal. Calcd. for C₁₀H₁₀ClNO₄: 243. found: 244 (M+H)⁺.

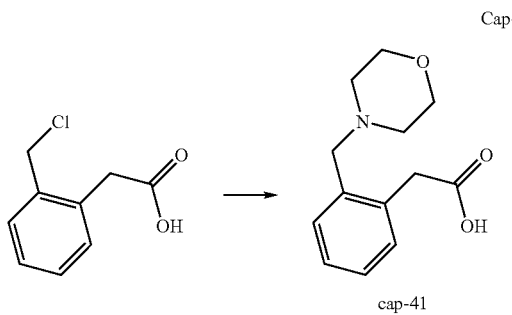

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H₂O (2×). The aqueous phase was lyophilized and the residue was purified by silica gel chromatography (Biotage/0-10% methanol-CH₂Cl₂) to give the title compound 2-(2-(Morpholinomethyl)phenyl)acetic acid as a colorless solid (2.22 g, 87%). ¹H NMR (400 MHz, CD₃OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for C₁₃H₁₇NO₃: 235. found: 236 (M+H)⁺.

The following examples were similarly prepared using the method described for Cap-41:

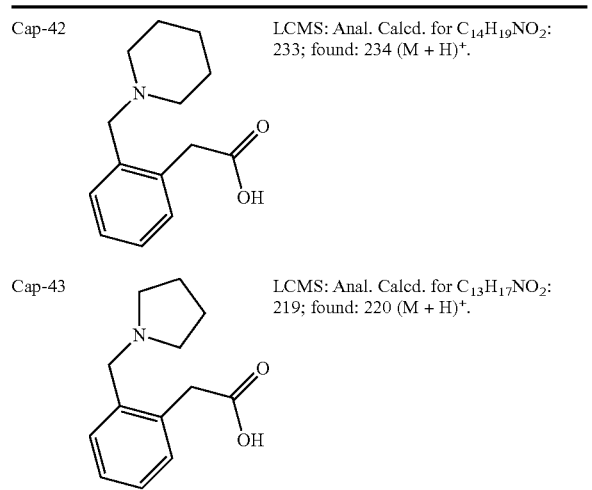

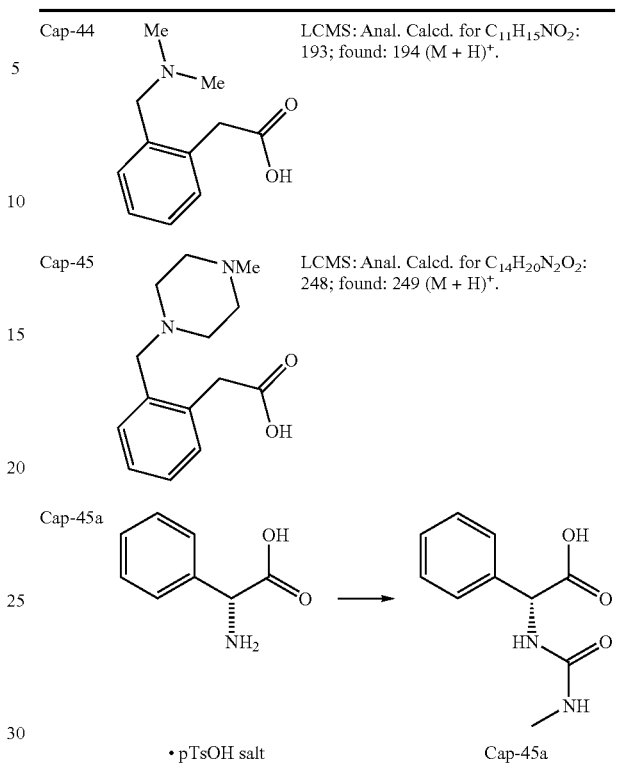

HMDS (1.85 mL, 8.77 mmol) was added to a suspension of (R)-2-amino-2-phenylacetic acid p-toluenesulfonate (2.83 g, 8.77 mmol) in CH₂Cl₂ (10 mL) and the mixture was stirred at room temperature for 30 minutes. Methyl isocyanate (0.5 g, 8.77 mmol) was added in one portion stirring continued for 30 minutes. The reaction was quenched by addition of H₂O (5 mL) and the resulting precipitate was filtered, washed with H₂O and n-hexanes, and dried under vacuum. (R)-2-(3-methylureido)-2-phenylacetic acid (1.5 g; 82%) was recovered as a white solid and it was used without further purification. ¹H NMR (500 MHz, DMSO-d₆) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for C₁₀H₁₂N₂O₃ 208.08 found 209.121 (M+H)⁺; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

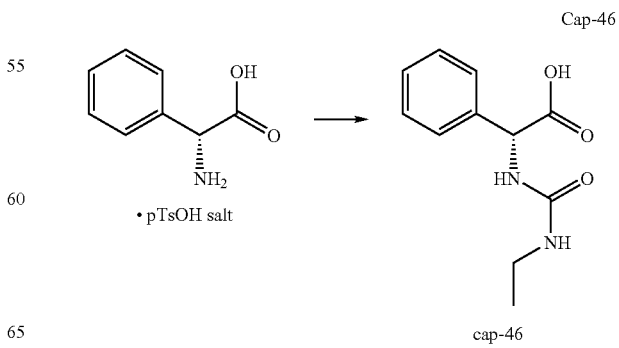

The desired product was prepared according to the method described for Cap-45a. $^1$H NMR (500 MHz, DMSO-$d_6$) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for $C_{11}H_{14}N_2O_3$ 222.10 found 223.15 (M+H)$^+$.

HPLC XTERRA C-18 3.0×506 mm, 0 to 100% B over 2 minutes, 1 minute hold time, A=90% water, 10% methanol, 0.2% $H_3PO_4$, B=10% water, 90% methanol, 0.2% $H_3PO_4$, RT=0.87 min, 90% homogeneity index.

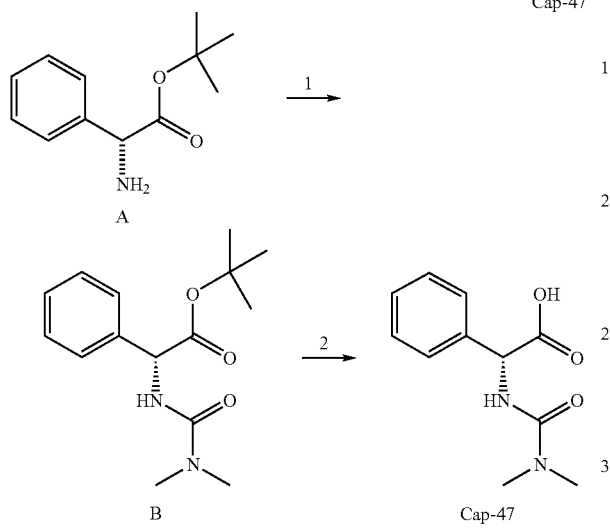

Cap-47

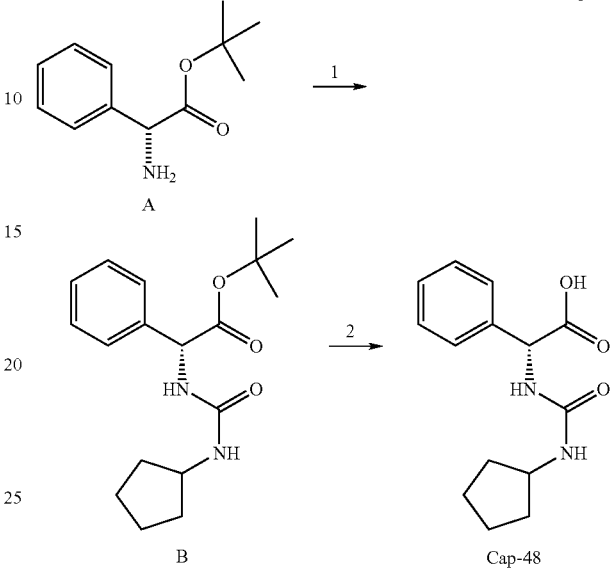

Cap-48

A=90% water, 10% methanol, 0.2% $H_3PO_4$, B=10% water, 90% methanol, 0.2% $H_3PO_4$, RT=0.75 min, 93% homogeneity index.

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with $H_2O$, 1N aq. HCl and brine, dried (MgSO$_4$), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-$d_6$) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for $C_{15}H_{22}N_2O_3$ 278.16 found 279.23 (M+H)$^+$; HPLC Phenomenex LUNA C-18 4.6×50 mm, 0 to 100% B over 4 minutes, 1 minute hold time, A=90% water, 10% methanol, 0.1% TFA, B=10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in $CH_2Cl_2$ (250 mL) was added TFA (15 mL) dropwise and the resulting solution was stirred at rt for 3 hours. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. $^1$H NMR (500 MHz, DMSO-$d_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24. found: 223.21 (M+H)$^+$. HPLC XTERRA C-18 3.0× 50 mm, 0 to 100% B over 2 minutes, 1 minute hold time, Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with $H_2O$ and brine, dried (MgSO$_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, $CD_3Cl$-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)$^+$; HPLC XTERRA C-18 3.0×50 mm, 0 to 100% B over 4 minutes, 1 minute hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in $CH_2Cl_2$ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-$d_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31. found: 263.15 (M+H)$^+$. HPLC XTERRA C-18 3.0×50 mm, 0 to 100% B over 2 minutes, 1 minute hold time, A=90% water, 10% methanol, 0.2% $H_3PO_4$, B=10% water, 90% methanol, 0.2% $H_3PO_4$, RT=1.24 min, 100% homogeneity index.

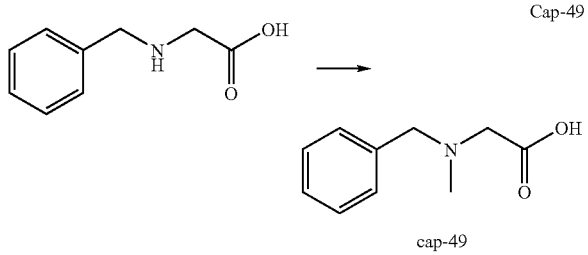

Cap-49 cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1$H NMR (300 MHz, DMSO-$d_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 175.05. Found: 180.20 (M+H)$^+$.

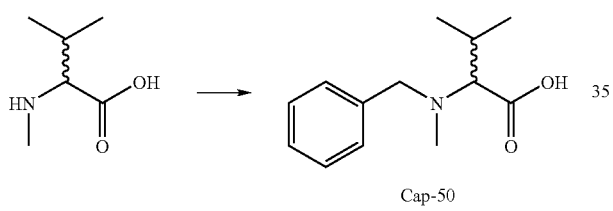

Cap-50

Cap-50

To a stirred solution of 3-methyl-2-(methylamino)butanoic acid (0.50 g, 3.81 mmol) in water (30 mL) was added $K_2CO_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.14. Found: 222.28 (M+H)$^+$.

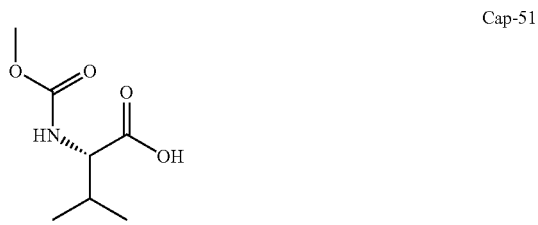

Cap-51

$Na_2CO_3$ (1.83 g, 17.2 mmol) was added to NaOH (33 mL of 1M/$H_2O$, 33 mmol) solution of L-valine (3.9 g, 33.29 mmol) and the resulting solution was cooled with ice-water bath. Methyl chloroformate (2.8 mL, 36.1 mmol) was added dropwise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with $CH_2Cl_2$ (50 mL, 3×). The organic phase was dried ($MgSO_4$) and evaporated in vacuo to afford Cap-51 as a white solid (6 g). $^1$H NMR for the dominant rotamer (DMSO-$d_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ $C_7H_{14}NO_4$: 176.0923. found 176.0922

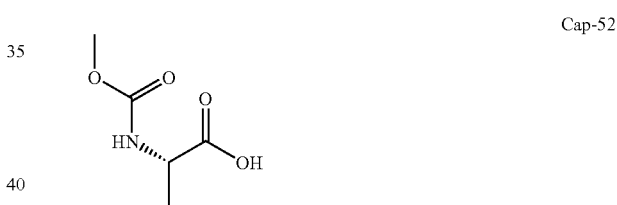

Cap-52

Cap-52 was synthesized from L-alanine according to the procedure described for the synthesis of Cap-51. For characterization purposes, a portion of the crude material was purified by a reverse phase HPLC ($H_2O$/methanol/TFA) to afford Cap-52 as a colorless viscous oil. $^1$H NMR (DMSO-$d_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R)<br>Cap-53b: (S) | 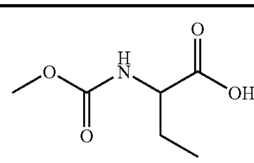 | $^1$H NMR (DMSO-$d_6$, δ = 2.5 ppm, 500 MHz):<br>δ 12.51 (br s, 1H), 7.4 (d, J = 7.9, 0.9H), 7.06 (app s, 0.1H), 3.86-3.82 (m, 1H), 3.53 (s, 3H), 1.75-1.67 (m, 1H), 1.62-1.54 (m, 1H), 0.88 (d, J = 7.3, 3H). RT = 0.77 minutes (Cond. 2); LC/MS: Anal. Calcd. for [M + Na]$^+$ $C_6H_{11}NNaO_4$: 184.06; found 184.07. HRMS Calcd. for [M + Na]$^+$ $C_6H_{11}NNaO_4$: 184.0586; found 184.0592. |

-continued

| Cap | Structure | Data |
|---|---|---|
| Cap-54a: (R) Cap-54b: (S) | | ¹H NMR (DMSO-d₆, δ = 2.5 ppm, 500 MHz): δ 12.48 (s, 1H), 7.58 (d, J = 7.6, 0.9H), 7.25 (app s, 0.1H), 3.52 (s, 3H), 3.36-3.33 (m, 1H), 1.10-1.01 (m, 1H), 0.54-0.49 (m, 1H), 0.46-0.40 (m, 1H), 0.39-0.35 (m, 1H), 0.31-0.21 (m, 1H). HRMS Calcd. for [M + H]⁺ C₇H₁₂NO₄: 174.0766; found 174.0771 |
| Cap-55 | 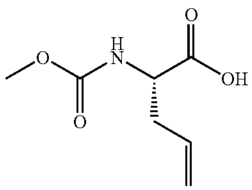 | ¹H NMR (DMSO-d₆, δ = 2.5 ppm, 500 MHz): δ 12.62 (s, 1H), 7.42 (d, J = 8.2, 0.9H), 7.07 (app s, 0.1H), 5.80-5.72 (m, 1H), 5.10 (d, J = 17.1, 1H), 5.04 (d, J = 10.4, 1H), 4.01-3.96 (m, 1H), 3.53 (s, 3H), 2.47-2.42 (m, 1H), 2.35-2.29 (m, 1H). |
| Cap-56 | 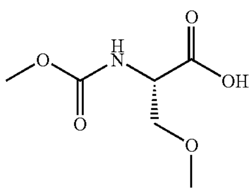 | ¹H NMR (DMSO-d₆, δ = 2.5 ppm, 500 MHz): δ 12.75 (s, 1H), 7.38 (d, J = 8.3, 0.9H), 6.96 (app s, 0.1H), 4.20-4.16 (m, 1H), 3.60-3.55 (m, 2H), 3.54 (s, 3H), 3.24 (s, 3H). |
| Cap-57 | 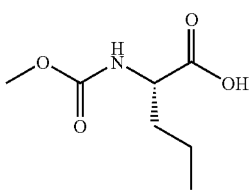 | ¹H NMR (DMSO-d₆, δ = 2.5 ppm, 500 MHz): δ 12.50 (s, 1H), 8.02 (d, J = 7.7, 0.08H), 7.40 (d, J = 7.9, 0.76H), 7.19 (d, J = 8.2, 0.07H), 7.07 (d, J = 6.7, 0.09H), 4.21-4.12 (m, 0.08H), 4.06-3.97 (m, 0.07H), 3.96-3.80 (m, 0.85H), 3.53 (s, 3H), 1.69-1.51 (m, 2H), 1.39-1.26 (m, 2H), 0.85 (t, J = 7.4, 3H). LC (Cond. 2): RT = 1.39 LC/MS: Anal. Calcd. for [M + H]⁺ C₇H₁₄NO₄: 176.09; found 176.06. |
| Cap-58 | 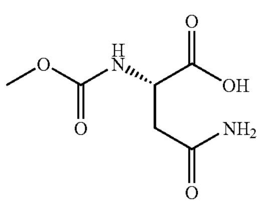 | ¹H NMR (DMSO-d₆, δ = 2.5 ppm, 500 MHz): δ 12.63 (bs, 1H), 7.35 (s, 1H), 7.31 (d, J = 8.2, 1H), 6.92 (s, 1H), 4.33-4.29 (m, 1H), 3.54 (s, 3H), 2.54 (dd, J = 15.5, 5.4, 1H), 2.43 (dd, J = 15.6, 8.0, 1H). RT = 0.16 min (Cond. 2); LC/MS: Anal. Calcd. for [M + H]⁺ C₆H₁₁N₂O₅: 191.07; found 191.14. |
| Cap-59a: (R) Cap-59b: (S) | | ¹H NMR (DMSO-d₆, δ = 2.5 ppm, 400 MHz): δ 12.49 (br s, 1H), 7.40 (d, J = 7.3, 0.89H), 7.04 (br s, 0.11H), 4.00-3.95 (m, 3H), 1.24 (d, J = 7.3, 3H), 1.15 (t, J = 7.2, 3H). HRMS: Anal. Calcd. for [M + H]⁺ C₆H₁₂NO₄: 162.0766; found 162.0771. |
| Cap-60 | 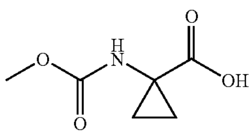 | The crude material was purified with a reverse phase HPLC (H₂O/MeOH/TFA) to afford a colorless viscous oil that crystallized to a white solid upon exposure to high vacuum. ¹H NMR (DMSO-d₆, δ = 2.5 ppm, 400 MHz): δ 12.38 (br s, 1H), 7.74 (s, 0.82H), 7.48 (s, 0.18H), 3.54/3.51 (two s, 3H), 1.30 (m, 2H), 0.98 (m, 2H). HRMS: Anal. Calcd. for [M + H]⁺ C₆H₁₀NO₄: 160.0610; found 160.0604. |
| Cap-61 | 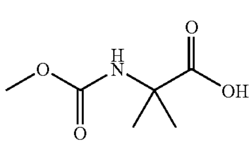 | ¹H NMR (DMSO-d₆, δ = 2.5 ppm, 400 MHz): δ 12.27 (br s, 1H), 7.40 (br s, 1H), 3.50 (s, 3H), 1.32 (s, 6H). HRMS: Anal. Calcd. for [M + H]⁺ C₆H₁₂NO₄: 162.0766; found 162.0765. |

| Cap | Structure | Data |
| --- | --- | --- |
| Cap-62 | 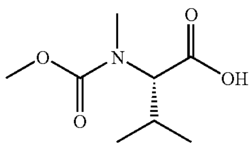 | $^1$H NMR (DMSO-d$_6$, δ = 2.5 ppm, 400 MHz): δ 12.74 (br s, 1H), 4.21 (d, J = 10.3, 0.6H), 4.05 (d, J = 10.0, 0.4H), 3.62/3.60 (two singlets, 3H), 3.0 (s, 3H), 2.14-2.05 (m, 1H), 0.95 (d, J = 6.3, 3H), 0.81 (d, J = 6.6, 3H). LC/MS: Anal. Calcd. for [M − H]$^-$ C$_8$H$_{14}$NO$_4$: 188.09; found 188.05. |
| Cap-63 | 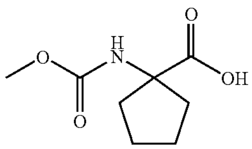 | [Note: the reaction was allowed to run for longer than what was noted for the general procedure.] $^1$H NMR (DMSO-d$_6$, δ = 2.5 ppm, 400 MHz): 12.21 (br s, 1H), 7.42 (br s, 1H), 3.50 (s, 3H), 2.02-1.85 (m, 4H), 1.66-1.58 (m, 4H). LC/MS: Anal. Calcd. for [M + H]$^+$ C$_8$H$_{14}$NO$_4$: 188.09; found 188.19. |
| Cap-64 | 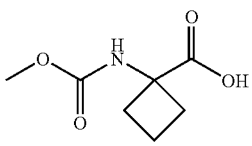 | [Note: the reaction was allowed to run for longer than what was noted for the general procedure.] $^1$H NMR (DMSO-d$_6$, δ = 2.5 ppm, 400 MHz): 12.35 (br s, 1H), 7.77 (s, 0.82H), 7.56/7.52 (overlapping br s, 0.18H), 3.50 (s, 3H), 2.47-2.40 (m, 2H), 2.14-2.07 (m, 2H), 1.93-1.82 (m, 2H). |
| Cap-65 | 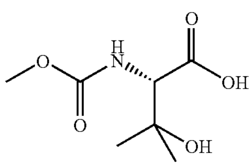 | |

Methyl chloroformate (0.65 mL, 8.39 mmol) was added dropwise over 5 min to a cooled (ice-water) mixture of Na$_2$CO$_3$ (0.449 g, 4.23 mmol), NaOH (8.2 mL of 1M/H$_2$O, 8.2 mmol) and (S)-2-amino-3-hydroxy-3-methylbutanoic acid (1.04 g, 7.81 mmol). The reaction mixture was stirred for 45 min, and then the cooling bath was removed and stirring was continued for an additional 3.75 hr. The reaction mixture was washed with CH$_2$Cl$_2$, and the aqueous phase was cooled with ice-water bath and acidified with concentrated HCl to a pH region of 1-2. The volatile component was removed in vacuo and the residue was taken up in a 2:1 mixture of MeOH/CH$_2$Cl$_2$ (15 mL) and filtered, and the filterate was rotervaped to afford Cap-65 as a white semi-viscous foam (1.236 g). $^1$H NMR (DMSO-d$_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

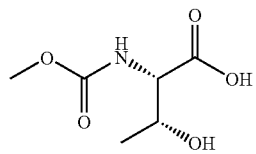
Cap-66

$^1$H NMR (DMSO-d$_6$, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

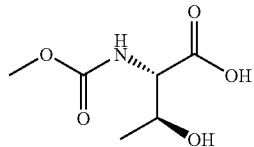
Cap-67

$^1$H NMR (DMSO-d$_6$, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted]

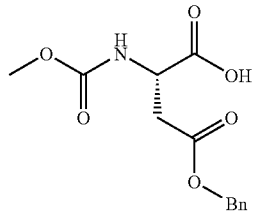
Cap-68

Methyl chloroformate (0.38 ml, 4.9 mmol) was added drop-wise to a mixture of 1N NaOH (aq) (9.0 ml, 9.0 mmol), 1M NaHCO$_3$ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH~1-2, and extracted with ethyl acetate (3×50 ml). The combined organic layers were washed with brine, dried (Na₂SO₄), filtered, and concentrated in vacuo to afford Cap-68 as a light yellow oil (1.37 g; mass is above theoretical yield, and the product was used without further purification). ¹H NMR (DMSO-d₆, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]⁺ C₁₃H₁₆NO₆: 282.10. found 282.12.

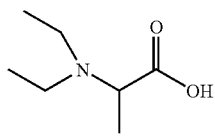

Cap-69a and -69b

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. ¹H NMR (DMSO-d₆, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R)<br>Cap-70b: (S) | 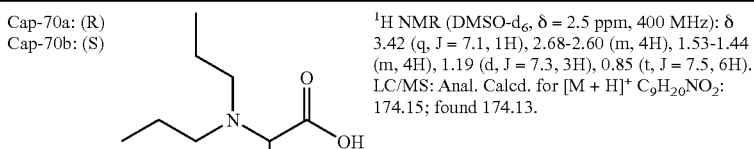 | ¹H NMR (DMSO-d₆, δ = 2.5 ppm, 400 MHz): δ 3.42 (q, J = 7.1, 1H), 2.68-2.60 (m, 4H), 1.53-1.44 (m, 4H), 1.19 (d, J = 7.3, 3H), 0.85 (t, J = 7.5, 6H). LC/MS: Anal. Calcd. for [M + H]⁺ C₉H₂₀NO₂: 174.15; found 174.13. |
| Cap-71a: (R)<br>Cap-71b: (S) | 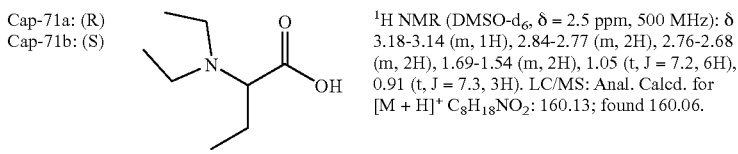 | ¹H NMR (DMSO-d₆, δ = 2.5 ppm, 500 MHz): δ 3.18-3.14 (m, 1H), 2.84-2.77 (m, 2H), 2.76-2.68 (m, 2H), 1.69-1.54 (m, 2H), 1.05 (t, J = 7.2, 6H), 0.91 (t, J = 7.3, 3H). LC/MS: Anal. Calcd. for [M + H]⁺ C₈H₁₈NO₂: 160.13; found 160.06. |
| Cap-72 | 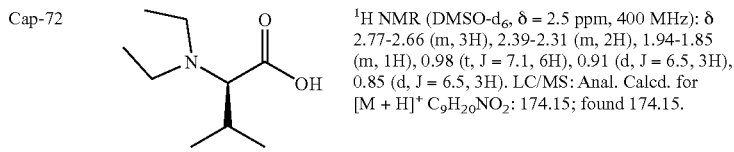 | ¹H NMR (DMSO-d₆, δ = 2.5 ppm, 400 MHz): δ 2.77-2.66 (m, 3H), 2.39-2.31 (m, 2H), 1.94-1.85 (m, 1H), 0.98 (t, J = 7.1, 6H), 0.91 (d, J = 6.5, 3H), 0.85 (d, J = 6.5, 3H). LC/MS: Anal. Calcd. for [M + H]⁺ C₉H₂₀NO₂: 174.15; found 174.15. |
| Cap-73 | 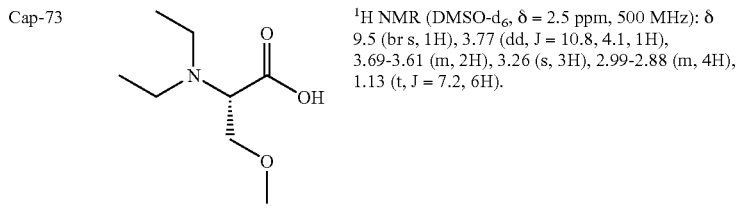 | ¹H NMR (DMSO-d₆, δ = 2.5 ppm, 500 MHz): δ 9.5 (br s, 1H), 3.77 (dd, J = 10.8, 4.1, 1H), 3.69-3.61 (m, 2H), 3.26 (s, 3H), 2.99-2.88 (m, 4H), 1.13 (t, J = 7.2, 6H). |
| Cap-74 | 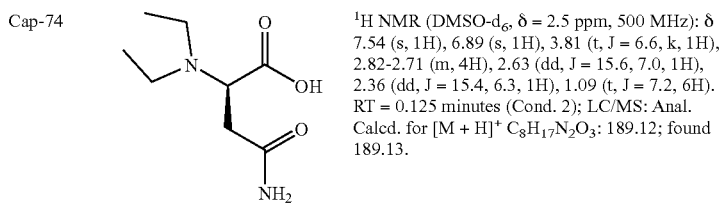 | ¹H NMR (DMSO-d₆, δ = 2.5 ppm, 500 MHz): δ 7.54 (s, 1H), 6.89 (s, 1H), 3.81 (t, J = 6.6, k, 1H), 2.82-2.71 (m, 4H), 2.63 (dd, J = 15.6, 7.0, 1H), 2.36 (dd, J = 15.4, 6.3, 1H), 1.09 (t, J = 7.2, 6H). RT = 0.125 minutes (Cond. 2); LC/MS: Anal. Calcd. for [M + H]⁺ C₈H₁₇N₂O₃: 189.12; found 189.13. |

| | |
|---|---|
| Cap-74x 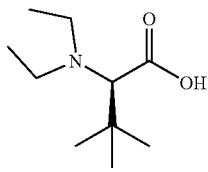 | LC/MS: Anal. Calcd. for [M + H]⁺ C₁₀H₂₂NO₂: 188.17; found 188.21 |
| Cap-75 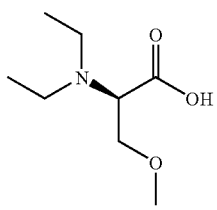 | |
| Cap-75, step a 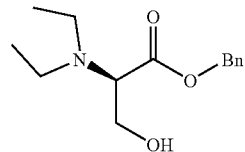 | |

NaBH₃CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H₂O/TFA) to afford the TFA salt of (R)-benzyl 2-(diethylamino)-3-hydroxypropanoate as a colorless viscous oil (1.9 g). ¹H NMR (DMSO-d₆, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]⁺ C₁₄H₂₂NO₃: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 µL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH₃/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

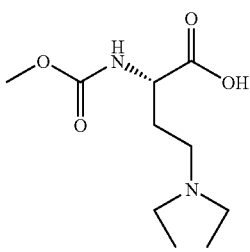

Cap-76

NaCNBH₃ (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute NH₄OH, prepared from 18 ml of NH₄OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na₂CO₃ (0.243 g, 2.29 mmol), NaOH (4.6 mL of 1M/H₂O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with $CH_2Cl_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M $NH_3$/MeOH) to afford impure Cap-76 as an off-white solid (704 mg). $^1$H NMR (MeOH-$d_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ $C_{10}H_{21}N_2O_4$: 233.15. found 233.24.

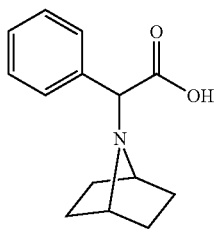

Cap-77a and -77b

Cap-77a: enantiomer-1
Cap-77b: enantiomer-2

The synthesis of Cap-77 was conducted according to the procedure described for Cap-7 by using 7-azabicyclo[2.2.1]heptane for the $SN_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% $CO_2$-10% EtOH at 70 mL/min, and a temperature of 35° C. to provide 124.5 mg of enantiomer-1 and 133.8 mg of enantiomer-2. These benzyl esters were hydrogenolyzed according to the preparation of Cap-7 to provide Cap-77: $^1$H NMR (DMSO-$d_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ $C_{14}H_{18}NO_2$: 232.13. found 232.18. HRMS: Anal. Calcd. for [M+H]$^+$ $C_{14}H_{18}NO_2$: 232.1338. found 232.1340.

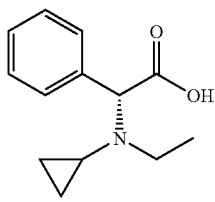

Cap-78

NaCNBH$_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH$_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC ($H_2O$/MeOH/TFA) to afford the TFA salt of Cap-78 as a colorless viscous oil (353 mg). $^1$H NMR (DMSO-$d_6$, δ=2.5 ppm, 400 MHz; after $D_2O$ exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ $C_{13}H_{18}NO_2$: 220.13. found 220.21. HRMS: Anal. Calcd. for [M+H]$^+$ $C_{13}H_{18}NO_2$: 220.1338. found 220.1343.

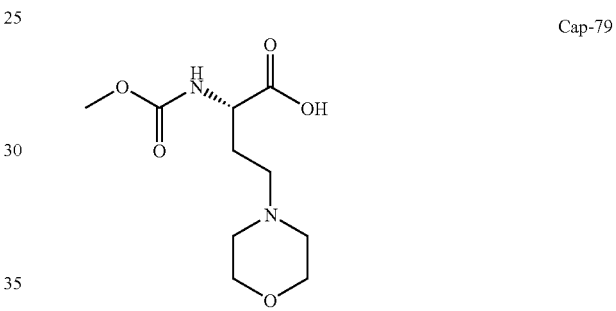

Cap-79

Ozone was bubbled through a cooled (−78° C.) $CH_2Cl_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 µL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N $NH_3$/MeOH elution) and a reverse phase HPLC ($H_2O$/MeOH/TFA) to afford Cap-79 containing unknown amount of morpholine.

In order to consume the morpholine contaminant, the above material was dissolved in $CH_2Cl_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and $H_2O$ (0.5 mL) were added and stirring continued for 1.5 hr. The volatile component was removed in vacuo, and the resultant residue was passed through MCX resin (MeOH wash; 2.0 N $NH_3$/MeOH elution) to afford impure Cap-79 as a brown viscous oil, which was used for the next step without further purification.

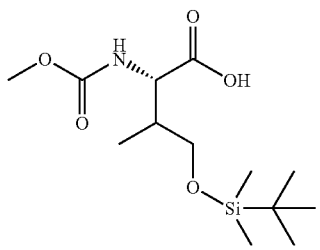

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11. found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20. found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for 1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45. found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45. found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]+ $C_{24}H_{21}NNaO_2$: 378.15. found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]+ $C_{24}H_{21}NNaO_2$: 378.15. found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]+ $C_{37}H_{44}NO_3Si$: 578.31. found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, H), 2.37 (m, 1H), 0.97 (d, J=7.0, 3H), 0.92 (s, 9H), 0.10 (s, 6H). LC/MS: Anal. Calcd. for [M+H]+ $C_{11}H_{26}NO_3Si$: 248.17. found 248.44. (2S,3R)-amino acid isomer: $^1$H NMR (Methanol-d$_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]+ $C_{11}H_{26}NO_3Si$: 248.17. found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]+ $C_{13}H_{27}NNaO_5Si$: 328.16. found 328.46. Cap-80b: $^1$H NMR (CDCl$_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]+ $C_{13}H_{27}NNaO_5Si$: 328.16. found 328.53. The crude products were utilized without further purification.

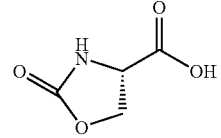

Cap-81

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51 or Cap-13. The samples exhibited similar spectral profiles as that of their enantiomers (i.e., Cap-4, Cap-13, Cap-51 and Cap-52, respectively)

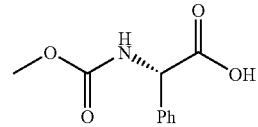

Cap-82

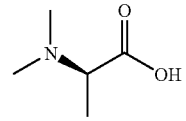

Cap-83

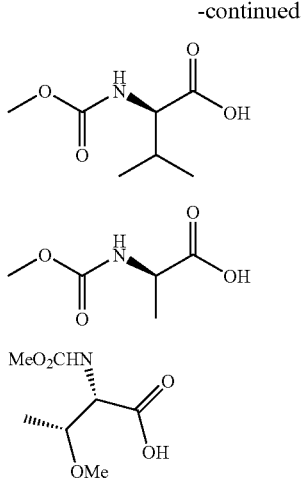

Cap-84

Cap-85

Cap-86

To a mixture of O-methyl-L-threonine (3.0 g, 22.55 mmol), NaOH (0.902 g, 22.55 mmol) in $H_2O$ (15 mL) was added $ClCO_2Me$ (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in $CH_2Cl_2$ (250 mL) and the combined organic phases were concentrated under in vacuo to afford a colorless oil (4.18 g, 97%) which was of sufficient purity for use in subsequent steps. $^1$HNMR (400 MHz, $CDCl_3$) δ 4.19 (s, 1H), 3.92-3.97 (m, 1H), 3.66 (s, 3H), 1.17 (d, J=7.7 Hz, 3H). LCMS: Anal. Calcd. for $C_7H_{13}NO_5$: 191. found: 190 (M–H)$^-$.

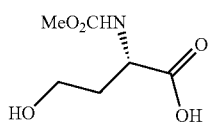

Cap-87

To a mixture of L-homoserine (2.0 g, 9.79 mmol), $Na_2CO_3$ (2.08 g, 19.59 mmol) in $H_2O$ (15 mL) was added $ClCO_2Me$ (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated under in vacuo to afford a colorless solid (0.719 g, 28%) which was of sufficient purity for use in subsequent steps. $^1$HNMR (400 MHz, $CDCl_3$) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for $C_7H_{13}NO_5$: 191. found: 192 (M+H)$^+$.

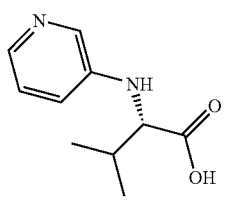

Cap-88

A mixture of L-valine (1.0 g, 8.54 mmol), 3-bromopyridine (1.8 mL, 18.7 mmol), $K_2CO_3$ (2.45 g, 17.7 mmol) and CuI (169 mg, 0.887 mmol) in DMSO (10 mL) was heated at 100° C. for 12 h. The reaction mixture was cooled to rt, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophyllized. The title compound was obtained as a foam (1.02 g, 62%). $^1$HNMR (400 MHz, DMSO-$d_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for $C_{10}H_{14}N_2O_2$: 194. found: 195 (M+H)$^+$.

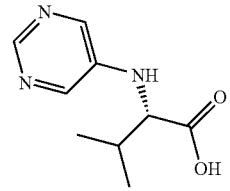

Cap-89

A mixture of L-valine (1.0 g, 8.54 mmol), 5-bromopyrimidine (4.03 g, 17.0 mmol), $K_2CO_3$ (2.40 g, 17.4 mmol) and CuI (179 mg, 0.94 mmol) in DMSO (10 mL) was heated at 100° C. for 12 h. The reaction mixture was cooled to RT, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophyllized. The title compound was obtained as a foam (1.02 g, 62%). $^1$HNMR (400 MHz, $CD_3OD$) showed the mixture to contain valine and the purity could not be estimated. The material was used as is in subsequent reactions. LCMS: Anal. Calcd. for $C_9H_{13}N_3O_2$: 195. found: 196 (M+H)$^+$.

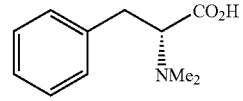

Cap-90

Cap-90 was prepared according to the method described for the preparation of Cap-1. The crude material was used as is in subsequent steps. LCMS: Anal. Calcd. for $C_{11}H_{15}NO_2$: 193. found: 192 (M–H)$^-$.

The following caps were prepared according to the method used for preparation of cap 51 unless noted otherwise:

| Cap | Structure | LCMS |
|---|---|---|
| Cap-91 | (S)-3-(methoxycarbonylamino)-3-phenylpropanoic acid | LCMS: Anal. Calcd. for $C_{11}H_{13}NO_4$: 223; found: 222 $(M - H)^-$. |
| Cap-92 | (R)-3-(methoxycarbonylamino)-3-phenylpropanoic acid | LCMS: Anal. Calcd. for $C_{11}H_{13}NO_4$: 223; found: 222 $(M - H)^-$. |
| Cap-93 | (S)-2-(methoxycarbonylamino)-3-(pyridin-2-yl)propanoic acid | LCMS: Anal. Calcd. for $C_{10}H_{12}N_2O_4$: 224; found: 225 $(M + H)^+$. |
| Cap-94 | (S)-3-(1H-imidazol-4-yl)-2-(methoxycarbonylamino)propanoic acid | LCMS: Anal. Calcd. for $C_8H_{11}N_3O_4$: 213; found: 214 $(M + H)^+$. |
| Cap-95 | (S)-3-(methoxycarbonylamino)-5-phenylpentanoic acid | LCMS: Anal. Calcd. for $C_{13}H_{17}NO_4$: 251; found: 250 $(M - H)^-$. |
| Cap-96 | (S)-3-(methoxycarbonylamino)-4-phenylbutanoic acid | LCMS: Anal. Calcd. for $C_{12}H_{15}NO_4$: 237; found: 236 $(M - H)^-$. |
| Cap-97 | (1S,2R)-2-(methoxycarbonylamino)cyclohexanecarboxylic acid | LCMS: Anal. Calcd. for $C_9H_{15}NO_4$: 201; found: 200 $(M - H)^-$. |
| Cap-98 | (1R,2S)-2-(methoxycarbonylamino)cyclohexanecarboxylic acid | LCMS: Anal. Calcd. for $C_9H_{15}NO_4$: 201; found: 202 $(M + H)^+$. |
| Cap-99 | (1S,3R)-3-(methoxycarbonylamino)cyclopentanecarboxylic acid | $^1$H NMR (400 MHz, CD$_3$OD) δ 3.88-3.94 (m, 1H), 3.60, 3.61 (s, 3H), 2.80 (m, 1H), 2.20 (m, 1H), 1.82-1.94 (m, 3H), 1.45-1.71 (m, 2H). |
| Cap-99a | (1R,3S)-3-(methoxycarbonylamino)cyclopentanecarboxylic acid | $^1$H NMR (400 MHz, CD$_3$OD) δ 3.88-3.94 (m, 1H), 3.60, 3.61 (s, 3H), 2.80 (m, 1H), 2.20 (m 1H), 1.82-1.94 (m, 3H), 1.45-1.71 (m, 2H). |
| Cap-100 | (S)-4-(2-fluorophenyl)-3-(methoxycarbonylamino)butanoic acid | LCMS: Anal. Calcd. for $C_{12}H_{14}NO_4F$: 255; found: 256 $(M + H)^+$. |
| Cap-101 | (R)-2-(methoxycarbonylamino)-3-phenylpropanoic acid | LCMS: Anal. Calcd. for $C_{11}H_{13}NO_4$: 223; found: 222 $(M - H)^-$. |
| Cap-102 | (S)-2-(methoxycarbonylamino)-3-phenylpropanoic acid | LCMS: Anal. Calcd. for $C_{11}H_{13}NO_4$: 223; found: 222 $(M - H)^-$ |

-continued

| Cap | Structure | LCMS |
|---|---|---|
| Cap-103 | 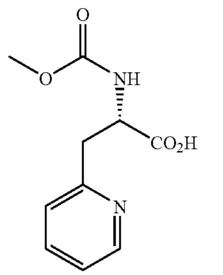 | LCMS: Anal. Calcd. for C₁₀H₁₂N₂O₄: 224; found: 225 (M + H)⁺. |
| Cap-104 | 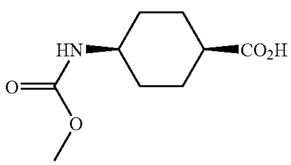 | ¹HNMR (400 MHz, CD₃OD) δ 3.60 (s, 3H), 3.50-3.53 (m, 1H), 2.66-2.69 and 2.44-2.49 (m, 1H), 1.91-2.01 (m, 2H), 1.62-1.74 (m, 4H), 1.51-1.62 (m, 2H). |
| Cap-105 | 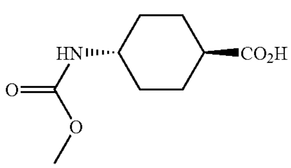 | ¹HNMR (400 MHz, CD₃OD) δ 3.60 (s, 3H), 3.33-3.35 (m, 1H, partially obscured by solvent), 2.37-2.41 and 2.16-2.23 (m, 1H), 1.94-2.01 (m, 4H), 1.43-1.53 (m, 2H), 1.17-1.29 (m, 2H). |
| Cap-106 Prepared from cis-4-aminocyclohexane carboxylic acid and acetaldehyde according to the procedure described for the synthesis of Cap-2 | | ¹HNMR (400 MHz, CD₃OD) δ 3.16 (q, J = 7.3 Hz, 4H), 2.38-2.41 (m, 1H), 2.28-2.31 (m, 2H), 1.79-1.89 (m, 2H), 1.74 (app, ddd J = 3.5, 12.5, 15.9 Hz, 2H), 1.46 (app dt J = 4.0, 12.9 Hz, 2H), 1.26 (t, J = 7.3 Hz, 6H) |
| Cap-107 | 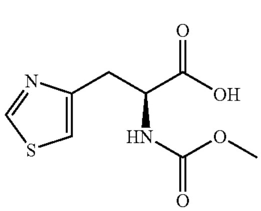 | LCMS: Anal. Calcd. for C₈H₁₀N₂O₄S: 230; found: 231 (M + H)⁺. |

-continued

| Cap | Structure | LCMS |
|---|---|---|
| Cap-108 | 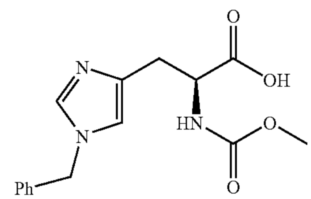 | LCMS: Anal. Calcd. for C₁₅H₁₇N₃O₄: 303; found: 304 (M + H)⁺. |
| Cap-109 | 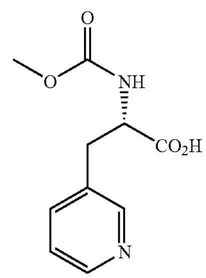 | LCMS: Anal. Calcd. for C₁₀H₁₂N₂O₄: 224; found: 225 (M + H)⁺. |
| Cap-110 | 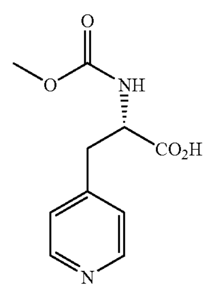 | LCMS: Anal. Calcd. for C₁₀H₁₂N₂O₄: 224; found: 225 (M + H)⁺. |
| Cap-111 | 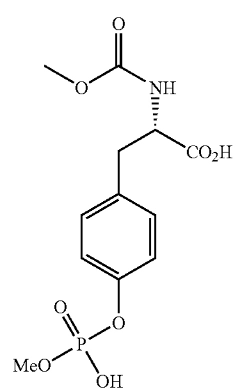 | LCMS: Anal. Calcd. for C₁₂H₁₆NO₈P: 333; found: 334 (M + H)⁺. |
| Cap-112 | 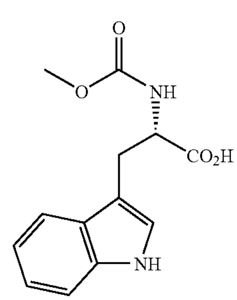 | LCMS: Anal. Calcd. for C₁₃H₁₄N₂O₄: 262; found: 263 (M + H)⁺. |

-continued

| Cap | Structure | LCMS |
|---|---|---|
| Cap-113 | (methyl carbamate of tyrosine O-benzyl ether, CO2H) | LCMS: Anal. Calcd. for $C_{18}H_{19}NO_5$: 329; found: 330 $(M + H)^+$. |
| Cap-114 | (azetidine-1-CO2Me, 2-CO2H) | $^1$HNMR (400 MHz, CDCl$_3$) δ 4.82-4.84 (m, 1H), 4.00-4.05 (m, 2H), 3.77 (s, 3H), 2.56 (s, br, 2H) |
| Cap-115 | (3-(methoxycarbonylamino)butanoic acid) | $^1$HNMR (400 MHz, CDCl$_3$) δ 5.13 (s, br, 1H), 4.13 (s, br, 1H), 3.69 (s, 3H), 2.61 (d, J = 5.0 Hz, 2H), 1.28 (d, J = 9.1 Hz, 3H). |
| Cap-116 | (3-(methoxycarbonylamino)-4-methylpentanoic acid) | $^1$HNMR (400 MHz, CDCl$_3$) δ 5.10 (d, J = 8.6 Hz, 1H), 3.74-3.83 (m, 1H), 3.69 (s, 3H), 2.54-2.61 (m, 2H), 1.88 (sept, J = 7.0 Hz, 1H), 0.95 (d, J = 7.0 Hz, 6H). |

Cap-117 to Cap-123

For the preparation of caps Cap-117 to Cap-123 the Boc amino acids were commercially available and were deprotected by treatment with 25% TFA in CH$_2$Cl$_2$. After complete reaction as judged by LCMS the solvents were removed in vacuo and the corresponding TFA salt of the amino acid was carbamoylated with methyl chloroformate according to the procedure for Cap-51.

| Cap | Structure | LCMS |
|---|---|---|
| Cap-117 | (3-(methoxycarbonylamino)-4-phenylbutanoic acid) | LCMS: Anal. Calcd. for $C_{12}H_{15}NO_4$: 237; found: 238 $(M + H)^+$. |
| Cap-118 | (3-(methoxycarbonylamino)-4-(thiophen-2-yl)butanoic acid) | LCMS: Anal. Calcd. for $C_{10}H_{13}NO_4S$: 243; found: 244 $(M + H)^+$. |
| Cap-119 | (3-(methoxycarbonylamino)-4-(thiophen-2-yl)butanoic acid, enantiomer) | LCMS: Anal. Calcd. for $C_{10}H_{13}NO_4S$: 243; found: 244 $(M + H)^+$. |

-continued

| Cap | Structure | LCMS |
|---|---|---|
| Cap-120 | 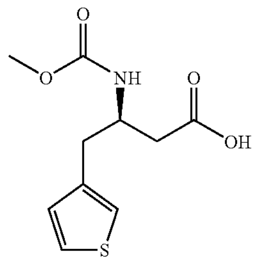 | LCMS: Anal. Calcd. for $C_{10}H_{13}NO_4S$: 243; found: 244 $(M + H)^+$. |
| Cap-121 | 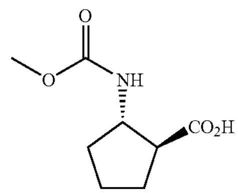 | $^1$HNMR (400 MHz, $CDCl_3$) δ 4.06-4.16 (m, 1H), 3.63 (s, 3H), 3.43 (s, 1H), 2.82 and 2.66 (s, br, 1H), 1.86-2.10 (m, 3H), 1.64-1.76 (m, 2H), 1.44-1.53 (m, 1H). |
| Cap-122 | 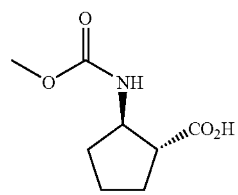 | $^1$HNMR profile is similar to that of its enantiomer, Cap-121. |
| Cap-123 | 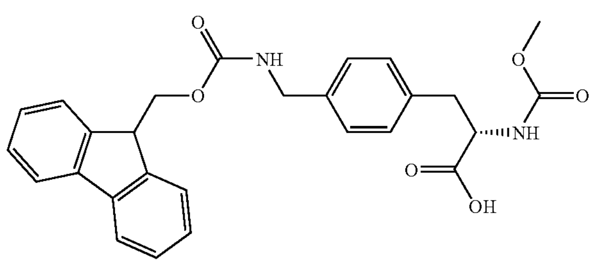 | LCMS: Anal. Calcd. for $C_{27}H_{26}N_2O_6$: 474; found: 475 $(M + H)^+$. |

Preparation of Cap-124.
(4S,5R)-5-methyl-2-oxooxazolidine-4-carboxylic acid

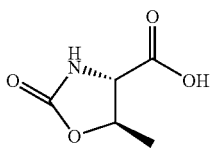

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless oil which solidified on standing. The aqueous layer was concentrated in vacuo and the resulting mixture of product and inorganic salts was triturated with EtOAc-$CH_2Cl_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, $CD_3OD$) δ 4.60 (m, 1H), 4.04 (d, J=5.0 Hz, 1H), 1.49 (d, J=6.3 Hz, 3H). LCMS: Anal. Calcd. for $C_5H_7NO_4$: 145. found: 146 $(M+H)^+$.

Preparation of Cap-125. (S)-2-(tert-butoxycarbonylamino)-4-(dimethylamino)butanoic acid

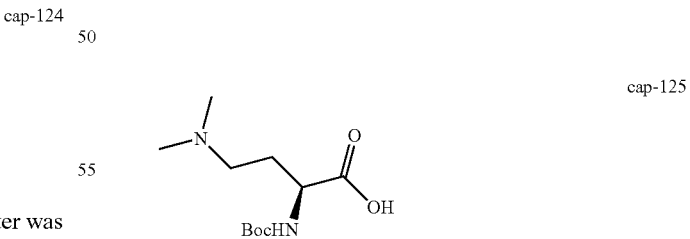

To a suspension of $Pd(OH)_2$, (20%, 100 mg), aqueous formaldehyde (37% wt, 4 ml), acetic acid, (0.5 mL) in methanol (15 mL) was added (S)-4-amino-2-(tert-butoxycarbonylamino)butanoic acid (1 g, 4.48 mmol). The reaction was purged several times with hydrogen and was stirred overnight with an hydrogen balloon room temp. The reaction mixture was filtered through a pad of diatomaceous earth (Celite™), and the volatile component was removed in vacuo. The resulting crude material was used as is for the next step. LC/MS: Anal. Calcd. for $C_{11}H_{22}N_2O_4$: 246. found: 247 $(M+H)^+$.

Preparation of 3-methyl-N-[(methyloxy)carbonyl]-L-histidine (Cap-126)

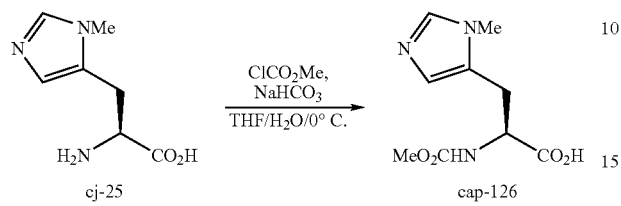

This procedure is a modification of that used to prepare Cap-51. To a suspension of 3-methyl-L-histidine (0.80 g, 4.70 mmol) in THF (10 mL) and $H_2O$ (10 mL) at 0° C. was added $NaHCO_3$ (0.88 g, 10.5 mmol). The resulting mixture was treated with $ClCO_2Me$ (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in $CH_2Cl_2$. The mixture was filtered and concentrated to give a light yellow foam (1.21 g). LCMS and $^1H$ NMR showed the material to be a 9:1 mixture of the methyl ester and the desired product. This material was taken up in THF (10 mL) and $H_2O$ (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1H$ NMR confirm the absence of the ester. The title compound was obtained as its HCl salt contaminated with inorganic salts (1.91 g, >100%). The compound was used as is in subsequent steps without further purification. $^1HNMR$ (400 MHz, $CD_3OD$) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H). LCMS: Anal. Calcd. for $C_9H_{13}N_3O_4$: 227.09. found: 228.09 $(M+H)^+$.

Preparation of (S)-2-(methoxycarbonylamino)-3-(1-methyl-1H-imidazol-4-yl)propanoic acid (Cap-127)

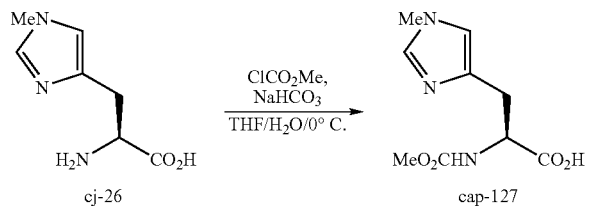

Cap-127 was prepared according to the method for Cap-126 above starting from (S)-2-amino-3-(1-methyl-1H-imidazol-4-yl)propanoic acid (1. II g, 6.56 mmol), $NaHCO_3$ (1.21 g, 14.4 mmol) and $ClCO_2Me$ (0.56 mL, 7.28 mmol). The title compound was obtained as its HCl salt (1.79 g, >100%) contaminated with inorganic salts. LCMS and $^1H$ NMR showed the presence of ca. 5% of the methyl ester. The crude mixture was used as is without further purification. $^1HNMR$ (400 MHz, $CD_3OD$) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H); LCMS: Anal. Calcd. for $C_9H_{13}N_3O_4$: 227.09. found: 228 $(M+H)^+$.

Preparation of (S)-2-(methoxycarbonylamino)-3-(1H-1,2,3-triazol-4-yl)propanoic acid (Cap-128)

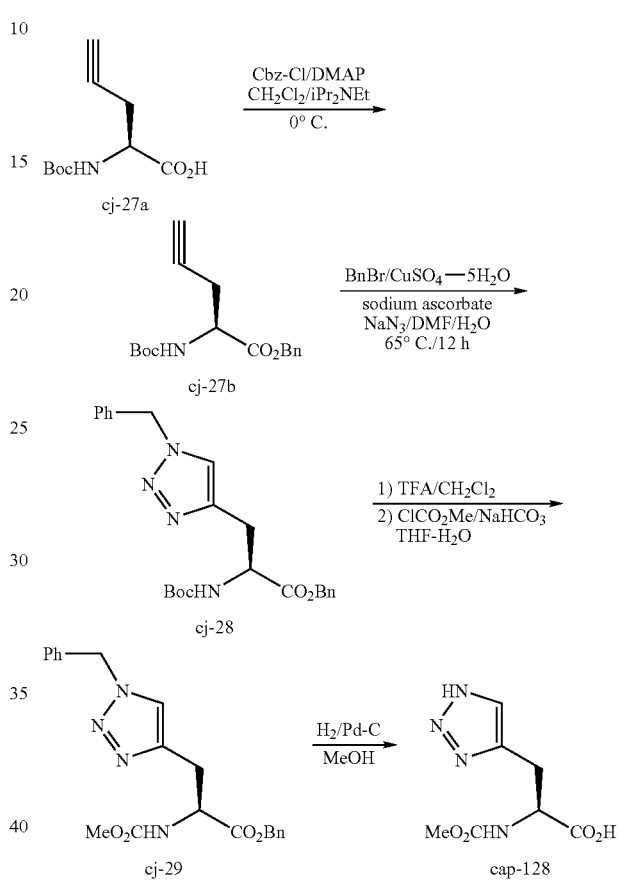

Step 1. Preparation of (S)-benzyl 2-(tert-butoxycarbonylamino)pent-4-ynoate (cj-27b)

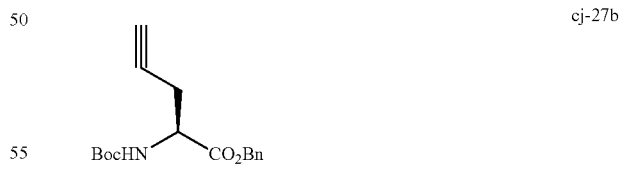

To a solution of cj-27a (1.01 g, 4.74 mmol), DMAP (58 mg, 0.475 mmol) and $iPr_2NEt$ (1.7 mL, 9.8 mmol) in $CH_2Cl_2$ (100 mL) at 0° C. was added Cbz-Cl (0.68 mL, 4.83 mmol). The solution was allowed to stir for 4 h at 0° C., washed (1N $KHSO_4$, brine), dried ($Na_2SO_4$), filtered, and concentrated in vacuo. The residue was purified by flash column chromatography (TLC 6:1 hex:EtOAc) to give the title compound (1.30 g, 91%) as a colorless oil. $^1HNMR$ (400 MHz, $CDCl_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303. found: 304 $(M+H)^+$.

Step 2. Preparation of (S)-benzyl 3-(1-benzyl-1H-1,2,3-triazol-4-yl)-2-(tert-butoxycarbonylamino)propanoate (cj-28)

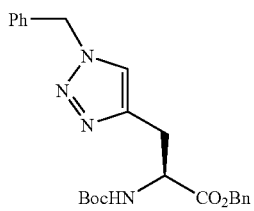

cj-28

To a mixture of (S)-benzyl 2-(tert-butoxycarbonylamino) pent-4-ynoate (0.50 g, 1.65 mmol), sodium ascorbate (0.036 g, 0.18 mmol), $CuSO_4 \cdot 5H_2O$ (0.022 g, 0.09 mmol) and $NaN_3$ (0.13 g, 2.1 mmol) in $DMF-H_2O$ (5 mL, 4:1) at rt was added BnBr (0.24 mL, 2.02 mmol) and the mixture was warmed to 65° C. After 5 h LCMS indicated low conversion. A further portion of $NaN_3$ (100 mg) was added and heating was continued for 12 h. The reaction was poured into EtOAc and $H_2O$ and shaken. The layers were separated and the aqueous layer extracted 3× with EtOAc and the combined organic phases washed ($H_2O \times 3$, brine), dried ($Na_2SO_4$), filtered, and concentrated. The residue was purified by flash (Biotage, 40+M 0-5% MeOH in $CH_2Cl_2$; TLC 3% MeOH in $CH_2Cl_2$) to afford a light yellow oil which solidified on standing (748.3 mg, 104%). The NMR was consistent with the desired product but suggests the presence of DMF. The material was used as is without further purification. $^1$HNMR (400 MHz, DMSO-$d_6$) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H). LCMS: Anal. Calcd. for $C_{24}H_{28}N_4O_4$: 436. found: 437 $(M+H)^+$.

Step 2. Preparation of (S)-benzyl 3-(1-benzyl-1H-1,2,3-triazol-4-yl)-2-(methoxycarbonylamino)propanoate (cj-29)

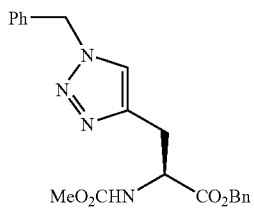

cj-29

A solution of (S)-benzyl 3-(1-benzyl-1H-1,2,3-triazol-4-yl)-2-(tert-butoxycarbonylamino)propanoate (0.52 g, 1.15 mmol) in $CH_2Cl_2$ was added TFA (4 mL). The mixture was allowed to stir at room temperature for 2 h. The mixture was concentrated in vacuo to give a colorless oil which solidified on standing. This material was dissolved in $THF-H_2O$ and cooled to 0° C. Solid $NaHCO_3$ (0.25 g, 3.00 mmol) was added followed by $ClCO_2Me$ (0.25 mL, 3.25 mmol). After stirring for 1.5 h the mixture was acidified to pH~2 with 6N HCl and then poured into $H_2O$-EtOAc. The layers were separated and the aq phase extracted 2× with EtOAc. The combined org layers were washed ($H_2O$, brine), dried ($Na_2SO_4$), filtered, and concentrated in vacuo to give a colorless oil (505.8 mg, 111%, NMR suggested the presence of an unidentified impurity) which solidified while standing on the pump. The material was used as is without further purification. $^1$HNMR (400 MHz, DMSO-$d_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for $C_{21}H_{22}N_4O_4$: 394. found: 395 $(M+H)^+$.

Step 3. Preparation of (S)-2-(methoxycarbonylamino)-3-(1H-1,2,3-triazol-4-yl)propanoic acid (Cap-128)

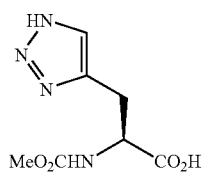

cap-128

(S)-benzyl 3-(1-benzyl-1H-1,2,3-triazol-4-yl)-2-(methoxycarbonylamino)propanoate (502 mg, 1. II mmol) was hydrogenated in the presence of Pd—C (82 mg) in MeOH (5 mL) at atmospheric pressure for 12 h. The mixture was filtered through diatomaceous earth (Celite™) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification.

$^1$HNMR (400 MHz, DMSO-$d_6$) δ 12.78 (s, br, 1H), 7.59 (s, 1H), 7.50 (d, J=8.0 Hz, 1H), 4.19-4.24 (m, 1H), 3.49 (s, 3H), 3.12 (dd, J=4.8, 14.9 Hz, 1H), 2.96 (dd, J=9.9, 15.0 Hz, 1H). LCMS: Anal. Calcd. for $C_7H_{10}N_4O_4$: 214. found: 215 $(M+H)^+$.

Preparation of (S)-2-(methoxycarbonylamino)-3-(1H-pyrazol-1-yl)propanoic acid (Cap-129)

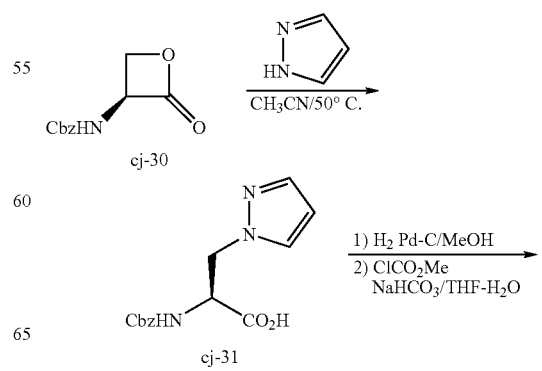

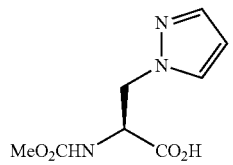

cap-129

Step 1. Preparation of (S)-2-(benzyloxycarbonylamino)-3-(1H-pyrazol-1-yl)propanoic acid (cj-31)

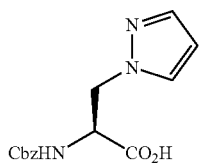

cj-31

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%). m.p. 165.5-168° C. lit m.p. 168.5-169.5 [Vederas et al. J. Am. Chem. Soc. 1985, 107, 7105]. $^1$HNMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289. found: 290 (M+H)$^+$.

Step 2. Preparation of (S)-2-(methoxycarbonylamino)-3-(1H-pyrazol-1-yl)propanoic acid (Cap-129)

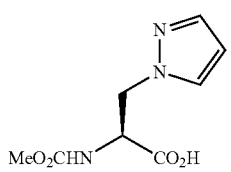

cap-129

(S)-2-(benzyloxycarbonylamino)-3-(1H-pyrazol-1-yl)propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the reaction mixture was diluted with 5 mL H$_2$O and a few drops of 6N HCl. The homogeneous solution was filtered through diatomaceous earth (Celite™), and the MeOH removed in vacuo. The remaining solution was frozen and lyophyllized to give a yellow foam (188.9 mg). This material was suspended in THF-H$_2$O (1:1, 10 mL) and then cooled to 0° C. To the cold mixture was added NaHCO$_3$ (146.0 mg, 1.74 mmol) carefully (evolution of CO$_2$). After gas evolution had ceased (ca. 15 min) ClCO$_2$Me (0.06 mL, 0.78 mmol) was added dropwise. The mixture was allowed to stir for 2 h and was acidified to pH~2 with 6N HCl and poured into EtOAc. The layers were separated and the aqueous phase extracted with EtOAC (×5). The combined organic layers were washed (brine), dried (Na$_2$SO$_4$), filtered, and concentrated to give the title compound as a colorless solid (117.8 mg, 79%). $^1$HNMR (400 MHz, DMSO-d$_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213. found: 214 (M+H)$^+$.

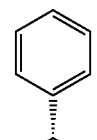

cap-130

Cap-130. N-Acetyl-(R)-Phenylglycine

Cap-130 was prepared by acylation of commercially available (R)-phenylglycine analgous to the procedure given in: Calmes, M.; Daunis, J.; Jacquier, R.; Verducci, J. Tetrahedron, 1987, 43(10), 2285.

Cap-131:

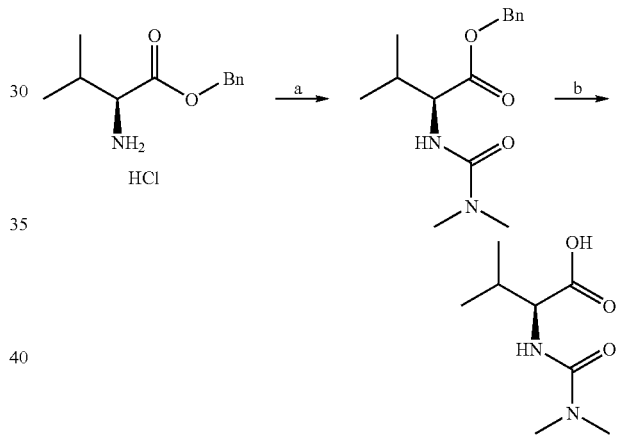

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO$_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of clear oil. $^1$H NMR (300 MHz, DMSO-d$_6$) δ ppm 0.84 (d, J=6.95 Hz, 3H) 0.89 (d, J=6.59 Hz, 3H) 1.98-2.15 (m, 1H) 2.80 (s, 6H) 5.01-5.09 (m, J=12.44 Hz, 1H) 5.13 (d, J=12.44 Hz, 1H) 6.22 (d, J=8.05 Hz, 1H) 7.26-7.42 (m, 5H). LC (Cond. 1): RT=1.76 min; MS: Anal. Calcd. for [M+H]$^+$ C$_{16}$H$_{22}$N$_2$O$_3$: 279.17. found 279.03.

Step b: To a MeOH (50 mL) solution of the intermediate prepared above (2.35 g; 8.45 mmol) was added Pd/C (10%; 200 mg) and the resulting black suspension was flushed with N$_2$ (3×) and placed under 1 atm of H$_2$. The mixture was stirred at room temperature overnight and filtered though a microfiber filter to remove the catalyst. The resulting clear solution was then concentrated under reduced pressure to obtain 1.43 g (89%) of Cap-131 as a white foam, which was used without further purification. $^1$H NMR (500 MHz, DMSO-$d_6$) δ ppm 0.87 (d, J=4.27 Hz, 3H) 0.88 (d, J=3.97 Hz, 3H) 1.93-2.11 (m, 1H) 2.80 (s, 6H) 3.90 (dd, J=8.39, 6.87 Hz, 1H) 5.93 (d, J=8.54 Hz, 1H) 12.36 (s, 1H).). LC (Cond. 1): RT=0.33 min; MS: Anal. Calcd. for [M+H]$^+$ C$_8$H$_{17}$N$_2$O$_3$: 1898.12. found 189.04.

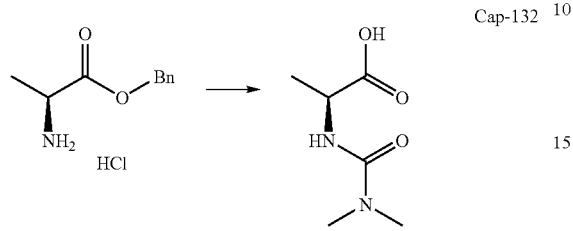

Cap-132

Cap-132 was prepared from (S)-benzyl 2-aminopropanoate hydrochloride according to the method described for Cap-131. $^1$H NMR (500 MHz, DMSO-$d_6$) δ ppm 1.27 (d, J=7.32 Hz, 3H) 2.80 (s, 6H) 4.06 (qt, 1H) 6.36 (d, J=7.32 Hz, 1H) 12.27 (s, 1H). LC (Cond. 1): RT=0.15 min; MS: Anal. Calcd. for [M+H]$^+$ C$_6$H$_{13}$N$_2$O$_3$: 161.09. found 161.00.

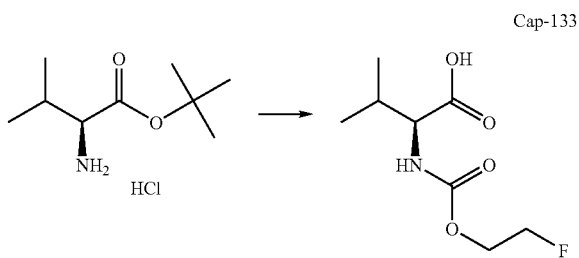

Cap-133

Cap-133 was prepared from (S)-tert-butyl 2-amino-3-methylbutanoate hydrochloride and 2-fluoroethyl chloroformate according to the method described for Cap-47. $^1$H NMR (500 MHz, DMSO-$d_6$) δ ppm 0.87 (t, J=6.71 Hz, 6H) 1.97-2.10 (m, 1H) 3.83 (dd, J=8.39, 5.95 Hz, 1H) 4.14-4.18 (m, 1H) 4.20-4.25 (m, 1H) 4.50-4.54 (m, 1H) 4.59-4.65 (m, 1H) 7.51 (d, J=8.54 Hz, 1H) 12.54 (s, 1H).

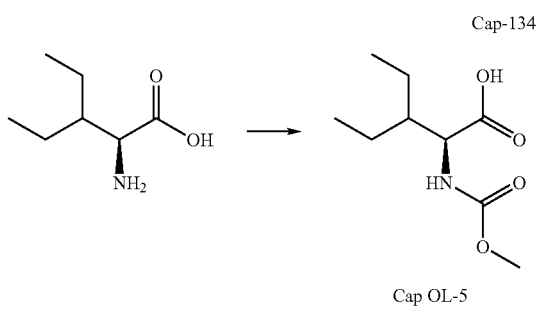

Cap-134

Cap OL-5

Cap-134 was prepared from (S)-diethyl alanine and methyl chloroformate according to the method described for Cap-51. $^1$H NMR (500 MHz, DMSO-$d_6$) δ ppm 0.72-0.89 (m, 6H) 1.15-1.38 (m, 4H) 1.54-1.66 (m, 1H) 3.46-3.63 (m, 3H) 4.09 (dd, J=8.85, 5.19 Hz, 1H) 7.24 (d, J=8.85 Hz, 1H) 12.55 (s, 1H). LC (Cond. 2): RT=0.66 min; MS: Anal. Calcd. for [M+H]$^+$ C$_9$H$_{18}$NO$_4$: 204.12. found 204.02.

Biological Activity

An HCV Replion assay was utilized in the present disclosure, and was prepared, conducted and validated as described in commonly owned PCT/US2006/022197 and in O'Boyle et. al. *Antimicrob Agents Chemother.* 2005 April; 49(4): 1346-53.

HCV 1b-377-neo replicon cells were used to test representative compounds described within this disclosure as were cells resistant to compound A due to a Y2065H mutation in NS5A (described in application PCT/US2006/022197). The compounds tested were determined to have an approximately 10-fold less inhibitory activity on cells resistant to compound A than wild-type cells indicating a related mechanism of action between the two compound series. Thus, the compounds can be effective to be effective to inhibit the function of the HCV NS5A protein and are understood to be as effective in combinations as previously described in application PCT/US2006/022197 and commonly owned WO/04014852. Further, the compounds are effective against the HCV 1b genotype. It should also be understood that the compounds of the present disclosure can inhibit multiple genotypes of HCV. Table 2 shows the EC50 values of representative compounds of the present disclosure against the HCV 1b genotype. Ranges are as follows: A=1-10 μM; B=100-999 nM; C=1-99 nM; and D=10-999 pM.

TABLE 2

| Example Number | Structure | Activity |
|---|---|---|
| 30 | 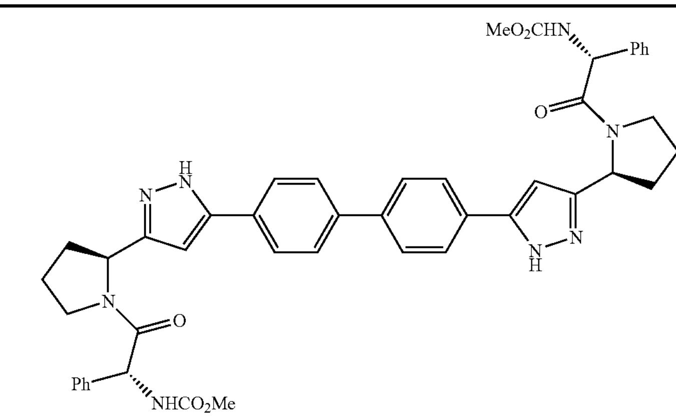 | C |

TABLE 2-continued

| Example Number | Structure | Activity |
|---|---|---|
| 31 | 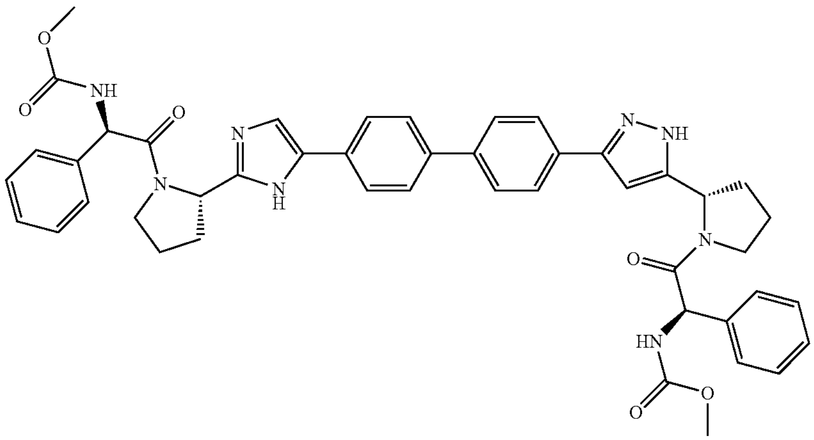 | D |
| 32 | 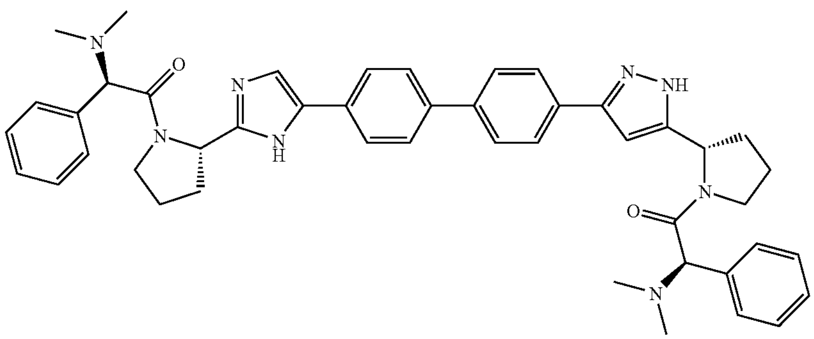 | D |
| 33 | 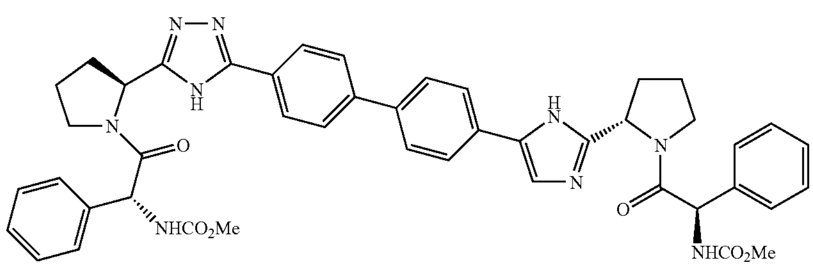 | D |
| 34 | 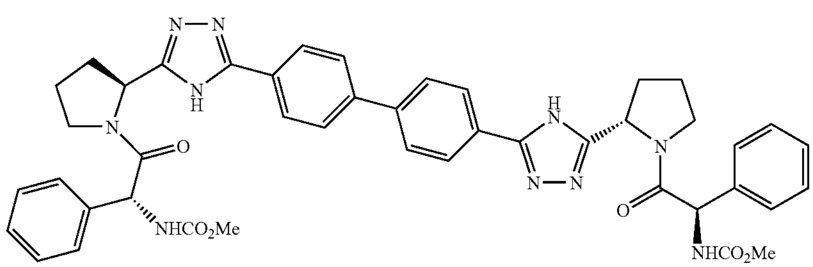 | D |
| 35 | 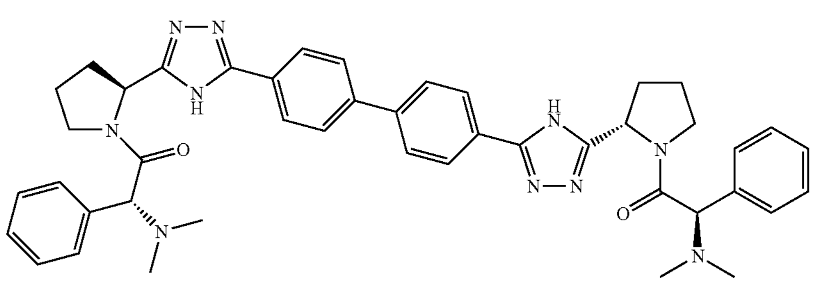 | C |

TABLE 2-continued

| Example Number | Structure | Activity |
|---|---|---|
| 36 | 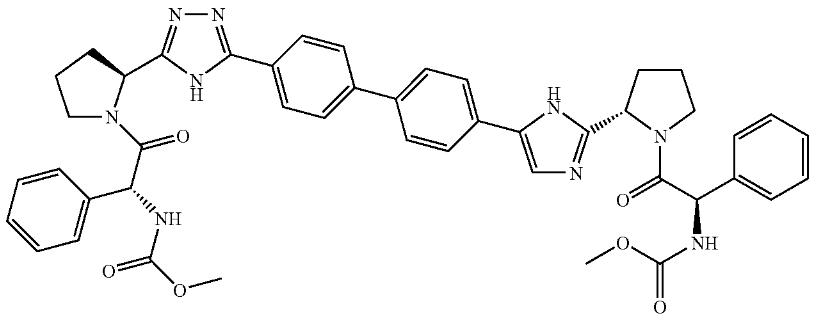 | D |
| 37 | 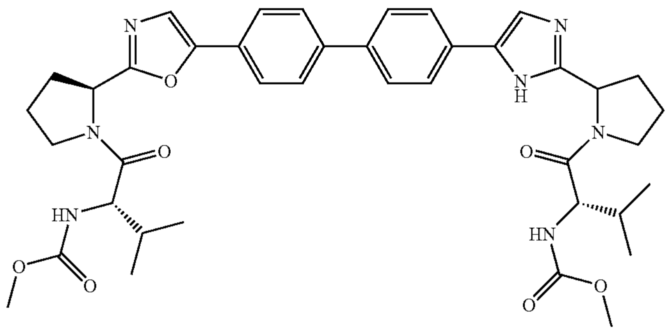 | D |
| 38 | 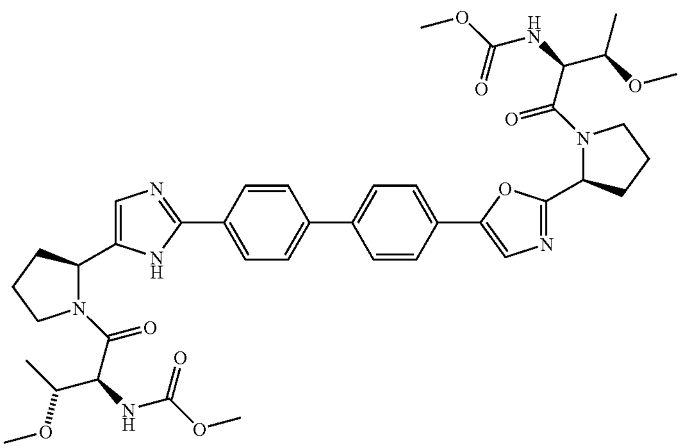 | D |

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I)

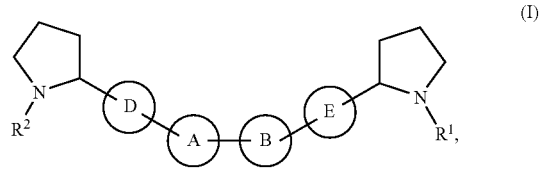

or a pharmaceutically acceptable salt thereof, wherein
A and B are each phenyl;
D and E are each five-membered aromatic rings containing one, two, or three heteroatoms independently selected from nitrogen, oxygen, and sulfur; provided that at least one of D and E is other than imidazole;
$R^1$ and $R^2$ are independently selected from hydrogen, $R^3$—C(O)—; and
each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl.

2. The compound of claim 1, or a pharmaceutically acceptable salt thereof, wherein one of D and E is imidazole.

3. The compound of claim 1, or a pharmaceutically acceptable salt thereof, wherein at least one of D and E is selected from pyrazole, triazole, and oxadiazole.

4. The compound of claim 1, or a pharmaceutically acceptable salt thereof, wherein $R^3$ is selected from alkoxy and arylalkyl.

5. A compound of Formula (II)

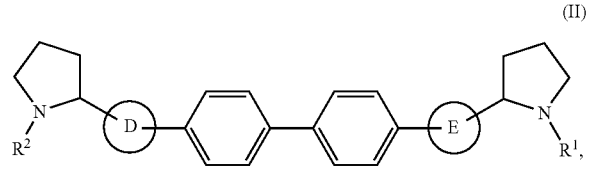

(II)

or a pharmaceutically acceptable salt thereof, wherein
D and E are each five-membered aromatic rings containing one, two, or three heteroatoms independently selected from nitrogen, oxygen, and sulfur; provided that at least one of D and E is other than imidazole;
$R^3$ and $R^4$ are independently selected from hydrogen and $R^3$—C(O)—; and
each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl.

6. A compound of Formula (III)

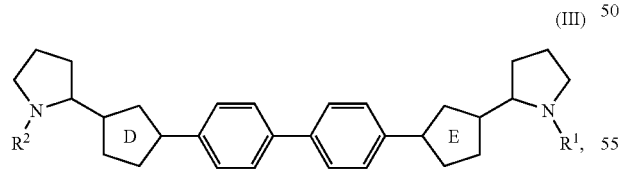

(III)

or a pharmaceutically acceptable salt thereof, wherein
D and E are each five-membered aromatic rings containing one, two, or three heteroatoms independently selected from nitrogen, oxygen, and sulfur; provided that at least one of D and E is other than imidazole; and provided that both D and E are each substituted through carbon atoms;
$R^1$ and $R^2$ are independently selected from hydrogen and $R^3$—C(O)—; and
each $R^3$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, ($NR^cR^d$)alkenyl, ($NR^cR^d$)alkyl, and ($NR^cR^d$)carbonyl.

7. The compound of claim 6, or a pharmaceutically acceptable salt thereof, wherein
D and E are independently selected from imidazole, pyrazole, triazole, and oxadiazole; provided at least one of D and E is other than imidazole; and provided that both D and E are each substituted through carbon atoms; and
$R^3$ is selected from alkoxy and arylalkyl.

8. A composition comprising a compound of claim 1, or a pharmaceutically acceptable salt thereof, and a pharmaceutically acceptable carrier.

9. The composition of claim 8 further comprising one or two additional compounds having anti-HCV activity wherein at least one of the additional compounds is an interferon or a ribavirin.

10. The composition of claim 9 wherein the interferon is selected from interferon alpha 2B, pegylated interferon alpha, consensus interferon, interferon alpha 2A, and lymphoblastoid interferon tau.

11. A method of treating an HCV infection in a patient, comprising administering to the patient a therapeutically effective amount of a compound of claim 1, or a pharmaceutically acceptable salt thereof.

12. The method of claim 11 further comprising administering one or two additional compounds having anti-HCV activity prior to, after or simultaneously with the compound of claim 1, or a pharmaceutically acceptable salt thereof wherein at least one of the additional compounds is an interferon or a ribavirin.

13. The method of claim 12 wherein the interferon is selected from interferon alpha 2B, pegylated interferon alpha, consensus interferon, interferon alpha 2A, and lymphoblastoid interferon tau.

* * * * *